US008273342B2

(12) United States Patent
Davies et al.

(10) Patent No.: US 8,273,342 B2
(45) Date of Patent: Sep. 25, 2012

(54) ANTI-VIRUS THERAPY FOR RESPIRATORY DISEASES

(75) Inventors: Donna Elizabeth Davies, Salisbury (GB); Peter Alexander Blanch Wark, Maitland (AU); Stephen Holgate, Romsey (GB); Sebastian L. Johnston, London (GB)

(73) Assignee: University of Southampton, Southampton (GB)

( * ) Notice: Subject to any disclaimer, the term of this patent is extended or adjusted under 35 U.S.C. 154(b) by 170 days.

(21) Appl. No.: 12/487,563

(22) Filed: Jun. 18, 2009

(65) Prior Publication Data

US 2009/0257980 A1  Oct. 15, 2009

Related U.S. Application Data

(60) Division of application No. 11/517,763, filed on Sep. 8, 2006, now Pat. No. 7,569,216, and a continuation-in-part of application No. PCT/GB2005/050031, filed on Mar. 7, 2005.

(60) Provisional application No. 60/783,297, filed on Mar. 17, 2006.

(30) Foreign Application Priority Data

Mar. 12, 2004 (GB) .................................. 0405634.7
Sep. 9, 2005 (GB) .................................... 518425.4

(51) Int. Cl.
*A61K 38/21* (2006.01)
*A61K 48/00* (2006.01)

(52) U.S. Cl. ....................... 424/85.6; 514/44 R; 514/889
(58) Field of Classification Search ........................ None
See application file for complete search history.

(56) References Cited

U.S. PATENT DOCUMENTS

| | | | |
|---|---|---|---|
| 6,030,609 | A | 2/2000 | Panuska et al. |
| 6,596,260 | B1 | 7/2003 | Brugger et al. |
| 2001/0031263 | A1 | 10/2001 | Panuska et al. |
| 2003/0072718 | A1 | 4/2003 | Platz et al. |
| 2004/0037809 | A1 | 2/2004 | Quay et al. |

FOREIGN PATENT DOCUMENTS

| | | |
|---|---|---|
| EP | 1 133 997 | 9/2001 |
| WO | WO-02/36628 | 5/2002 |
| WO | WO-02/072019 | 9/2002 |
| WO | WO-03/066002 | 8/2003 |
| WO | WO-2004/037995 | 5/2004 |
| WO | WO-2005/023862 | 3/2005 |
| WO | WO-2005/087253 | 9/2005 |
| WO | WO-2005/097165 | 10/2005 |

OTHER PUBLICATIONS

Gauvreau et al (American Journal of Respiratory and Critical Care Medicine 174:15-20, 2006).*
Rudolph et al (Molecular Therapy 12:493-501, 2005).*
McLachlan et al (Molecular Therapy 15:348-354, 2007).*
GB Search Report and Opinion for GB 0405634.7, dated Aug. 16, 2004.
Takahashi et al., "The Japanese Interferon Study Group (JISG) has established the efficacy of human interferon-β for serious CMV pneumonitis in kidney recipients," Transplantation Int. (1992) 5(Suppl. 1):S133-S137.
Takahashi et al., "Effect of Human Interferon-β on Life-Threatening Viral Pneumonitis in Kidney Transplant Recipients," Transplantation Proceedings (1987) XIX(5):4089-4095.
Satoh et al., "Induction of Tissue 2'5' AS and Suppression of Delayed Type of Asthma Reaction by Oral Administration of IFN-β in Guinea Pig Asthma Model," J. Interferon and Cytokine Res. (1997) 17:S96, W40.
Satoh et al., "Suppression of Late Asthmatic Response by Low-Dose Oral Administration of Interferon-β in the Guinea Pig Model of Asthma," J. Interferon and Cytokine Res. (1999) 19:887-894.
Hensley et al., "Interferon-β 1a and SARS Coronavirus Replication," Emerging Infectious Disease (2004) 10:317-319.
Cinatl et al., "Treatment of SARS with human interferons," Lancet (2003) 362:293-294.
Bradley et al., "A Phase III Comparison of Radiation Therapy with or without Recombinant β-Interferon for Poor-Risk Patients with Locally Advanced Non-Small-Cell Lung Cancer (RTOG 93-04)," Int. J. Radiation Oncology Biol. Phys. (2002) 52:1173-1179.
Hill et al., "Effect of an Interferon Inducer on Human Respiratory Viruses," Bacteriological Proceedings (1969) 69:149, V3.
Soike et al., "Effect of Interferon on Respiratory Infections of Animals," Texas Reports on Biology and Medicine (1977) 35:455-460.
International Search Report for PCT/GB2005/050031, mailed on Sep. 30, 2005, 4 pages.
Overlack et al., "Clinical and Functional Course of COPD in Hypertensive Patients with Concomitant Chronic Bronchitis and Emphysema During Treatment with an Ace Inhibitor, Perindopril," Journal of Drug Development (1993) 6:5-9.
Higgins et al., "Interferon-β$_{ser}$ As Prophylaxis Against Experimental Rhinovirus Infection in Volunteers," Journal of Interferon Research (1986) 6:153-159.
Sperber et al., "Comparative Susceptibility of Respiratory Viruses to Recombinant Interferons-α$_{2b}$ and —β," Journal of Interferon Research (1989) 9:285-293.
Sperber et al., "Otologic Effects of Interferon Beta Serine in Experimental Rhinovirus Colds," Arch. Otolaryngol. Head Neck Surg. (1992) 118:933-936.

(Continued)

*Primary Examiner* — Mary E Mosher
(74) *Attorney, Agent, or Firm* — Morrison & Foerster LLP

(57) ABSTRACT

The present invention provides the use of IFN-β, an agent that increases the expression of IFN-β, or a polynucleotide which is capable of expressing IFN-β or said agent for the manufacture of a medicament for the treatment of rhinovirus-induced exacerbation of a respiratory disease selected from asthma and chronic obstructive pulmonary disease, wherein said treatment is by airway delivery of said medicament, e.g. by use of an aerosol nebulizer. Also provided is IFN-λ for the same purpose.

8 Claims, 39 Drawing Sheets

OTHER PUBLICATIONS

Sperber et al., "Ineffectiveness of Recombinant Interferon-$\beta_{serine}$ Nasal Drops for Prophylaxis of Natural Colds," J. Infectious Dis. (1989) 160:700-705.

Wark et al., "Asthmatic bronchial epithelial cells have a deficient innate immune response to infection with rhinovirus," J. Exp. Med. (2005) 201:937-947.

Contoli et al., "Rhinovirus induces IFN-Lambdas in bronchial epithelial cells: new cytokines with anti-viral activity against rhinovirus," European Respiratory Journal (2005) 26(Suppl. 49 Sept.) p. 122, PP50.

Contoli et al., Nature Medicine (2006) 12(9):1023-1026.

Bartlett et al., Journal of General Virology (2005) 86(6):1589-1596.

Coccia et al., European Journal of Immunology (2004) 34:796-805.

International Search Report for PCT/GB2006/050281, mailed on Mar. 19, 2007, 5 pages.

Kotenko et al., Nature Immunology (2003) 4:69-77.

Meager et al., Cytokine (2005) 31(2):109-118.

Osterlund et al., Journal of Virology (2005) 79(15):9608-9617.

Sheppard et al., Nature Immunology (2003) 4:63-68.

Edwards et al., Annual Review of Biomedical Engineering (2002) 4:93-107.

Edwards et al., Pulmonary Pharmacology & Therapeutics (2006) 19:320-330.

Johnson, American Journal of Hospital Pharmacy (1989) 46:1845-1855.

* cited by examiner (n=1)

TaqMan® PCR a HBEC rhinovirus 16 IFNA.1 IFNA.2 mRNA expression b HBEC rhinovirus 16 infection IL-29, IFNB mRNA expression a   HEBC RV1B IFNA.1 IFNA.2 mRNA expression b   HEBC RV1B IL-29 IFNB mRNA expression a  HBEC Influenza IFNA.1 IFNA.2 mRNA expression b  HBEC influenza infection IL-29 IFNB mRNA expression

ANTI-VIRUS THERAPY FOR RESPIRATORY DISEASES

CROSS-REFERENCE TO RELATED APPLICATIONS

This application is a divisional of U.S. application Ser. No. 11/517,763, filed Sep. 8, 2006, now U.S. Pat. No. 7,569,216 now allowed, which claims the benefit of priority of U.S. Provisional Application No. 60/783,297, filed Mar. 17, 2006, as well as the benefit of priority of GB Patent Application No. 518425.4, filed Sep. 9, 2005; and which is also a continuation-in-part of PCT/GB2005/050031, filed on Mar. 7, 2005, published in English as WO 2005/087253, which claims the benefit of priority to GB Patent Application No. 0405634.7, filed Mar. 12, 2004. The contents of these document are incorporated herein by reference.

Reference To Sequence Listing Submitted Via EFS-WEB

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows:

| File Name | Date of Creation | Size (bytes) |
|---|---|---|
| 255352002010Seqlist.txt | Jun. 17, 2009 | 18,497 bytes |

FIELD OF INVENTION

The invention relates to anti-virus therapy for respiratory diseases. More specifically, the invention relates inter alia to the treatment of rhinovirus-induced exacerbations of asthma or chronic obstructive respiratory disease (COPD) by airway delivery of interferon-$\beta$ (IFN-$\beta$) or an agent that increases IFN-$\beta$ expression. Interferon lambda (IFN-$\lambda$) is also proposed for the same purpose. Both asthma and COPD are examples of inflammatory airways disease in which the common cold virus (rhinovirus) is recognised to cause exacerbations associated with severe clinical problems.

BACKGROUND ART

Viral respiratory tract infections lead to the exacerbation of a number of respiratory diseases. In fact, viral respiratory tract infections are responsible for 85% of asthma exacerbations (Johnston et al., BMJ, 1995; 310: 1225-8; Nicholson et al., BMJ, 1993; 307: 982-6), including the most severe requiring hospitalisation (Johnston et al., Am. J. Respir. Crit. Care Med. 1996; 154: 654-660). It is of concern that viral infections can trigger severe asthma exacerbations even when there is good asthma control by compliant patients taking optimal doses of inhaled corticosteroids (Reddel et al., Lancet, 1999; 353: 364-369). The most common pathogen associated with asthma exacerbations is rhinovirus. Infection with rhinovirus leads to the release of inflammatory mediators (Teran et al., Am. J. Respir. Crit. Care Med. 1997; 155: 1362-1366) and increased bronchial responsiveness (Grunberg et al., Am. J. Respir. Crit. Care Med. 1997; 156: 609-616).

Subjects with asthma do not appear to be more susceptible in acquiring viral respiratory tract infections but they do have more severe lower respiratory tract symptoms (Come et al., Lancet, 2002; 359: 831-834). Although rhinovirus is known to infect bronchial epithelial cells (Gern et al., Am. J. Respir. Crit. Care Med. 1997; 155: 1159-1161) and has been isolated from the lower airway (Papadopoulos et al., J. Infect. Dis., 2000; 1821: 1875-1884; Gern et al., Am. J. Respir. Crit. Care Med. 1997; 155: 1159-1161), the reasons why the asthmatic lower respiratory tract is more prone to the effects of infection with rhinovirus are unclear. It is therefore necessary to determine why asthmatic bronchial epithelial cells have an abnormal response(s) to virus infection that causes increased viral replication and shedding leading to prolonged and augmented pro-inflammatory responses and associated exacerbation of asthma symptoms. It is also necessary to provide treatments for virally-induced exacerbations of asthma.

Surprisingly, it has been found that asthmatic bronchial cells are abnormal in their response to viral infection leading to increased virion production compared to healthy normal controls. This is despite the fact that both asthmatic and healthy cells mount an early inflammatory response to infection. It has also been shown that asthmatic cells are more resistant to early apoptosis following infection and have a deficient type I interferon response. This early apoptotic response is a key protective mechanism since inhibition of apoptosis in healthy control cells leads to enhanced viral yield. Therefore the increased virion production by asthmatic bronchial epithelial cells is associated with the ability of the cells to bypass apoptosis. Furthermore, it has been found that induction of apoptosis in asthmatic bronchial epithelial cells using IFN-$\beta$ causes a significant reduction in infectious virion production. The invention therefore relates to the treatment of virally-induced exacerbations of asthma using an apoptosis-inducing agent, preferably IFN-$\beta$ or an analog thereof.

U.S. Pat. No. 6,030,609 has previously proposed a method for treating respiratory syncytial virus (RSV) infection in the airways by aerosol delivery of IFN-$\beta$. This proposal was made solely on the basis of experiments with cultured lung epithelial cells. There is no mention in U.S. Pat. No. 6,030,609 of asthma and more particularly rhinovirus-induced exacerbation of asthma, which as indicated above is a serious clinical problem. Indeed, it is not possible to extrapolate from the experiments reported in U.S. Pat. No. 6,030,609 that IFN-$\beta$ would be effective in treating rhinovirus-induced exacerbation of asthma, as RSV is known to produce proteins that interfere with Type I interferon production (Bossert & Conzelmann, Respiratory syncytial virus (RSV) nonstructural (NS) proteins as host range determinants: a chimeric bovine RSV with NS genes from human RSV is attenuated in interferon-competent bovine cells. J. Virol. (2002) 76, 4287-93; and Spann et al., Suppression of the induction of alpha, beta, and lambda interferons by the NS1 and NS2 proteins of human respiratory syncytial virus in human epithelial cells and macrophages [corrected]. J. Virol. (2004) Apr.; 78(8): 4363-9; Erratum in: J. Virol. (2005) 78 (12):6705), whereas no similar activity is known to be produced by rhinovirus. Furthermore, although the first clinical trial in the general population using IFN-$\beta$-ser against experimental rhinovirus infection showed promising beneficial effects (Higgins P G, Al-Nakib W, Willman J, Tyrrell D A. Interferon-beta ser as prophylaxis against experimental rhinovirus infection in volunteers. J. Interferon Res. (1986) 6:153-9), in a subsequent trial for prophylaxis of natural colds, IFN-$\beta$-ser was found to be ineffective (Sperber S J, Levine P A, Sorrentino J V, Riker D K, Hayden F G, Ineffectiveness of recombinant interferon-beta serine nasal drops for prophylaxis of natural colds. J. Infect Dis. (1989) 160, 700-5), possibly because normal cells have an innate capacity to produce IFN-$\beta$ in response to rhinovirus infection. As indicated above, the inventors in this instance have found that a key feature that distinguishes asthmatic epithelial cells is a deficient apoptotic response due to impaired production of IFN-β that enables viral replication to proceed unchecked, thereby contributing to prolonged symptoms and disease exacerbation. While treatment of such deficiency by use of IFN-β was first proposed by the inventors in relation to rhinovirus-induced exacerbation of asthma, it is now proposed to be equally applicable to rhinovirus-induced exacerbation of COPD, which encompasses a range of conditions including chronic bronchitis and emphysema.

As indicated above, there are also now proposed new medical uses of interferon lambda (IFN-λ). More particularly, for example, use of IFN-λ is proposed to treat viral-induced exacerbation of respiratory disorders, especially for example, viral-induced exacerbation of asthma by viruses such as rhinovirus (RV), respiratory syncytial virus (RSV) and influenza virus. This proposal has stemmed from further investigation of interferon production in bronchial epithelial cells and bronchoalveolar lavage cells of asthmatics in response to viral infection.

One family of interferons, which includes IFN-β, are the Type I interferons. The Type I interferons are a family of closely related glycoproteins comprised of thirteen IFN-α subtypes as well as IFN-β, IFN-κ, IFN-τ and IFN-ω. The different human IFN-α subtypes have been identified by analysis of human cDNA libraries and by protein analysis of the IFNs produced by stimulated lymphoblastoid cells; the reasons for their heterogeneity remain unclear. Early studies indicated that all subtypes bind the same receptor from which it was inferred that they must elicit identical responses. Subsequently, comparative studies of both purified and recombinant subtypes revealed a spectrum of anti-viral, anti-proliferative and immunomodulatory responses.

There is one type II interferon, IFN-gamma, which binds a different receptor and has largely distinct function from the type I IFNs.

Type-I interferons are a very important component of the innate immune response to respiratory virus infection. The method of protection involves initial release of IFN-β, which then stimulates further release of IFN-β and of the IFN-αs in a cascade mediated via the type-1 interferon receptor.

The interferon-λs are three closely related proteins which have more recently been discovered (Kotenko S. V. et al., Nature Immunology 2003; Vol 4, 69-77; Sheppard P et al., Nature Immunology 2003; Vol 4, 63-88). Interferon λ-1 is also known as IL-29, while Interferon λ-2 and 3 are known as IL-28a/b. These interferons bind a third receptor distinct from those of type I or type II interferons. Thus they are now termed the type III interferons. These interferons have been shown to have anti-viral activity in in vitro cell studies (see, for example, WO 2004/037995 of Zymogenetics Inc). However, their utility in protecting against any natural respiratory virus infection in humans has not previously been established.

In this connection, it is also worthy of note that IFN-β-ser has proved ineffective in trial for prophylaxis of natural colds despite its previously reported anti-viral activity (Sperber et al., J. Infect. Dis (1989) 160, 700-705) and that this may be explained by the capacity of normal cells to produce IFN-β in response to rhinovirus infection. Equally, it is not possible to extrapolate from in vitro studies with IFN-λ showing anti-viral activity that the same interferon type will have any therapeutic value against in vivo natural respiratory virus infection.

As indicated above, interestingly, investigation of interferon production by human asthmatic bronchial epithelial cells in response to rhinovirus infection firstly showed that such cells have a deficient type I interferon response in keeping with observed resistance to early apoptosis and increased virion production compared to RV-infected bronchial epithelial cells from healthy controls. Furthermore, provision of IFN-β to RV-infected asthmatic bronchial epithelial cells in culture was shown to cause a significant reduction in infectious virion production. These results laid the foundation for proposed new therapeutic utility of IFN-β in treating rhinovirus-induced exacerbation of asthma (Wark et al., J. Exp. Med. (21 Mar. 2005) 201, 937-947).

Further results have suggested extrapolation of use of IFN-β equally for treatment of RV-induced exacerbation of COPD, which encompasses a range of conditions, including chronic bronchitis and emphysema. COPD is a progressive disease of the airways that is characterised by a gradual loss of lung function. The symptoms of COPD include chronic cough and sputum production as well as shortness of breath. Cigarette smoking is the most common cause of COPD.

It has now been determined that IFN-λ polypeptides are strongly induced by respiratory virus infections including rhinovirus (the most common) and respiratory syncytial virus (RSV) in human cells. Example 6 and FIGS. 32 to 35 illustrate such induction in bronchial epithelial cells. Furthermore, the interferon-λs induce β and β also induces λ.

By analysing bronchial epithelial cells and bronchoalveolar lavage cells from asthmatic and normal volunteer patients, it has also now been shown that asthmatic bronchial epithelial cells are additionally deficient in IFN-λ gene expression and protein production when infected with rhinovirus. Such a finding was not previously shown or contemplated before the present invention and leads to the proposal that administering one or more IFN-λ polypeptides would also constitute an effective therapy for the treatment of viral-induced exacerbation of asthma.

Furthermore, it is suggested that equally IFN-λ polypeptides may be beneficial in the treatment of viral-induced exacerbation of other respiratory disorders such as COPD. By "respiratory disorder", we include in addition to asthma and COPD, allergic bronchopulmonary aspergillosis, eosinophilic pneumonia, allergic bronchitis bronchiectasis, occupational asthma, recative airayd disease syndrome, intersitial lung disease, hyperosinophilic syndrome and parasitic lung disease.

SUMMARY OF THE INVENTION

Accordingly, the invention provides the use of an agent selected from:
 (a) interferon-β (IFN-β);
 (b) an agent that increases IFN-β expression; or
 (c) a polynucleotide capable of expressing (a) or (b);
 for the manufacture of a medicament for the treatment of rhinovirus-induced exacerbation of a respiratory disease selected from asthma and COPD, wherein said treatment is by airway delivery of said medicament, e.g. by use of an aerosol nebuliser.

The invention further provides a method of treating in an individual rhinovirus-induced exacerbation of a respiratory disease selected from asthma and COPD comprising airway administration to the individual of an agent selected from the group consisting of:
 (a) interferon-β (IFN-β);
 (b) an agent that increases IFN-β expression; or
 (c) a polynucleotide capable of expressing (a) or (b).

Such treatment may be prophylactic or therapeutic treatment. By "rhinovirus induced" will be understood induction solely by rhinovirus or virus comprising largely but not exclusively rhinovirus.

There is also provided a method of treating a patient with or at risk of viral-induced exacerbation of a respiratory disorder which comprises administering to the patient in a therapeutically effective amount one or more IFN-λ polypeptides, preferably by airway delivery. As indicated above, such therapeutic treatment is of especial interest, for example, in alleviating or preventing the problems of viral-induced exacerbation of asthma, most commonly RV-induced exacerbation of asthma but also such exacerbation by, for example, RSV or influenza virus. The administration of the one or more IFN-λ polypeptides may be directly as a polypeptide or via expression from one or more polynucleotides.

The invention further provides the use of an agent selected from:
(a) one or more IFN-λ polypeptides or
(b) a polynucleotide or polynucleotides capable of expressing one or more IFN-λ polypeptides in target bronchial epithelial cells, in the manufacture of a medicament for administration to treat viral-induced exacerbation of a respiratory disorder, preferably by airway delivery of said medicament, e.g. by use of an aerosol nebuliser. The individual treated may be any animal, but preferably the individual treated will be a human, for example, preferably an asthmatic human.

In another aspect, the invention also provides a device containing a pharmaceutical composition comprising a therapeutic agent which is (i) one or more IFN-λ polypeptides or (ii) one or more polynucleotides capable of expressing one or more IFN-λ polypeptides as noted above, said device being suitable for airway delivery of said composition. Such a composition may be supplemented with an additional therapeutic agent used to treat the respiratory disorder for simultaneous, separate or sequential administration. Thus, the additional therapeutic agent may be formulated to provide a single composition or provided in a separate composition. Products suitable for such administration regimes constitute a still further aspect of the invention.

As a preferred embodiment, there is provided a product for treatment of viral-induced exacerbation of asthma comprising for simultaneous, separate or sequential airway administration (a) at least one IFN-λ polypeptide or a polynucleotide capable of expressing at least one IFN-λ polypeptide in the bronchial epithelial cells to be targeted and (b) an inhaled corticosteroid.

As a consequence of the studies reported herein, it is additionally postulated that IFN-λ polypeptides may be of benefit in relation to an allergic disorder such as asthma, independent of any viral exacerbation. It is well established that the prevalence of asthma is increasing as is the prevalence of allergic diseases in general. This increase in prevalence has been suggested to be related to an absence of infectious disease, in that those with a high exposure to infectious disease early in life have a very low risk of developing asthma and allergies later in life. It is extrapolated that both IFN-λs and IFN-β may be used as a preventative treatment by mimicking the protective role of infection.

Allergic disorders, including asthma, rhinitis, eczema, food allergies and anaphylaxis are thought to be related to impaired TH1 immune responses which themselves are a consequence of impaired type I interferon responses, both the consequence of inadequate exposure to infectious disease early in life. Data presented herein suggests that administering IFN-λs early in life could mimic the protective effect of infectious disease, promote type I interferon and TH1 immune responses and prevent the development of TH2 driven allergic disorders. This preventive therapy could be administered early in life but IFN-λs might also be administered later in life to treat/cure allergic disorder, in other words to reverse the TH2 driven sensitization and immune responses to allergens.

(2 moi) in the absence or presence of exogenous IFN-β. IFN-β mRNA was measured by reverse transcription quantitative PCR and normalised to IFN-β levels in untreated (SFM) controls.

Figure 9:
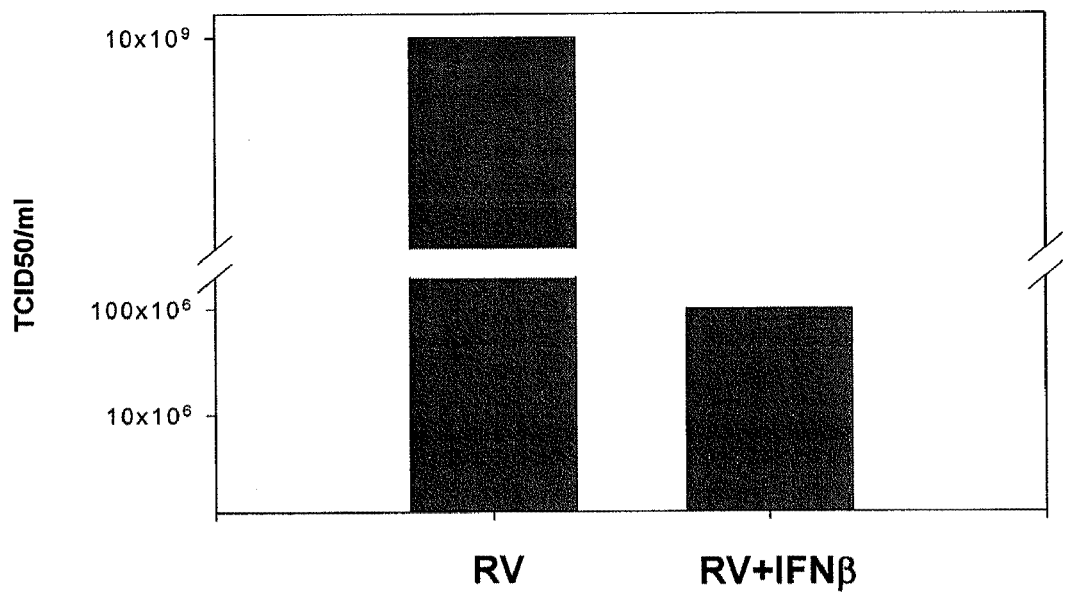

FIG. 9 shows that IFN-β reduced RV-16 replication in BECs from a COPD patient. Cells were infected with RV-16 (2 moi) in the absence or presence of exogenous IFN-β (100IU/ml). Virion production was measured as $TCID_{50}$/ml by HeLA cell titration assay.

Figure 10:
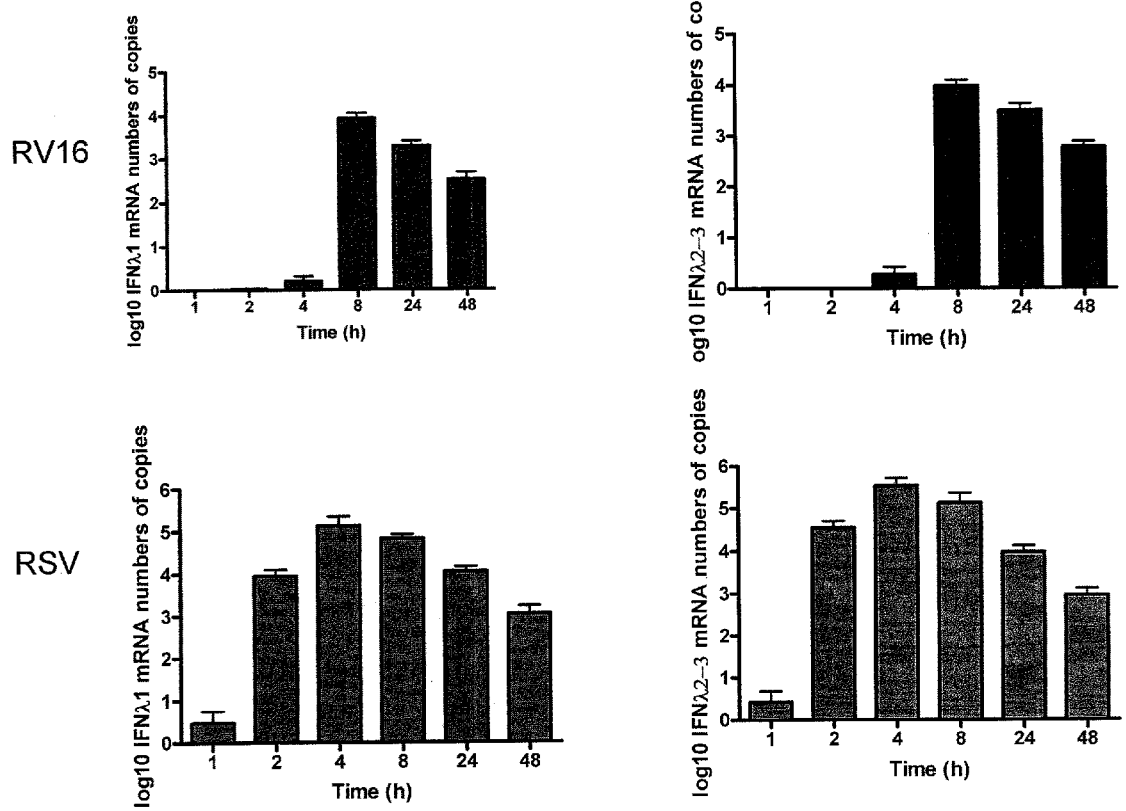

FIG. 10. Rhinovirus and RSV both strongly induce interferon lambda mRNA expression in the human bronchial epithelial cell line BEAS2B.

Figure 11:
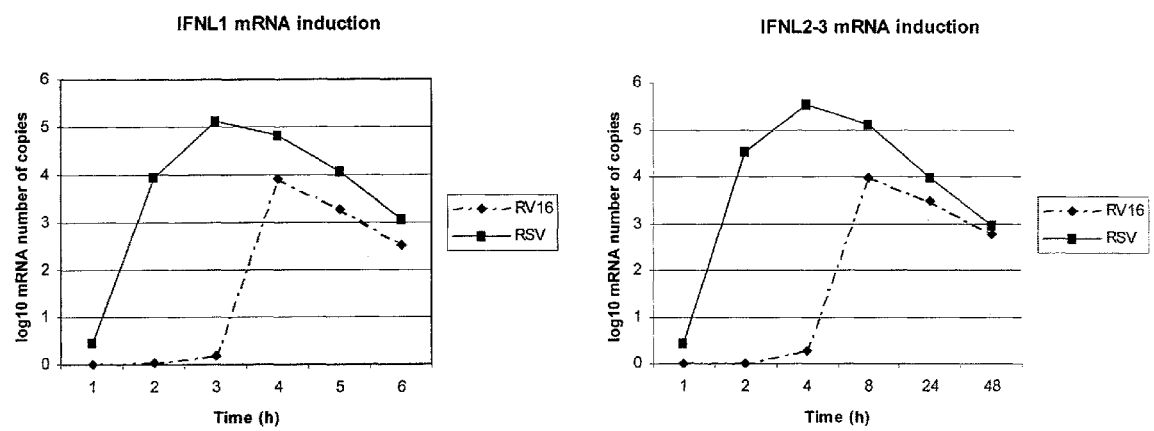

FIG. 11. Rhinovirus and RSV both strongly induce interferon lambda mRNA expression in the human bronchial epithelial cell line BEAS2B. Same data as FIG. 10.

Figure 12:
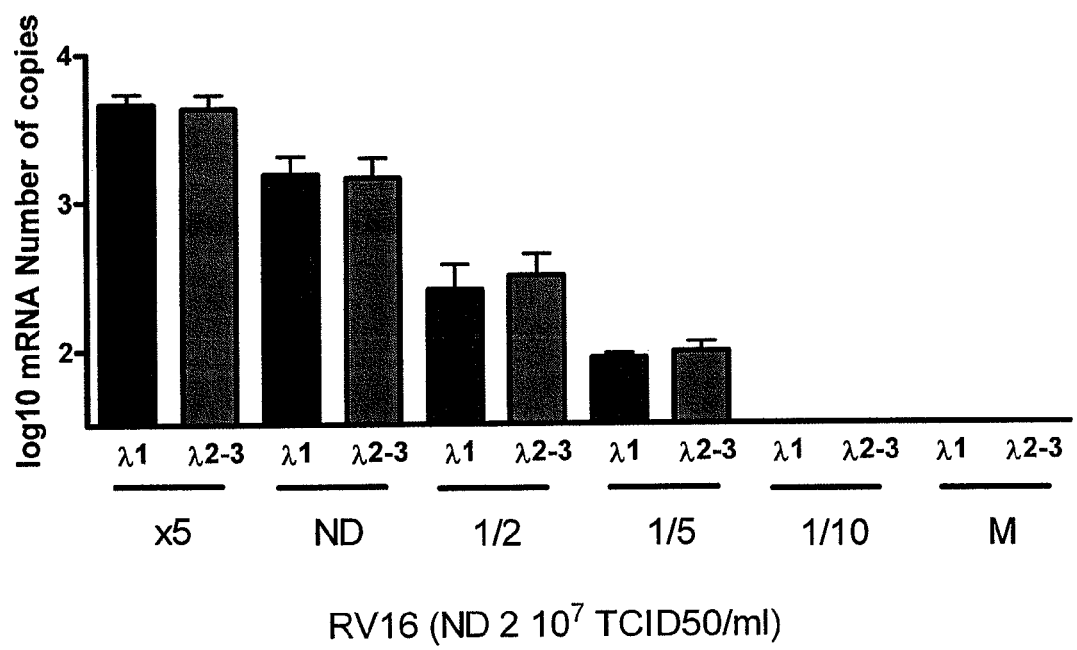

FIG. 12. A dose response as stated showing that rhinovirus induction of both IFNλ-1 and IFNλ-2/3 are dose responsive.

Figure 13:
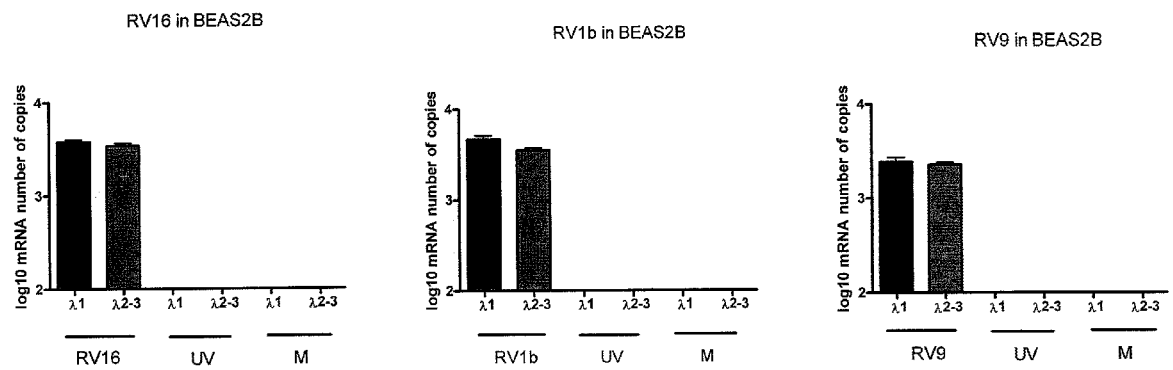

FIG. 13. Multiple serotypes of rhinovirus of both major and minor groups induce IFNλs. Since the induction is not observed with UV inactivated viruses, the induction is replication dependent.

Figure 14:
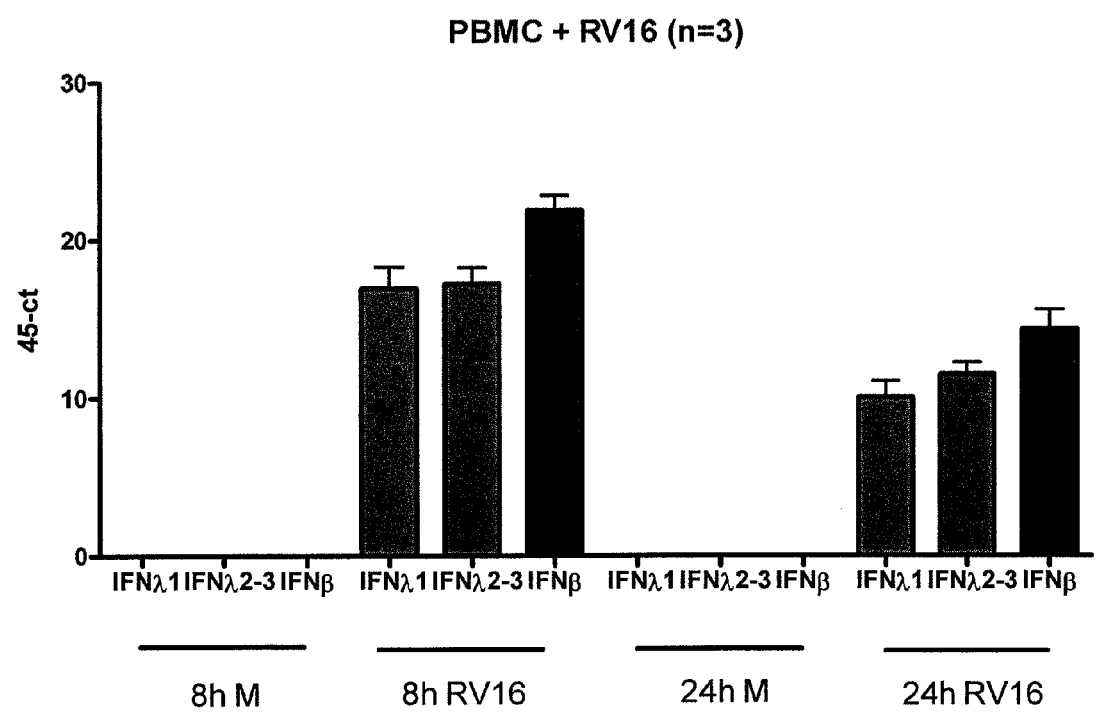

FIG. 14. IFNλs are induced from peripheral blood mononuclear cells from healthy volunteers in response to rhinovirus infection, induction peaking at 8 hours but still being significant at 24 hours.

Figure 15:
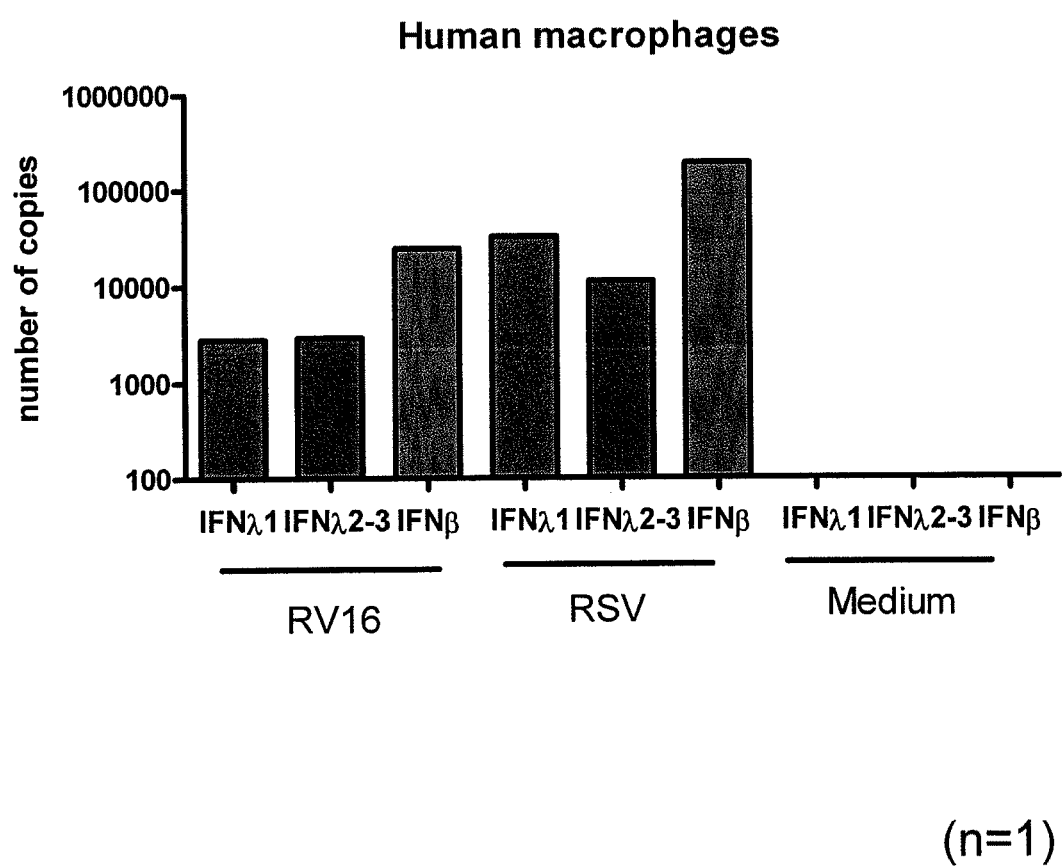

FIG. 15. IFNλs are induced from human macrophages by rhinovirus and RSV.

Figure 16:
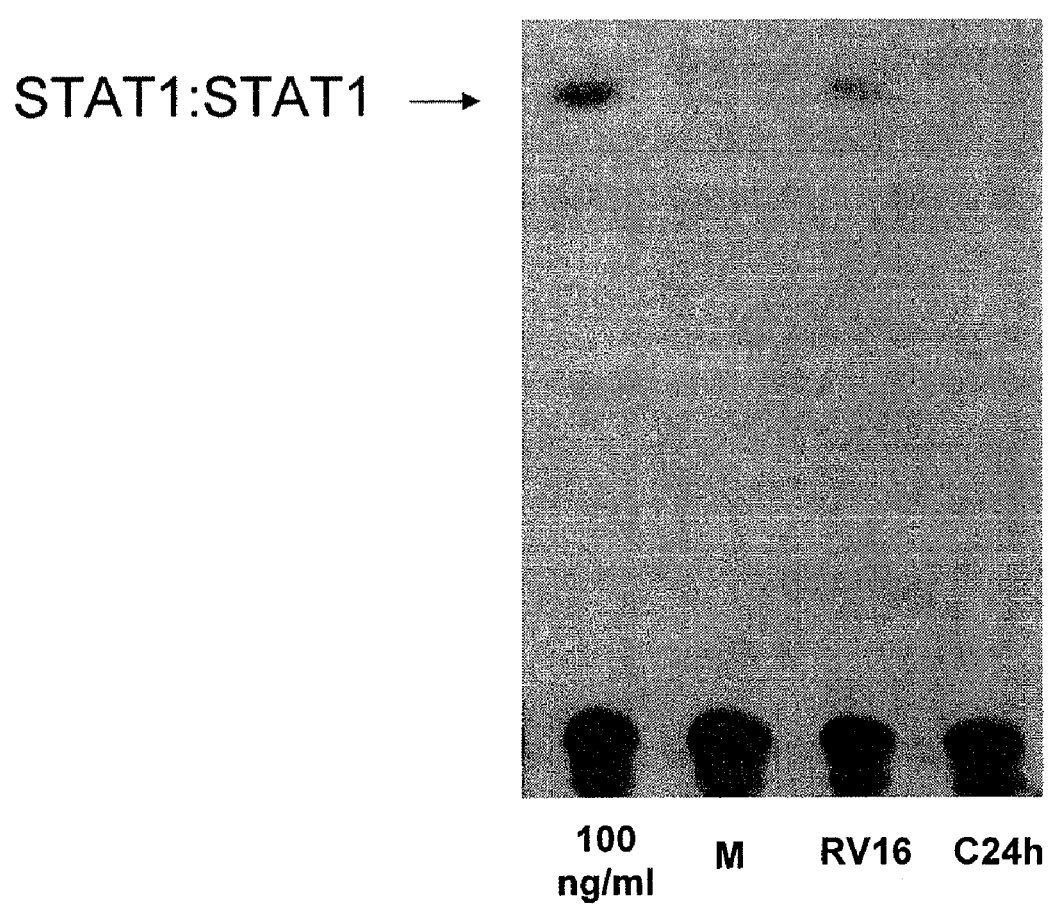

FIG. 16. Biological activity with activation of STAT1 by rhinovirus infection. In this experiment supernatants from rhinovirus infected BEAS2B cells were inoculated onto a reporter cell line expressing recombinant lambda receptor and STAT1 activation assessed by gel shift assay. Clear induction of STAT1 activation is observed with supernatants from virus infected bronchial epithelial cells but not control cells.

Figure 17:
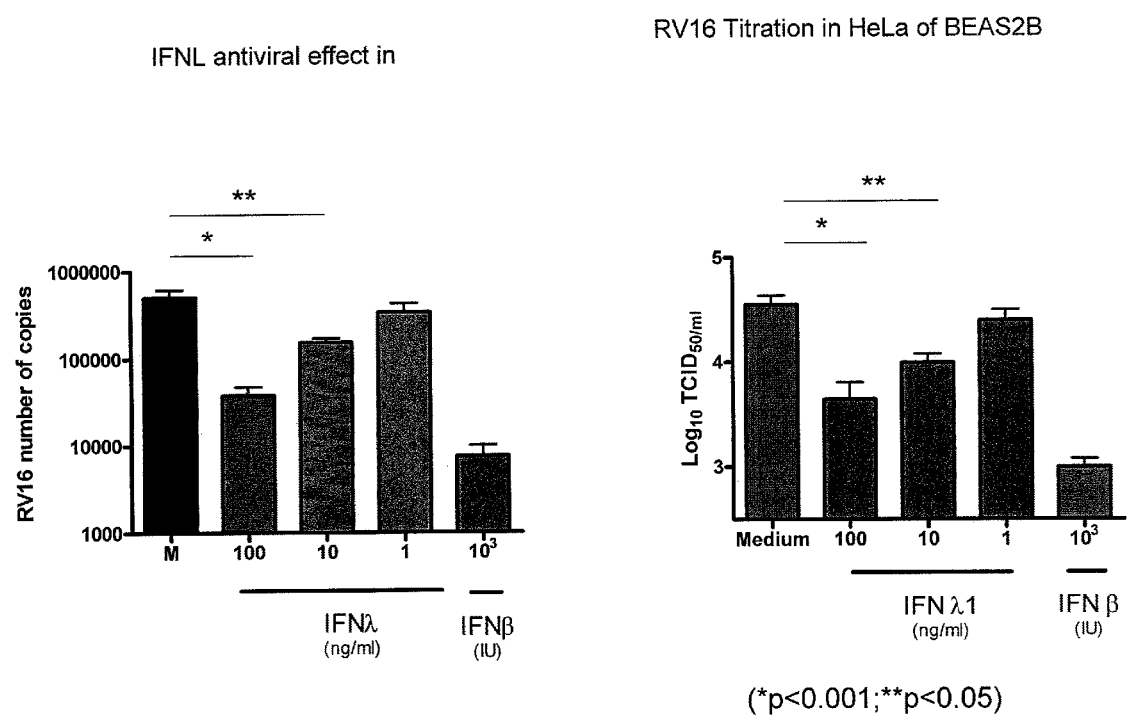

FIG. 17. IFNλ-1 has antiviral activity in a dose response manner, reducing rhinovirus 16 viral RNA expression in BEAS2B cells as well as reducing virus release in the supernatant of BEAS2B cells as measured by a HeLa cell titration assay. Viral RNA copy number was assessed by quantitative PCR.

Figure 18:
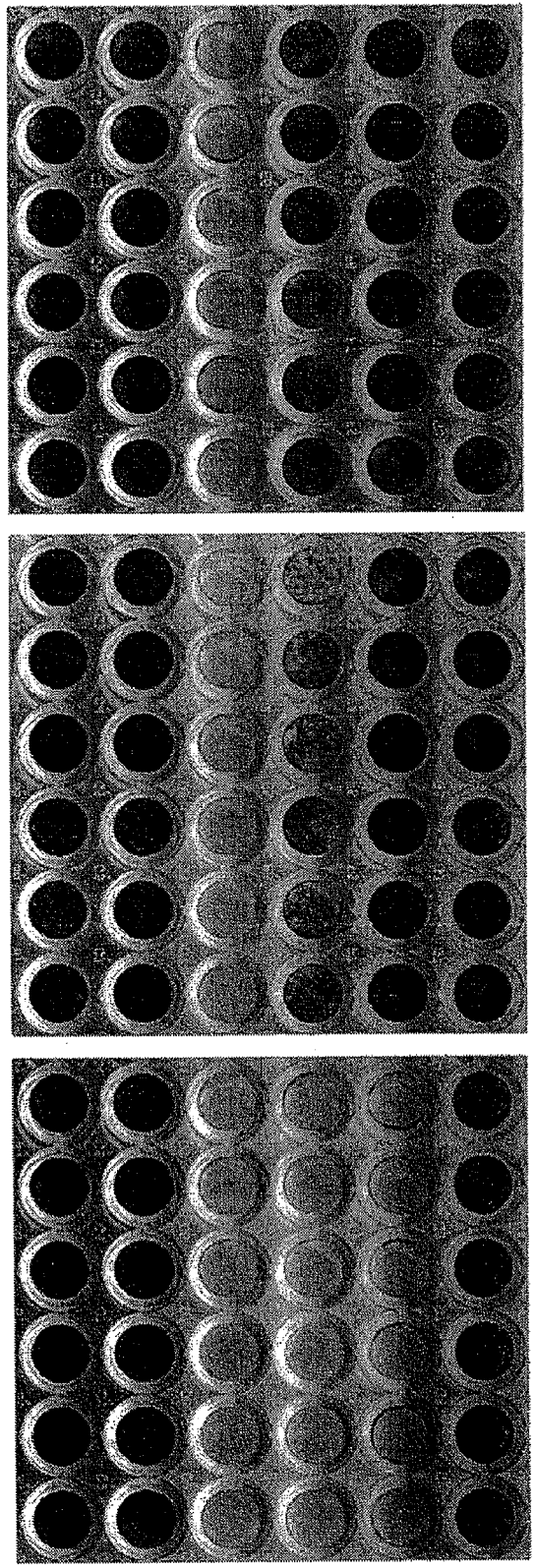

FIG. 18. Anti-viral activity in the HeLa cell titration assay showing that virus induced cytopathic effect is inhibited by IFNλ-1 to a similar degree as that observed with interferon β.

Figure 19:
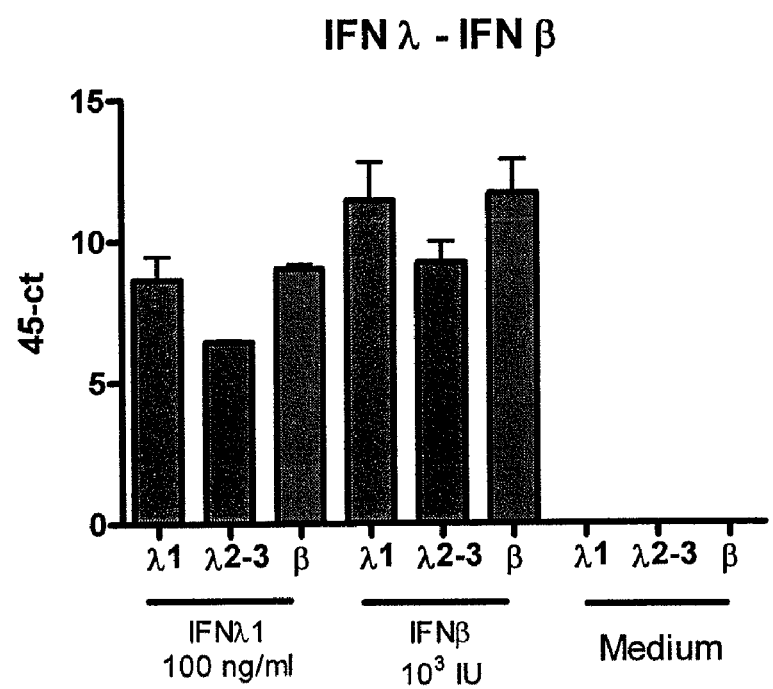

FIG. 19. IFNλ-1 induces itself as well as IFNλ2-3 and interferon β in BEAS2B cells. Similarly interferon β induces itself as well as inducing both IFNλ-1 and IFNλ 2-3. There is thus positive feedback between type 1 and type III interferon sub-types.

Figure 20:
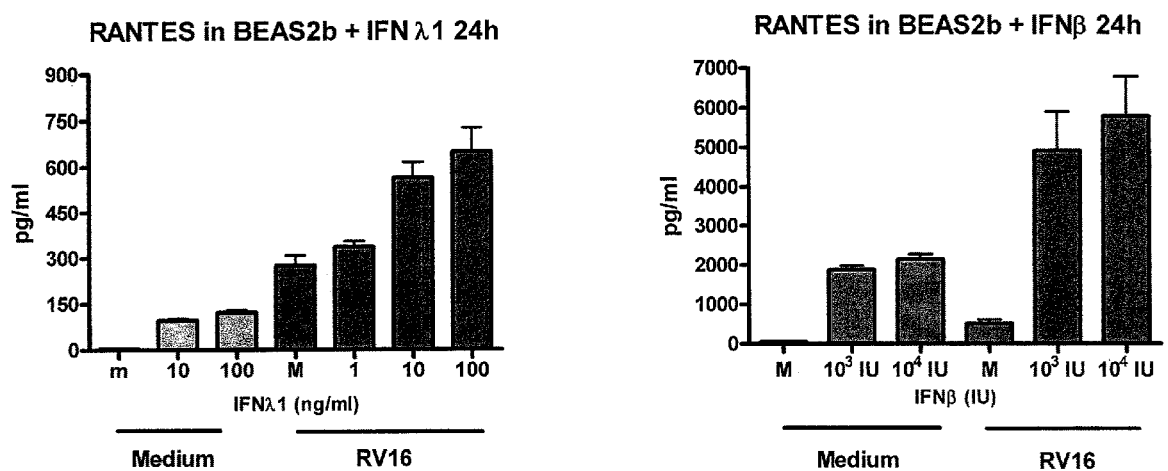

FIG. 20. IFNλs induce pro-inflammatory cytokines by themselves in a dose responsive manner and markedly enhance induction of pro-inflammatory cytokines in response to rhinovirus 16 expression, again in a dose responsive manner. These properties are observed in BEAS2B cells and indicate that IFNλs augment responses likely to recruit other inflammatory cells to virus infected epithelium. The right panel shows the same for interferon β.

Figure 21:
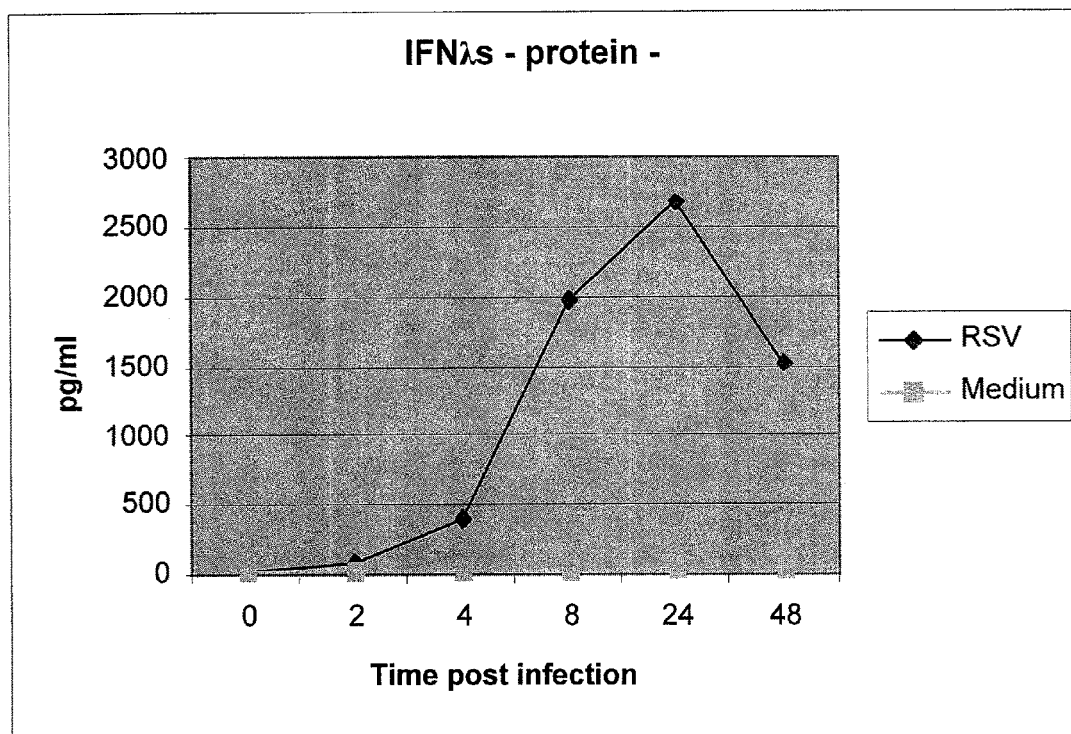

FIG. 21. RSV infection of BEAS2B cells results in increased IFNλ protein release into the supernatant in a time responsive manner, peaking at 24 hours.

Figure 22:
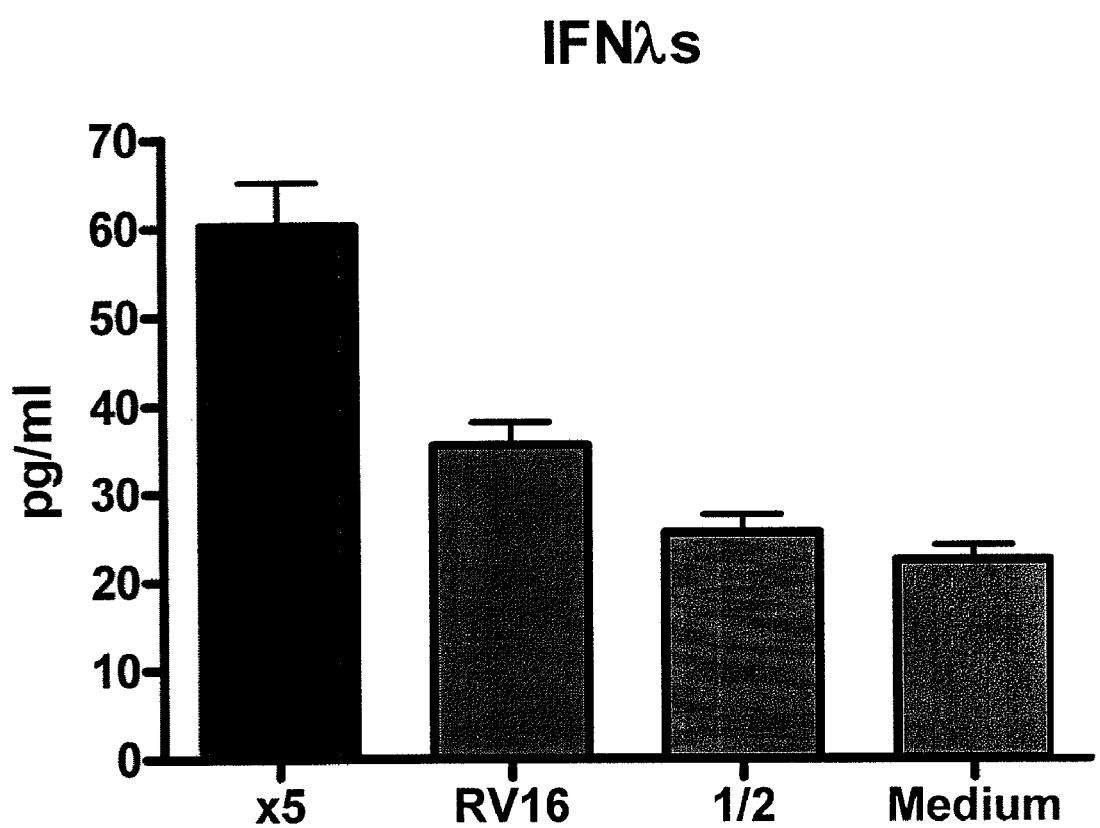

FIG. 22. Rhinovirus infection of BEAS2B cells also induces IFNλ protein release into the supernatants of BEAS2B cells in a dose responsive manner.

Figure 23:
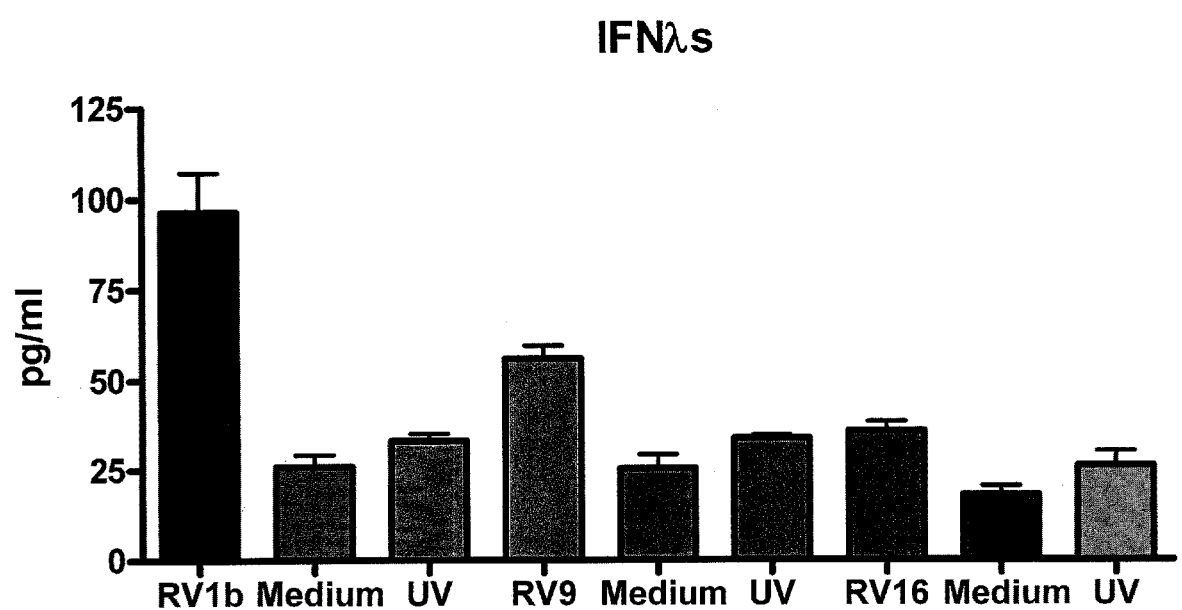

FIG. 23. Multiple serotypes of rhinovirus result in release of IFNλ proteins into supernatants of BEAS2B cells. Again, both major and minor serotypes and again in a replication dependent manner.

Figure 24:
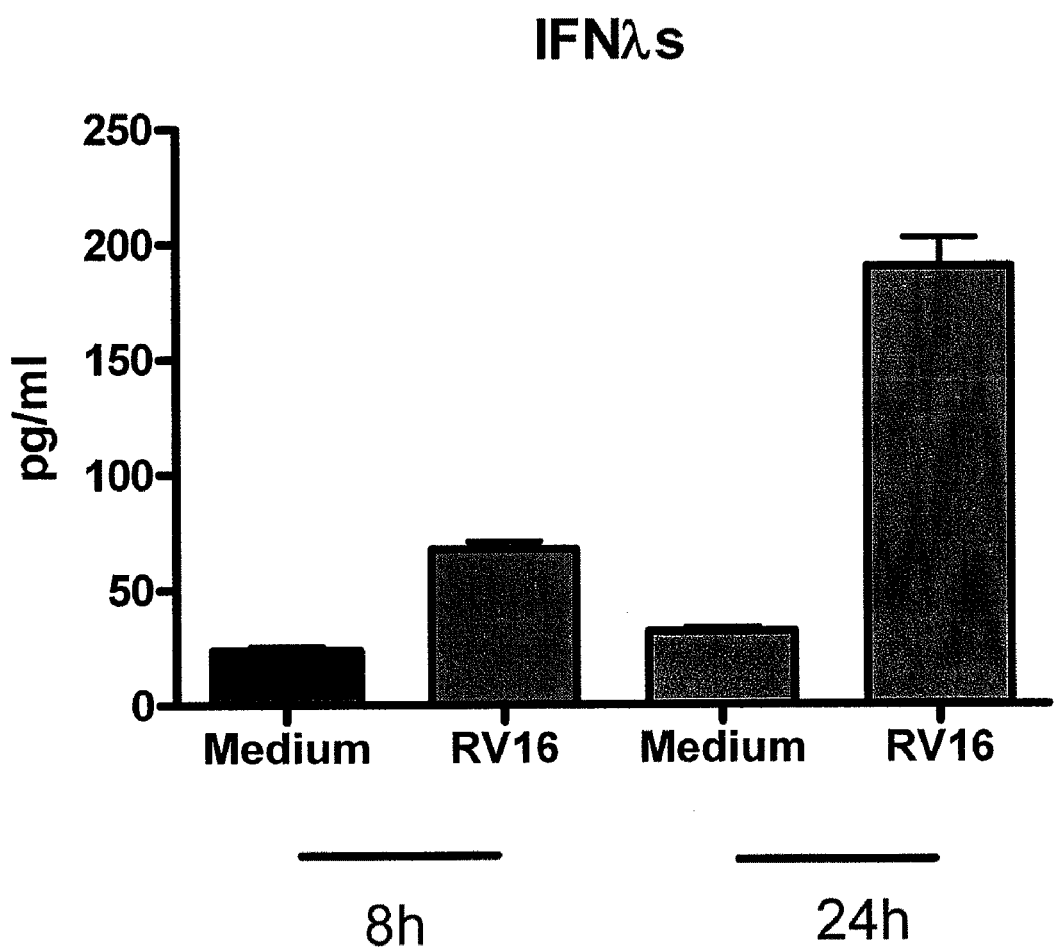

FIG. 24. Rhinovirus infection of peripheral blood mononuclear cells from healthy donors leads to an increase in IFNλ protein secretion into supernatants in a time dependent manner.

Figure 25:
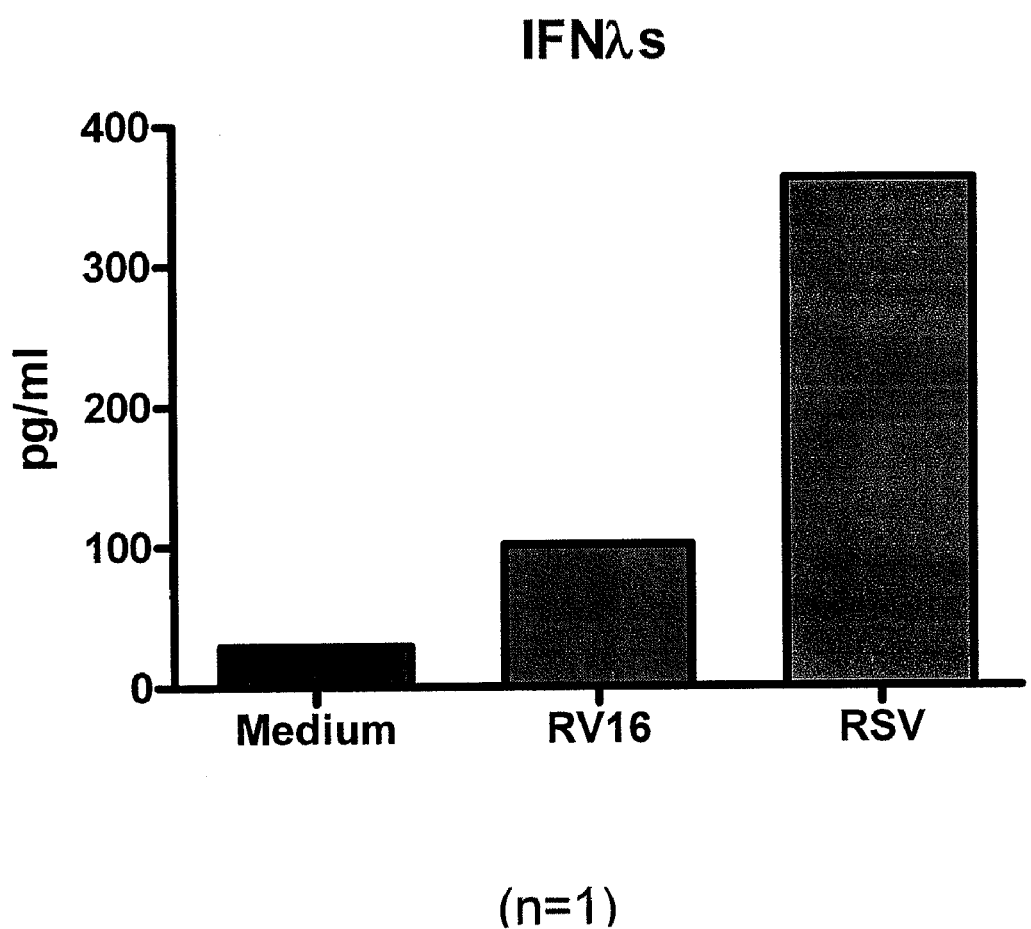

FIG. 25. Both rhinovirus and RSV infection of human macrophages results in IFNλ release into supernatants.

Figure 26:
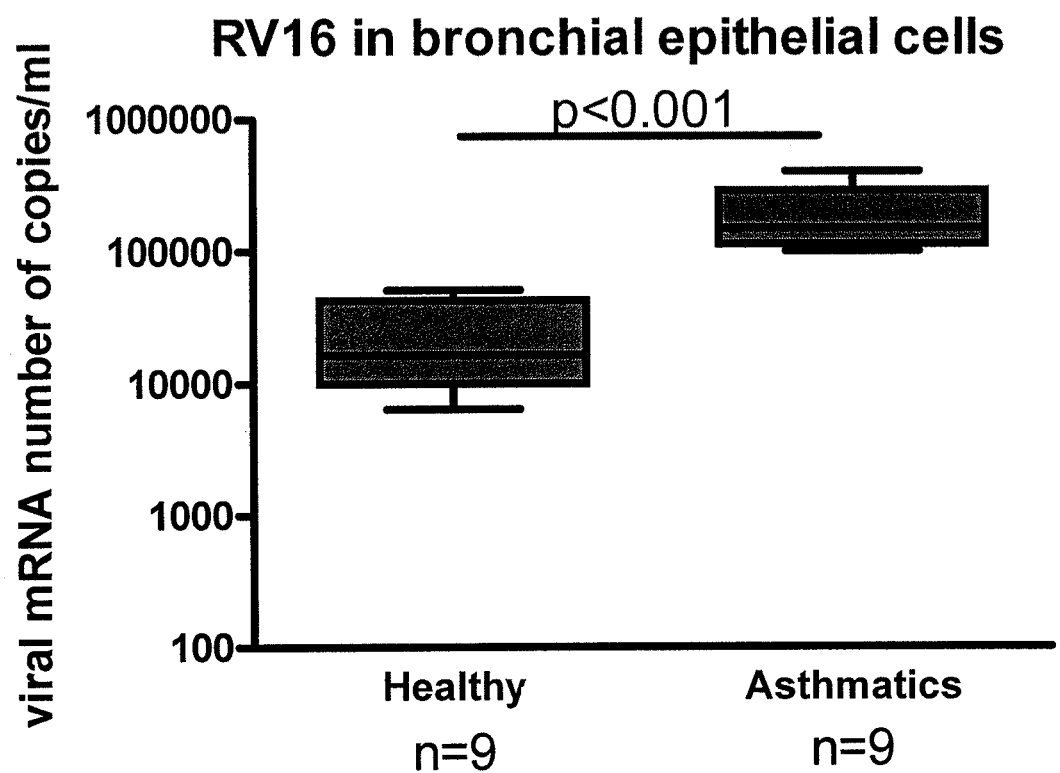

FIG. 26. Primary bronchial epithelial cells derived from asthmatic and healthy donors indicate that asthmatic epithelial cells have significantly increased virus replication compared to the normal epithelial cells. The difference in viral RNA copy number was assessed by quantitative PCR. Asthmatic epithelial cells produce more than one log greater viral RNA load than normal epithelial cells.

Figure 27:
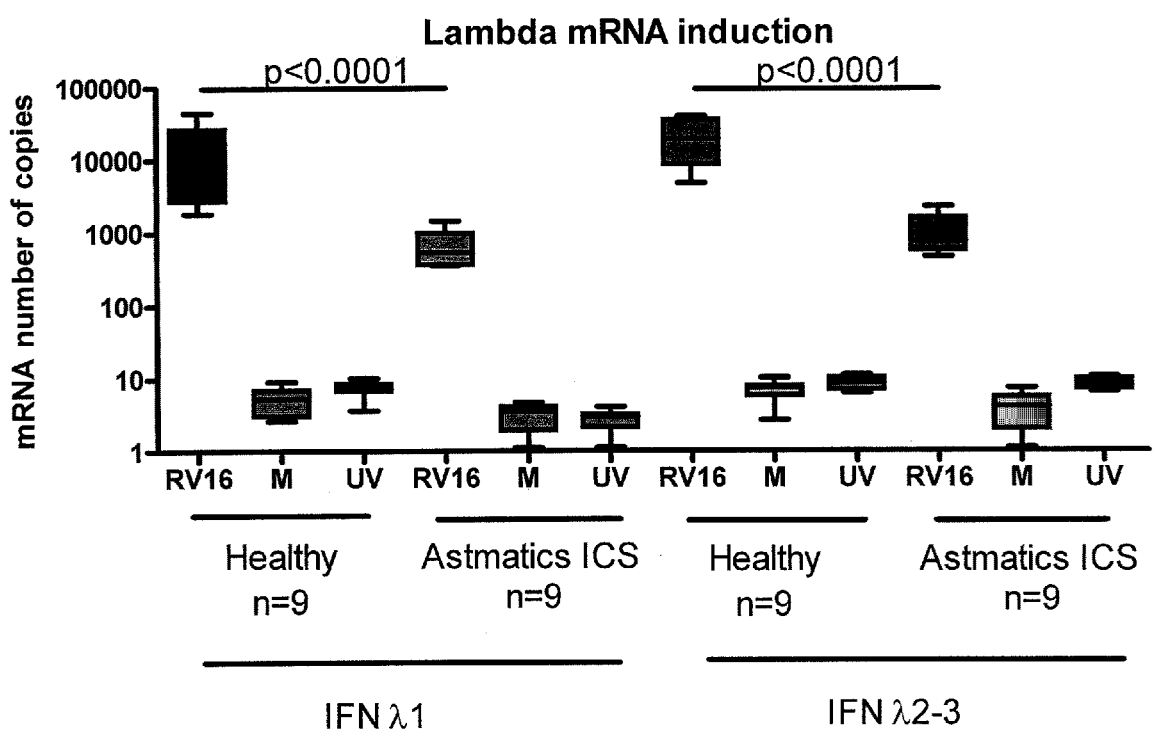

FIG. 27. IFNλ mRNA expression in response to rhinovirus infection in healthy and asthmatic epithelial cells is induced. However, induction is deficient in asthmatic relative to normal cells for IFNλs. IFNλ mRNA expression was quantified by quantitative PCR. Induction of IFNλ was replication dependent. Normal volunteers produced more than one log greater amounts of IFNλ mRNA than did asthmatic subjects.

Figure 28:
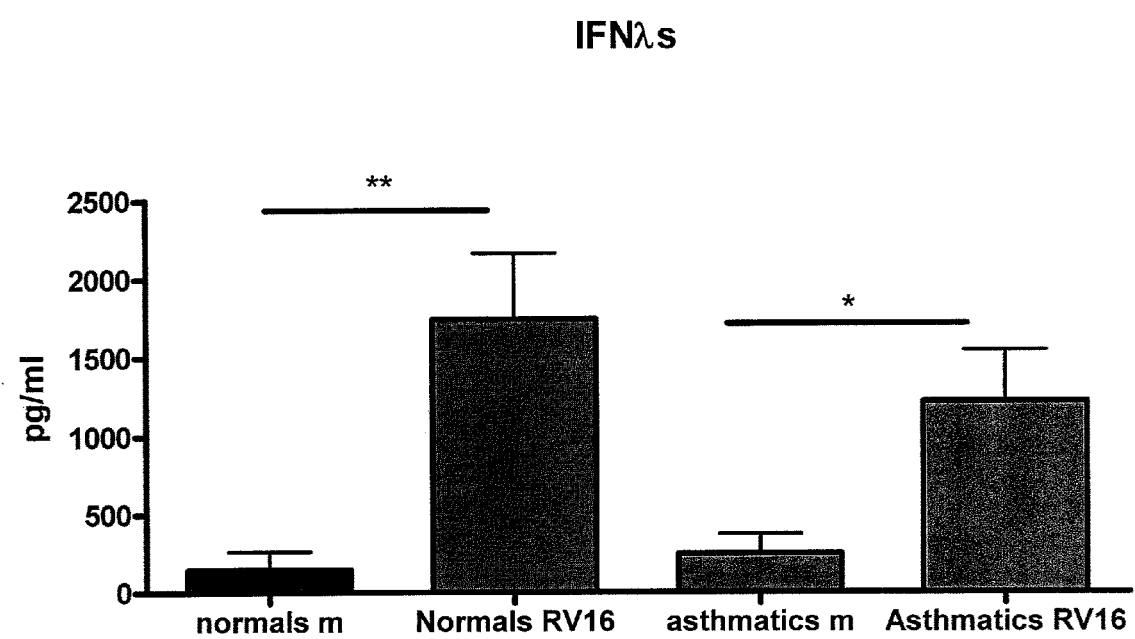

FIG. 28. IFNλ protein is induced by rhinovirus infection in both normal and asthmatic bronchial epithelial cells. Levels produced by normal epithelial cells once again are greater than those produced by asthmatic epithelial cells.

Figure 29:
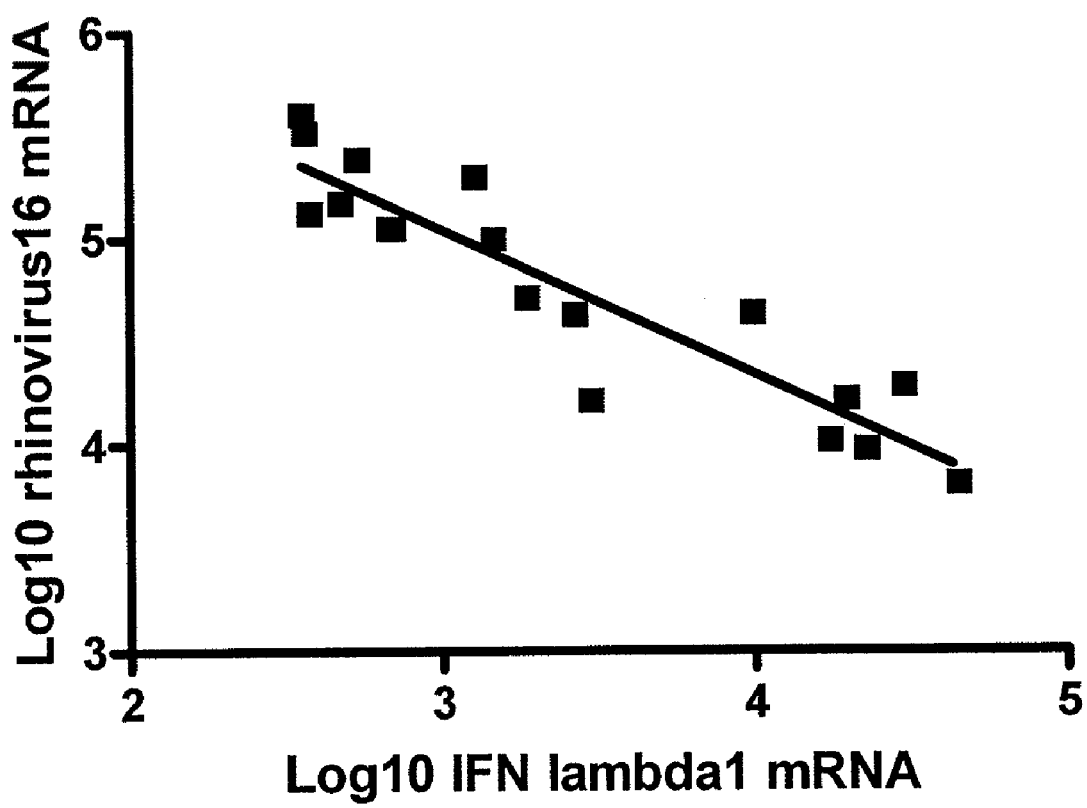

FIG. 29. IFNλ mRNA expression in primary human bronchial epithelial cells is strongly related to virus load. The greater the IFNα expression, the less virus replication occurred. This data indicates that IFNλ is associated with anti-viral activity in primary human bronchial epithelial cells.

Figure 30:
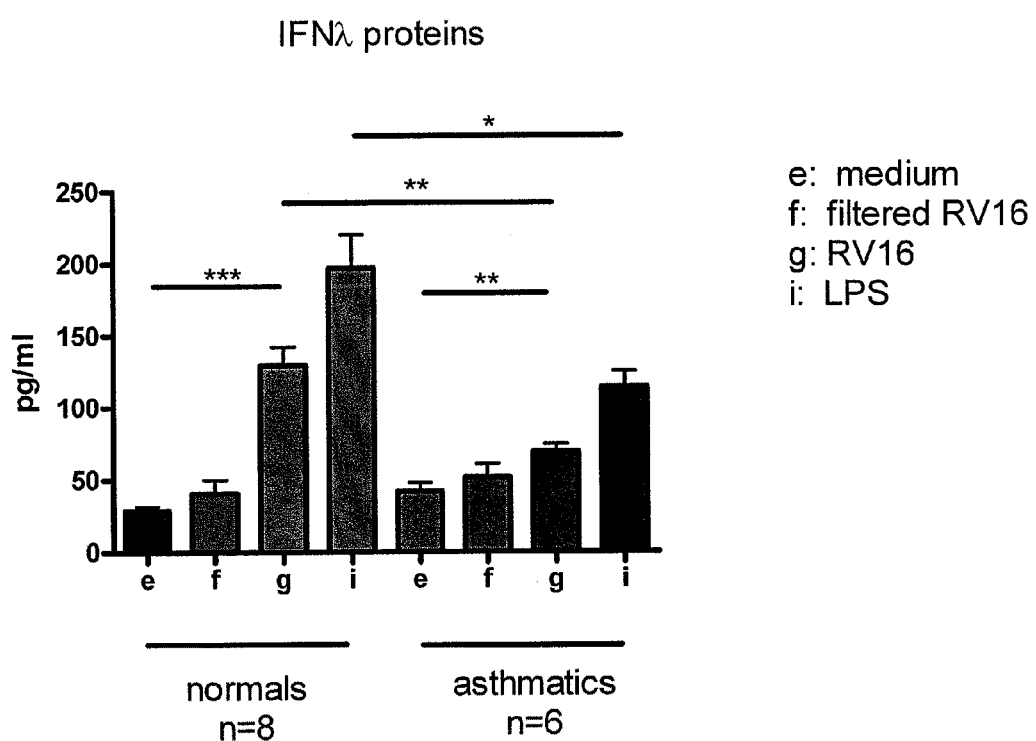

FIG. 30. IFNλ production in response to both rhinovirus infection and LPS stimulation of bronchoalveolar lavage cell pellets is deficient in asthmatics relative to normal individuals. Normally, more than 80% of bronchoalveolar lavage cells are macrophages. This data indicates that asthmatics are deficient in terms of IFNλ production from macrophages as well as the previous data from the epithelial cells.

Figure 31:
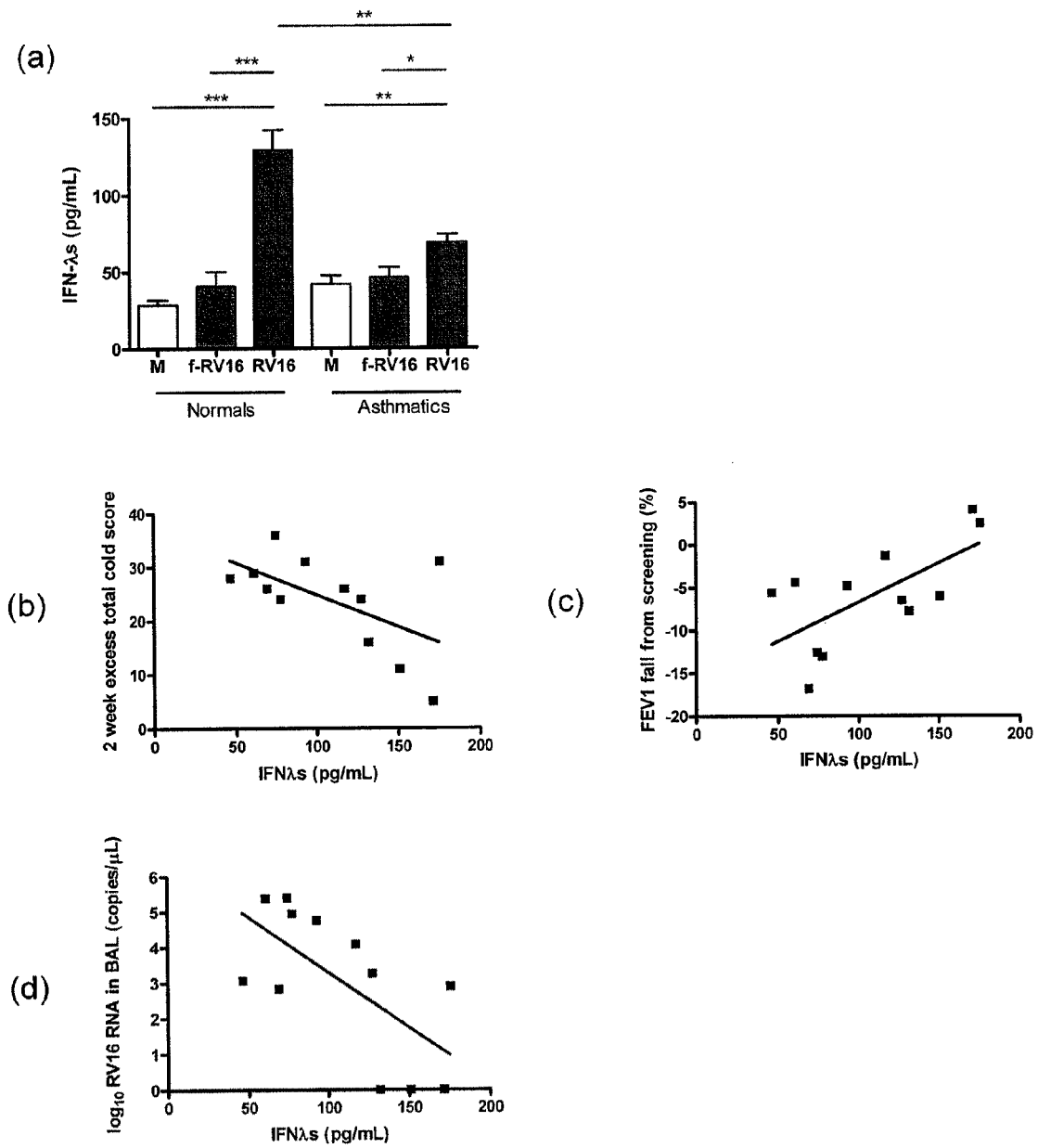

FIG. 31. IFNλ production from bronchoalveolar cell supernatants stimulated ex vivo with rhinovirus. IFNλ production in response to rhinovirus infection of bronchoalveolar lavage cell pellets is strongly related to severity of clinical colds, severity of reductions in lung function and to virus load in asthmatic and normal subjects experimentally infected with rhinovirus in vivo. In these experiments IFNλ production from bronchoalveolar lavage cell pellets in response to rhinovirus infection in vitro was determined at baseline, and subjects were then infected with rhinovirus in vivo 2 weeks later. During this in vivo infection, cold symptoms, reductions in lung function and lower airway virus load were all assessed to monitor severity of clinical illness during an in vivo infection. IFNλ production at baseline was strongly related to severity of colds, severity of asthma exacerbation as determined by reductions in lung function, and to bronchoalveolar lavage virus load during the in vivo infection. These data clearly indicate that IFNλ production is a major determinant of severity of clinical illness during respiratory virus infections in vivo, and indicate that IFNλ administration should reduce symptoms, virus load and severity of reductions in lung function during respiratory virus infection in asthmatic subjects.

Figure 32:
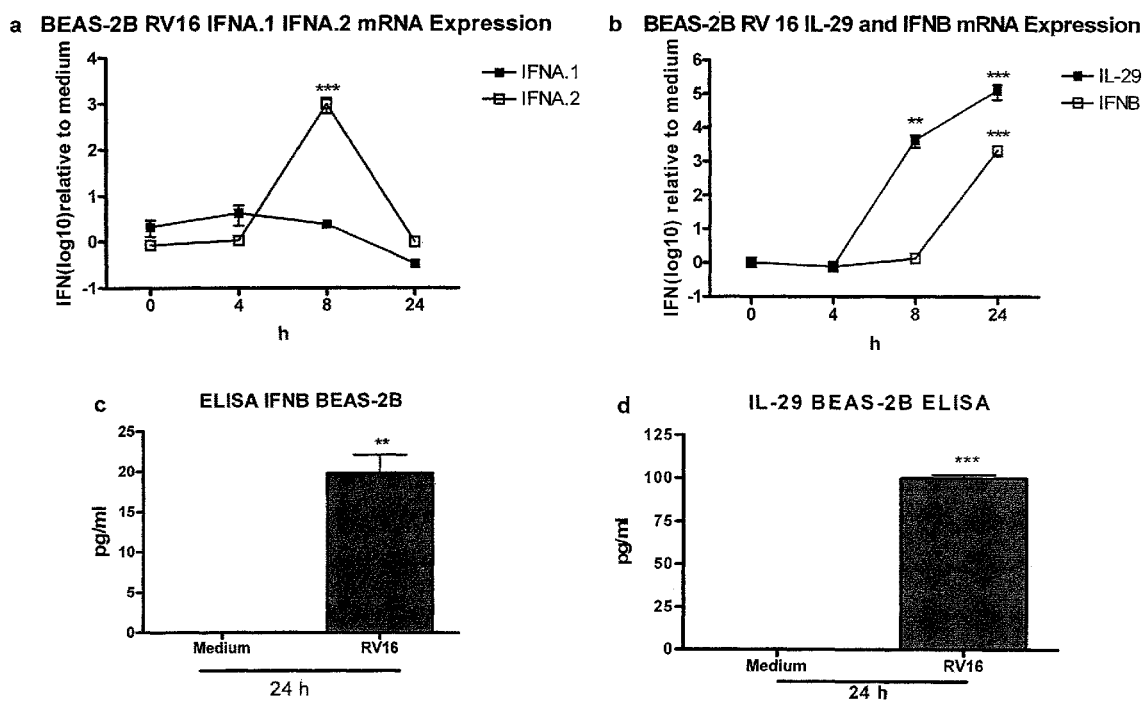

FIG. 32. Time course of induction of type I and type III interferons in response to rhinovirus 16 infection in BEAS-2B cells.
    (a) The mRNA expression of different alpha interferon subtypes was studied by Taqman PCR. For detection of various alpha interferon subtypes two pairs of Taqman PCR primers and probes were selected. First primer and probe set detects subtypes 1, 6 and 13, second primer and probe set detects subtypes 4, 5, 8, 10, 14, 17, 21. The expression of type 1 interferons was detected by first primer pair –IFNA. 1, but no significant induction of mRNA expression of these type 1 interferons by rhinovirus 16 was found. Using the second primer pair –IFNA.2 a statistically significant increase of type 1 interferon mRNA expression in comparison to medium was observed, but only at 8 hours from infection (p<0.001).

(b) The expression of IL-29 and beta interferon mRNA was studied by Taqman PCR in the same experiments. The induction of IL-29 mRNA expression by rhinovirus 16 was statistically significant increased at 8 hour time point and we detected even higher induction by 24 hours (p<0.001). IFN beta mRNA expression was also induced by rhinovirus 16 at 24 hours (p<0.001). Thus IFNλ mRNA production occurred earlier than beta, was more sustained than alpha and was induced to a greater degree than either alpha or beta IFN production.

(c) The production of interferon-beta was measured by ELISA in the same experiments. By 24 hours statistically significant induction of interferon-beta protein was detected in rhinovirus 16 infected BEAS-2B cells (p<0.01).

(d) The production of IL-29 was measured by ELISA in the same experiments. By 24 hours statistically significant induction of IL-29 protein was detected in rhinovirus 16 infected BEAS-2B cells (p<0.001). Thus consistent with the mRNA data, production of IFNλ protein was 5 fold greater than production of beta IFN. Alpha IFN proteins were undetectable in these experiments.

Figure 33:
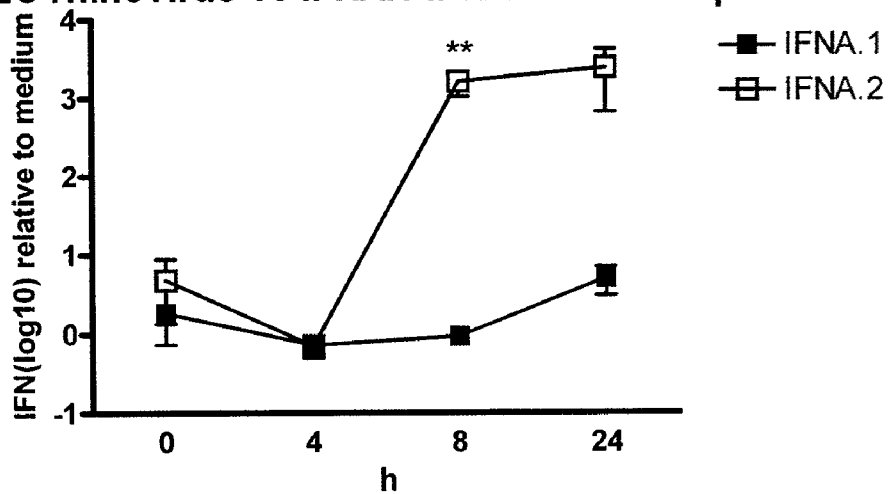
Figure 33:
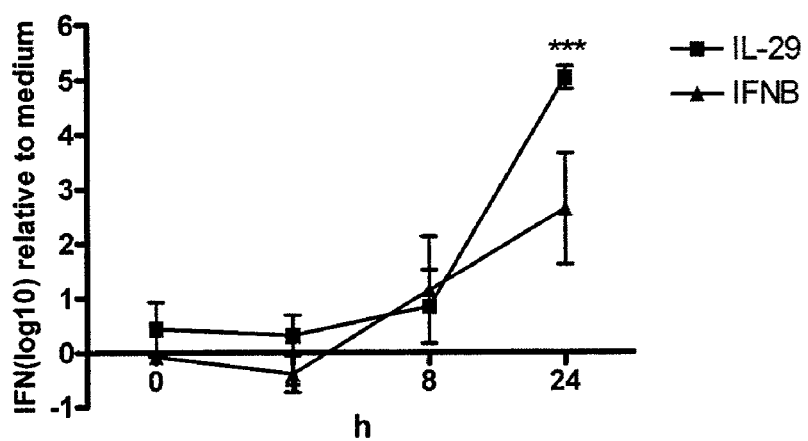

FIG. 33. Time course of IFN production in response to rhinovirus 16 infection in primary human bronchial epithelial cells (a) The mRNA expression of different alpha interferon types was assessed during a rhinovirus 16 time course at 0, 4, 8 and 24-hour time points in human bronchial epithelial cells by Taqman PCR. Alpha-interferons detected by IFNA.1 primer pair were not induced by rhinovirus 16 while those detected by the IFNA.2 were significantly induced (p<0.01) over medium at 8 hours but at 24 hours there was no statistically significant induction.

(b) The expression of IL-29 and beta interferon mRNA in human bronchial epithelial cells infected by rhinovirus 16 was studied by Taqman PCR in the same experiments. IL-29 mRNA expression was significantly induced at 24 hours (p<0.001). Interferon-beta demonstrated no significant induction at any time point.

Figure 34:
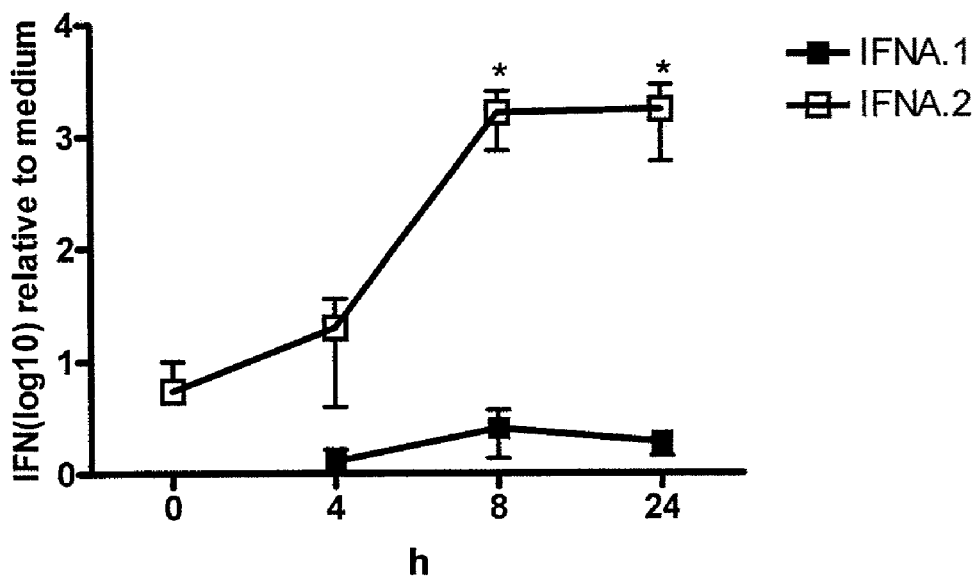
Figure 34:
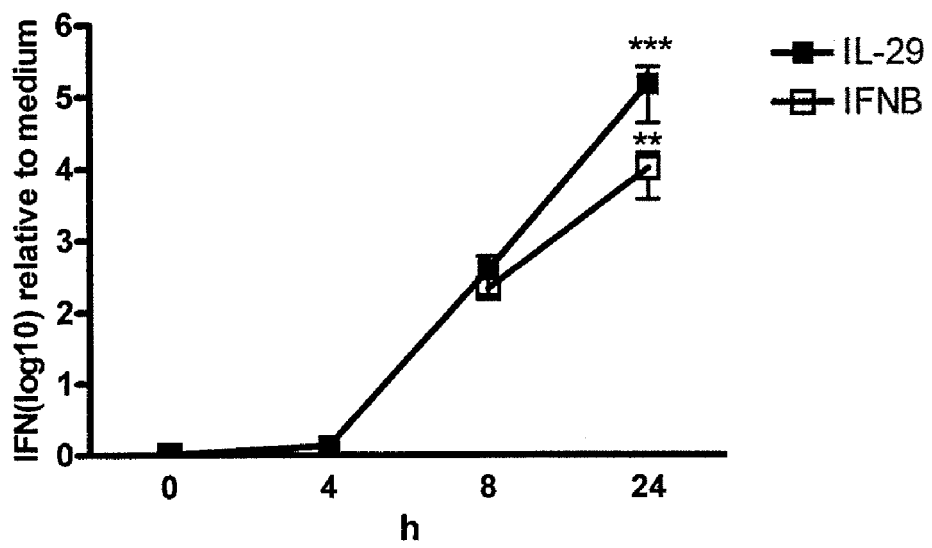

FIG. 34. Time course of IFN production in response to rhinovirus 1B infection in human bronchial epithelial cells.

IFN alpha, IFN beta and IL-29 mRNA expression was also assessed during a rhinovirus 1B time course at 0, 4, 8 and 24-hour time points by Taqman PCR.

(a) Alpha-interferons detected by IFNA. 1 primer pair were not induced by rhinovirus 16. mRNA of alpha-interferons detected by second primer pair IFNA.2 were induced by rhinovirus 1B at 8 and 24 hours (p<0.05).

(b) With IL-29 a very high level of induction (2 logs greater than those detected by the IFNA.2 primer pair) was detected at 24 hours (p<0.001). Induction of interferon-beta mRNA was also detected at 24 hours (p<0.01), though this induction was 1 log less than that observed for IL-29.

Figure 35:
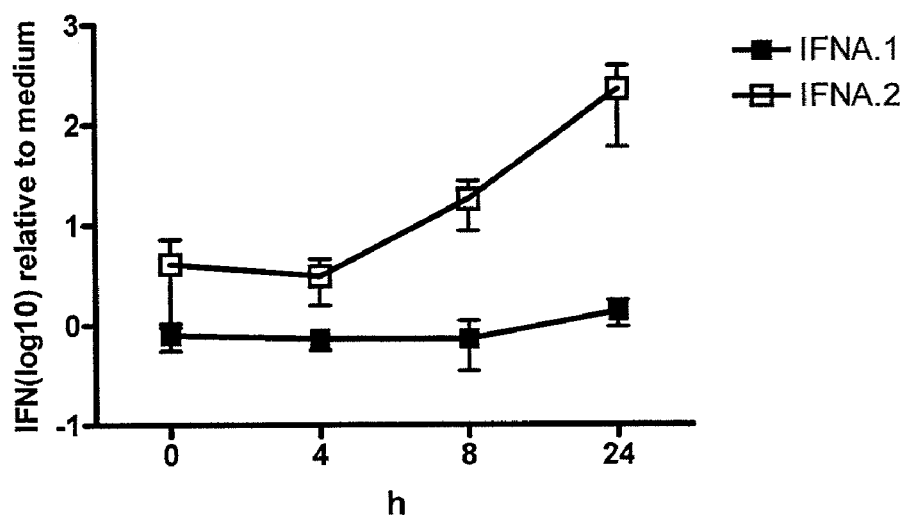
Figure 35:
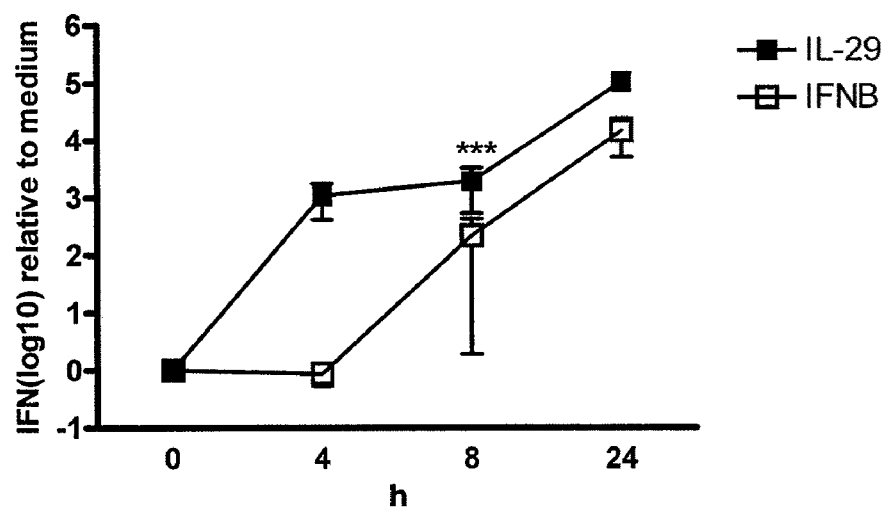

FIG. 35. Time course of IFN production in response to influenza virus infection in human bronchial epithelial cells.

(a) The expression of different alpha interferon types mRNA was assessed during a influenza virus time course at 0, 4, 8 and 24-hour time points in human bronchial epithelial cells by Taqman PCR. Neither alpha-interferons detected by the IFNA. 1 primer pair nor those detected by the IFNA.2 primer pair were significantly induced by influenza virus at any time point.

(b) The expression of IL-29 and beta-interferon mRNA was studied in human bronchial epithelial cells infected by influenza virus by Taqman PCR in the same experiments. IL-29 was significantly induced by influenza virus at 8 hours after infection (p<0.001) and increased further at 24 hrs. Interferon-beta mRNA induction was not significantly induced at any time point, though increases were observed at 8 and 24 hrs. IL-29 mRNA expression was greater than that of alpha and beta IFNs at all time points.

BRIEF DESCRIPTION OF THE SEQUENCE LISTING

SEQ ID NO: 1 shows the nucleotide sequence of human IFNβ-1a.

SEQ ID NO: 2 shows the amino acid sequence of human IFNβ-1a.

SEQ ID NO: 3 shows the nucleotide sequence of human IFNβ-1b.

SEQ ID NO: 4 shows the amino acid sequence of human IFNβ-1b. IFNβ-1b is identical to human IFNβ-1a except for replacement of the cysteine at residue 17 with serine.

SEQ.ID.NO: 5 shows the amino acid sequence of IFNλ-1
SEQ.ID.NO: 6 shows the amino acid sequence of IFNλ-2
SEQ.ID.NO: 7 shows the amino acid sequence of IFNλ-3

The remaining SEQ ID NOs relate to oligonucleotide probes and primers referred to in the Examples.

As hereinbefore indicated, the present invention relates to new therapeutic uses for IFN-β. In particular, it relates, for example, to therapeutic use of IFN-β by airway delivery to promote apoptosis in bronchial epithelial cells of asthmatic patients infected with rhinovirus. The invention as presented also extends to airway delivery of IFN-β to treat rhinovirus-induced exacerbation of COPD.

Definition of IFN-β

The term IFN-β as used herein will be understood to refer to any form or analog of IFN-β that retains the biological activity of native IFN-β and preferably retains the activity of IFN-β that is present in the lung and, in particular, the bronchial epithelium.

The IFN-α may be identical to or comprise the sequence of human IFNβ-1a (SEQ ID NO: 2) or human IFNβ-1b (SEQ ID NO: 4). IFN-β also refers to a variant polypeptide having an amino acid sequence which varies from that of SEQ ID NO: 2 or 4. Alternatively, IFN-β may be chemically-modified.

A variant of IFN-β may be a naturally occurring variant, for example a variant which is expressed by a non-human species. Also, variants of IFN-β include sequences which vary from SEQ ID NO: 2 or 4 but are not necessarily naturally occurring. Over the entire length of the amino acid sequence of SEQ ID NO: 2 or 4, a variant will preferably be at least 80% homologous to that sequence based on amino acid identity. More preferably, the polypeptide is at least 85% or 90% and more preferably at least 95%, 97% or 99% homologous based on amino acid identity to the amino acid sequence of SEQ ID NO: 2 or 4 over the entire sequence. There may be at least 80%, for example at least 85%, 90% or 95%, amino acid identity over a stretch of 40 or more, for example 60, 80, 100, 120, 140 or 160 or more, contiguous amino acids ("hard homology").

Homology may be determined using any method known in the art. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Amino acid substitutions may be made to the amino acid sequence of SEQ ID NO: 1 or 2, for example from 1, 2, 3, 4 or 5 to 10, 20 or 30 substitutions. Conservative substitutions may be made, for example, according to Table 1. Amino acids in the same block in the second column and preferably in the same line in the third column may be substituted for each other:

TABLE 1

Conservative amino acid substitutions

| NON-AROMATIC | Non-polar | G A P |
| | | I L V |
| | Polar - uncharged | C S T M |
| | | N Q |
| | Polar - charged | D E |
| | | H K R |
| AROMATIC | | H F W Y |

One or more amino acid residues of the amino acid sequence of SEQ ID NO: 1 or 2 may alternatively or additionally be deleted. From 1, 2, 3, 4 or 5 to 10, 20 or 30 residues may be deleted, or more.

IFN-β also includes fragments of the above-mentioned sequences. Such fragments retain IFN-β activity. Fragments may be at least from 120 or 140 amino acids in length. Such fragments may be used to produce chimeric agents as described in more detail below.

IFN-β includes chimeric proteins comprising fragments or portions of SEQ ID NO: 2 or 4. One or more amino acids may be alternatively or additionally added to the polypeptides described above. An extension may be provided at the N-terminus or C-terminus of the amino acid sequence of SEQ ID NO: 2 or 4 or polypeptide variant or fragment thereof. The extension may be quite short, for example from 1 to 10 amino acids in length. Alternatively, the extension may be longer. A carrier protein may be fused to an amino acid sequence described above. A fusion protein incorporating one of the polypeptides described above can thus be used in the invention.

IFN-β also includes SEQ ID NO: 2 or 4 or variants thereof that have been chemically-modified. A number of side chain modifications are known in the art and may be made to the side chains of the proteins or peptides discussed above. Such modifications include, for example, glycosylation, phosphorylation, modifications of amino acids by reductive alkylation by reaction with an aldehyde followed by reduction with $NaBH_4$, amidination with methylacetimidate or acylation with acetic anhydride. The modification is preferably glycosylation.

The IFN-β may be made synthetically or by recombinant means using methods known in the art. The amino acid sequence of proteins and polypeptides may be modified to include non-naturally occurring amino acids or to increase the stability of the compound. When the proteins or peptides are produced by synthetic means, such amino acids may be introduced during production. The proteins or peptides may also be modified following either synthetic or recombinant production.

The IFN-β may also be produced using D-amino acids. In such cases the amino acids will be linked in reverse sequence in the C to N orientation. This is conventional in the art for producing such proteins or peptides.

The IFN-β may be produced in a cell by in situ expression of the polypeptide from a recombinant expression vector. The expression vector optionally carries an inducible promoter to control the expression of the polypeptide. The IFN-β or analog thereof may be produced in large scale following purification by any protein liquid chromatography system after recombinant expression. Preferred protein liquid chromatography systems include FPLC, AKTA systems, the Bio-Cad system, the Bio-Rad BioLogic system and the Gilson HPLC system.

Commercially available forms of IFN-β or analogs thereof may be used in the invention. Examples include Betaseron® and Avonex®.

Agents that Increase IFN-β Expression

The invention may also involve using an agent that increases endogenous expression of IFN-β in the lung or preferably the bronchial epithelium. The agents may act directly on the promoter or other regulatory sequences of the IFN-β gene. Such agents may act to reduce the constitutive silencing of the IFN-β promoter. Alternatively, the agent may stimulate cells to produce endogenous IFN-β by acting at receptors at the cell surface. Agents that increases endogenous expression of IFN-β of interest in relation to the present invention include, but are not limited to, poly(inosinic acid)-poly(cytidylic acid) (poly(IC)) and the ACE inhibitor perindopril.

Polynucleotides

The invention may also involve using a polynucleotide which is capable of expressing IFN-β or an agent that increases endogenous expression of IFN-β in lung airways. Such a polynucleotide may preferably be in the form of a vector capable of directing expression of IFN-β or an agent that induces IFN-β in the bronchial epithelium. The resulting IFN-β or agent may then have a therapeutic effect ("gene therapy"). The polynucleotide may encode any of the forms of IFN-β discussed above including the variants, fragments and chimeric proteins thereof.

The polynucleotide encoding IFN-β may comprise the human sequence (SEQ ID NO: 1 or 3) or a naturally occurring sequence variant, for example a variant which is expressed by a non-human species. Also, a polynucleotide encoding IFN-β include sequences which vary from SEQ ID NO: 1 or 3 but are not necessarily naturally occurring. Over the entire length of the amino acid sequence of SEQ ID NO: 1 or 3, a variant will preferably be at least 80% homologous to that sequence based on nucleotide identity. More preferably, the polynucleotide is at least 85% or 90% and more preferably at least 95%, 97% or 99% homologous based on nucleotide identity to the nucleotide of SEQ ID NO: 1 or 3 over the entire sequence. There may be at least 80%, for example at least 85%, 90% or 95%, nucleotide identity over a stretch of 40 or more, for example 60, 80, 100, 120, 140 or 160 or more, contiguous nucleotides ("hard homology"). Homology may be determined as discussed above.

The polynucleotides may comprise DNA or RNA but preferably comprise DNA. They may also be polynucleotides which include within them synthetic or modified nucleotides. A number of different types of modification to polynucleotides are known in the art. These include methylphosphate and phosphorothioate backbones, addition of acridine or polylysine chains at the 3' and/or 5' ends of the molecule. For the purposes of the present invention, it is to be understood that the polynucleotides described herein may be modified by any method available in the art.

Polynucleotides such as a DNA polynucleotide may be produced recombinantly, synthetically, or by any means available to those of skill in the art. They may also be cloned by standard techniques. The polynucleotides are typically provided in isolated and/or purified form.

Polynucleotides will generally be produced using recombinant means, for example using PCR (polymerase chain reaction) cloning techniques. This will involve making a pair of primers (e.g. of about 15-30 nucleotides) to a region of the required gene which it is desired to clone, bringing the primers into contact with DNA obtained from a suitable cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Although in general the techniques mentioned herein are well known in the art, reference may be made in particular to Sambrook et al, 1989.

As hereinbefore indicated, preferably the polynucleotide is used in an expression vector wherein it is operably linked to a control sequence which is capable of providing for the expression of the coding sequence in the airways of human lung.

Expression vectors for use in accordance with the invention may be any type of vector conventionally employed for gene therapy. It may be a plasmid expression vector administered as naked DNA or complexed with one or more cationic amphiphiles, e.g one or more cationic lipids, e.g. in the form of DNA/liposomes. A viral vector may alternatively be employed. Vectors for expression of therapeutic proteins in the airways of human lung have previously been described. For example, Published International Application WO 01/91800 (Isis Innovation Limited) describes for such purpose expression vectors including the human ubiquitin C promoter or functional analogues thereof. The human ubiquitin C promoter has been shown to be capable of producing high level protein expression in the airways of mice over many weeks and hence has been proposed as a favoured promoter for use in airway gene therapy for a variety of respiratory diseases. Examples of expression vectors for use in directing transgene expression in airway epithelia have also been described in Chow et al. Proc. Natl. Acad. Sci. USA 1997; 94: 14695-14700. Such expression vectors can be administered via the airways, e.g into the nasal cavity or trachea.

Virally-induced Exacerbations of Respiratory Disease

In the present invention, an apoptosis-inducing agent is used to treat virally-induced exacerbations of respiratory disease. A virally-induced exacerbation of a respiratory disease is an increase in the severity of a respiratory disease that results from the presence of a virus, such as rhinovirus. The virus typically leads to a worsening of the symptoms associated with the respiratory disease, a reduced response to therapy and in some cases hospitalisation. The virus typically infects the lung tissue, including or especially the bronchial epithelium. Generally, the virus results in the release of inflammatory mediators and increased bronchial responsiveness. As hereinbefore indicated, rhinovirus is recognised as a common pathogen trigger of asthma exacerbation. Similarly, rhinovirus may promote undesirable exacerbation of other respiratory diseases. Thus, respiratory diseases of interest in relation to the present invention also include conditions which may be labelled COPD.

Therapy

Administration of IFN-β, an agent that increases IFN-β expression or a polynucleotide as discussed above may be either for prophylactic or therapeutic purpose. When provided prophylactically, the IFN-β, agent or polynucleotide is provided in advance of any exacerbation. The prophylactic administration of the IFN-β, agent or polynucleotide serves to prevent or attenuate any subsequent exacerbation. When provided therapeutically the IFN-β, agent or polynucleotide is provided at (or shortly after) the onset of a symptom of the exacerbation. The therapeutic administration of the IFN-β, agent or polynucleotide serves to attenuate any actual exacerbation. The individual treated may be any animal, but preferably the individual treated will be a human, most preferably an asthmatic human.

The IFN-β, agent or polynucleotide may be administered in a medicament or pharmaceutical composition suitable for airway delivery which will typically also include a pharmaceutically acceptable excipient. Such an "excipient" generally refers to a substantially inert material that is nontoxic and does not interact with other components of the composition in a deleterious manner.

Pharmaceutically acceptable excipients include, but are not limited to, liquids such as water, saline, polyethyleneglycol, hyaluronic acid, glycerol and ethanol. Pharmaceutically acceptable salts can be included therein, for example, mineral acid salts such as hydrochlorides, hydrobromides, phosphates, sulphates, and the like; and the salts of organic acids such as acetates, propionates, malonates, benzoates, and the like.

It is also preferred, although not required, that a composition or medicament comprising the therapeutic agent will contain a pharmaceutically acceptable carrier that serves as a stabilizer, particularly for peptide, protein, polynucleotide or other like agents. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. It may also be useful to employ a charged lipid and/or detergent. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, for example, TWEEN® surfactants (Atlas Chemical Industries, Wilmington, Del.), polyoxyethylene ethers, for example Brij, pharmaceutically acceptable fatty acid esters, for example, lauryl sulfate and salts thereof (SDS), and like materials. A thorough discussion of pharmaceutically acceptable excipients, carriers, stabilizers and other auxiliary substances is available in Remingtons Pharmaceutical Sciences (Mack Pub. Co., N.J. 1991).

A suitable composition for airway delivery of IFN-β may, for example, be formulated as described in U.S. Pat. No. 6,030,609 by dissolving lyophilised IFN-β in a pharmaceutically acceptable vehicle such as sterile distilled water or sterile physiological saline, optionally with addition of one or more carriers, stabilizers, surfactants or other agents in order to enhance effectiveness of the IFN-β active agent.

A composition comprising a prophylactically or therapeutically effective amount of the IFN-β, agent or polynucleotide described herein may conveniently be delivered to the lung airways by means of an aerosol nebuliser. An appropriate effective amount may be determined by appropriate clinical testing and will vary with for example the activity of the IFN-β administered or induced. The IFN-β, agent or polynucleotide may for example, be administered in microgram amounts. They are administered to the subject to be treated in a manner compatible with the dosage formulation, and in an amount that will be effective to bring about the desired effect. The amount to be delivered may be 1 µg to 5 mg, for example 1 to 50 µg, depending on the subject to be treated. The exact amount necessary will vary depending on the age and general condition of the individual being treated and agent selected, as well as other factors. For example, 250 µg of IFN-β may be administered every alternate day or 30 µg of IFN-β may be administered weekly (Cook, J Neurol, 2003; 250 Suppl 4: 15-20; Durelli, J Neurol 2003; 250 Suppl 4: 9-14).

The IFN-β, agent or polynucleotide may be administered on its own or in combination with another therapeutic compound. In particular, the IFN-β, agent or polynucleotide may be administered in conjunction with a therapeutic compound used to treat the respiratory disease in the individual. The IFN-β, agent or polynucleotide and additional therapeutic compound may be formulated in the same or different compositions. In one embodiment, the IFN-β, agent or polynucleotide is administered to an individual with asthma in combination with an inhaled corticosteroid. The IFN-β, agent or polynucleotide may be administered simultaneously, sequentially or separately with an inhaled corticosteroid.

Thus, in a further aspect of the present invention there is provided a product for treatment of asthma comprising for simultaneous, separate or sequential airway administration (i) a first agent selected from (a) IFN-β, (b) an agent that increases IFN-β expression and (c) a polynucleotide capable of expressing (a) or (b) and (ii) an inhaled corticosteriod. Preferably, such a product will provide for simultaneous, separate or sequential administration of IFN-β and an inhaled corticosteroid, for example, fluticasone, beclomethasone and budesonide.

A first agent as defined above and an inhaled corticosteriod may, for example, be provided in the form of a single pharmaceutical composition suitable for aerosol delivery to the airways.

As indicated above, there are also now provided novel medical uses of interferon lambda (IFN-λ). A preferred use of IFN-λ polypeptides now presented is to alleviate or prevent viral-induced exacerbation of asthma, especially in humans. Such viral-induced exacerbation will most commonly be the result of RV-infection. However, the invention is equally applicable to asthma exacerbation by other viral infections including RSV infection and influenza infection.

Methods of diagnosing whether a patient has or is suffering from a respiratory disorder are well known in the art. For example, guidelines for diagnosing asthma are provided by the Global Initiative for Asthma (GINA) as part of a publication titled: "Pocket guide for asthma prevention and management", which is available from www.ginasthma.com. Similarly, guidelines for diagnosing COPD are provided by the Global Initiative for Obstructive Lung Disease (GOLD) as part of a publication titled: "Pocket guide to COPD diagnosis, management and prevention: a guide for heath care professionals", which is available from www.goldcopd.com. Relevant extracts from both of these documents are provided in the accompanying examples.

A method of the invention may comprise administering one IFNλ polypeptide or the patient may be administered a mixture of IFNλ-1 and IFNλ-2, or a mixture of IFNλ-1 and IFNλ-3, or a mixture of IFNλ-2 and IFNλ-3, or a mixture of IFNλ-1, IFNλ-2 and IFNλ-3.

By "IFNλ polypeptide" we include those polypeptides disclosed in GenBank accession numbers Q8IU54, Q8IZJ0, Q8IZI9, and set out below:

```
(IFNλ-1)
                                         (SEQ ID NO: 5)
  maaawtvvlv tlvlglavag pvptskpttt gkgchigrfk slspqelasf kkardalees lklknwscss pvfpgnwdlr llqvrerpva leaelaltlk vleaaagpal edvldqplht lhhilsqlqa ciqpqptagp rprgrlhhwl hrlqeapkke sagcleasvt fnlfrlltrd lkyvadgnlc lrtsthpest (IFNλ-2)
                                         (SEQ ID NO: 6)
  mkldmtgdct pvlvlmaavl tvtgavpvar lhgalpdarg chiaqfksls pqelqafkra kdaleeslll kdcrchsrlf prtwdlrqlq vrerpmalea elaltlkvle atadtdpalv dvldqplhtl hhilsqfrac iqpqptagpr trgrlhhwly rlqeapkkes pgcleasvtf nlfrlltrdl ncvasgdlcv
```

-continued (IFNλ-3)
(SEQ ID NO: 7)
mkldmtgdcm pvlvlmaavl tvtgavpvar lrgalpdarg chiaqfksls pqelqafkra kdaleeslll kdckcrsrlf prtwdlrqlq vrerpvalea elaltlkvle atadtdpalg dvldqplhtl hhilsqlrac iqpqptagpr trgrlhhwlh rlqeapkkes pgcleasvtf nlfrlltrdl ncvasgdlcv By "IFNλ polypeptide" is included any full length naturally occurring IFNλ polypeptide or fragment thereof, or any variant thereof.

"Fragments" or "variants" of an IFNλ polypeptide are those which have substantially the same or more biological activity of IFNλ polypeptide so as to be useful as therapeutic agents in the method of the invention. Such variants and fragments will usually include at least one region of at least five consecutive amino acids which has at least 90% homology with the most homologous five or more consecutive amino acids region of the said polypeptide. A fragment is less than 100% of the whole polypeptide.

The biological activity of "fragments" or "variants" of an IFNλ polypeptide may be determined by, for example, measuring the anti-viral activity of such a polypeptide against RV infection in bronchial epithelial cells, as described in Example 1 below. By "substantially the same or more" we include where the "fragments" or "variants" of an IFNλ polypeptide has at least 50%, 60%, 70%, 80%, 90%, 95%, 100% or more of the biological activity of IFNλ polypeptide.

It will be recognised by those skilled in the art that the IFNλ polypeptides may be modified by known polypeptide modification techniques. These include the techniques disclosed in U.S. Pat. No. 4,302,386 issued 24 Nov. 1981 to Stevens, incorporated herein by reference. Such modifications may enhance biological activity to be useful as therapeutic agents. For example, a few amino acid residues may be changed. Unwanted sequences can be removed by techniques well known in the art. For example, the sequences can be removed via limited proteolytic digestion using enzymes such as trypsin or papain or related proteolytic enzymes.

Thus, the IFNλ polypeptides of use in a method of the invention include modified polypeptides, including synthetically derived polypeptides or fragments of the original polypeptide.

The IFNλ polypeptide may be prepared from a number of different sources. For example, recombinant IFNλ polypeptide can be expressed in a cell using a number of different expression systems (both prokaryotic or eukaryotic) and isolated, optionally with a protein tag. Recombinant IFNλ polypeptide may be secreted into a supernatant and the recombinant polypeptide may then be purified from the supernatant.

Methods by which recombinant polypeptide can be expressed and purified from cells are well known in the art and are routine procedure which can be performed by the skilled person. Such methods are disclosed in, for example, and are provided in, for example, Sambrook et al., Molecular Cloning: A Laboratory Manual. 2001. 3 rd edition.

In general, DNA encoding the desired IFNλ polypeptide is expressed in a suitable microbial host cell. Thus, DNA encoding IFNλ polypeptide may be used in accordance with known techniques, appropriately modified in view of the teachings contained herein, to construct an expression vector, which is then used to transform an appropriate host cell for the expression and production of IFNλ polypeptide. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

The DNA encoding IFNλ polypeptide may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. Thus, the DNA insert may be operatively linked to an appropriate promoter. Bacterial promoters include the E. coli lacI and lacZ promoters, the T3 and T7 promoters, the gpt promoter, the phage λ PR and PL promoters, the phoA promoter and the trp promoter. Eukaryotic promoters include the CMV immediate early promoter, the HSV thymidine kinase promoter, the early and late SV40 promoters and the promoters of retroviral LTRs. Other suitable promoters will be known to the skilled artisan. The expression constructs will desirably also contain sites for transcription initiation and termination, and in the transcribed region, a ribosome binding site for translation. (Hastings et al, International Patent No. WO 98/16643, published 23 Apr. 1998).

The vector is then introduced into the host through standard techniques. Generally, not all of the hosts will be transformed by the vector and it will therefore be necessary to select for transformed host cells. One selection technique involves incorporating into an expression vector containing any necessary control elements a DNA sequence marker that codes for a selectable trait in the transformed cell. These markers include dihydrofolate reductase, G418 or neomycin resistance for eukaryotic cell culture, and tetracyclin, kanamycin or ampicillin resistance genes for culturing in E. coli and other bacteria. The selectable markers could also be those which complement auxotrophisms in the host. Alternatively, the gene for such a selectable trait can be on another vector, which is used to co-transform the desired host cell.

Host cells that have been transformed by DNA encoding IFNλ polypeptide are then cultured for a sufficient time and under appropriate conditions known to those skilled in the art in view of the teachings disclosed herein to permit the expression of interferon polypeptide.

Many microbial expression systems are known, including systems employing: bacteria (e.g. E. coli and B. subtilis) transformed with, for example, recombinant bacteriophage, plasmid or cosmid DNA expression vectors; yeasts (e.g. Saccaromyces cerevisiae) transformed with, for example, yeast expression vectors; insect cell systems transformed with, for example, viral expression vectors (e.g. baculovirus).

The vectors can include a prokaryotic replicon, such as the Col E1 ori, for propagation in a prokaryote. The vectors can also include an appropriate promoter such as a prokaryotic promoter capable of directing the expression (transcription)

of the genes in a bacterial host cell, such as *E. coli*, transformed therewith, and a translation initiation sequence, such as the Shine-Dalgarno consensus ribosome-binding sequence, usually adjacent to the promoter sequence, that forms part of the resulting transcript and from which translation of the cloned gene transcript can commence.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA). Preferred prokaryotic vector plasmids include pET26b (Novagen, Nottingham, UK).

Useful yeast plasmid vectors are pRS403-406 and pRS413-416 and are generally available from Stratagene Cloning Systems (La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

Methods well known to those skilled in the art can be used to construct expression vectors containing the coding sequence and, for example appropriate transcriptional or translational controls. One such method involves ligation via homopolymer tails. Homopolymer polydA (or polydC) tails are added to exposed 3' OH groups on the DNA fragment to be cloned by terminal deoxynucleotidyl transferases. The fragment is then capable of annealing to the polydT (or polydG) tails added to the ends of a linearised plasmid vector. Gaps left following annealing can be filled by DNA polymerase and the free ends joined by DNA ligase.

Another method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic molecules called linkers and adaptors. DNA fragments with blunt ends are generated by bacteriophage T4 DNA polymerase or *E. coli* DNA polymerase I which remove protruding 3' termini and fill in recessed 3' ends. Synthetic linkers, pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end.

Synthetic linkers containing a variety of restriction endonuclease sites are commercially available from a number of sources including International Biotechnologies Inc, New Haven, Conn., USA.

A desirable way to modify DNA encoding the IFNλ polypeptide is to use the polymerase chain reaction as disclosed by Saiki et al. (1988) Science 249, 487-491. In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Accordingly, the procedures outlined above can be used to prepare a microbial expression system for the preparation of IFNλ polypeptide.

The IFNλ polypeptide can be recovered from microbial expression systems using a number of different well known methods, including ammonium sulphate or ethanol precipitation, acid extraction, anion or cation exchange chromatography, phosphocellulose chromatography, hydrophobic interaction chromatography, affinity chromatography, hydroxylapatite chromatography, lectin chromatography, dye-ligand chromatography and reverse phase high performance liquid chromatography ("HPLC").

Such methods may include the step of lysing the microbial host cells (unless the expression system directed the IFNλ polypeptide to be secreted from the cell).

Alternatively, IFN-λ polypeptides may be synthesised by the Fmoc-polyamide mode of solid-phase peptide synthesis as disclosed by Lu et al. (1981) J. Org. Chem. 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

As indicated above, one or more IFN-λ polypeptides may be administered directly or via expression from one or more polynucleotides. Such a polynucleotide may preferably be in the form of a vector capable of directing expression of the IFN-λ(s) in the bronchial epithelium. Such expression vectors may be any type conventionally considered for gene therapy. They may be plasmid expression vectors administered as naked DNA or complexed with one or more cationic amphiphiles, e.g. one or more cationic lipids, e.g. in the form of DNA/liposomes. A viral vector may alternatively be employed. Vectors for expression of therapeutic proteins in the airways of human lung have previously been described. For example, Published International Application WO 01/91800 (Isis innovation Limied) describes for such purpose expression vectors including the human ubiquitin C promoter. Examples of expression vectros for use in directing transgene expression in airway epithelia have also been described in Chow et al., Proc, Natl. Acad. Sci. USA (1997) 94, 14695-14700.

IFN-λ polypeptides may be formulated together with one or more acceptable carriers to provide a pharmaceutical composition for therapeutic use. The carrier(s) must be "acceptable" in the sense of being compatible with the compound and not deleterious to the recipients thereof. Such carriers are well known in the pharmaceutical art. For the purpose of treatment of a viral-induced exacerbation of a respiratory disorder in accordance with the invention, it is particularly preferred that the IFNλ polypeptide is formulated for airway administration.

For such administration, the IFNλ polypeptide is conveniently delivered in the form of an aerosol spray presentation from a pressurized container, pump, spray or nebulizer with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurized aerosol, the dosage unit may be determined by providing a valve to deliver a metered amount. The pressurized container, pump, spray or nebulizer may contain a solution or suspension of the active compound (s), e.g. using a mixture of ethanol and the propellant as the solvent, which may additionally contain a lubricant, e.g. sorbitan trioleate. The formulation may also be delivered using ultrasonic nebulization techniques.

Thus, as indicated above, in a further aspect the invention provides a device containing a pharmaceutical composition comprising a therapeutic agent which is (i) one or more IFN-λ polypeptides or (ii) one or more polynucleotides capable of expressing one or more IFN-λ polypeptides as discussed above and suitable for airway delivery of said composition. Such a composition may be supplemented with an additional therapeutic agent used to treat the respiratory disorder for simultaneous, separate or sequential administration. Thus, the additional therapeutic agent may be formulated to provide a single composition or provided in a separate composition. Products suitable for such administration regimes constitute a still further aspect of the invention.

Thus reference has previously been made above to a product for treatment of viral-induced exacerbation of asthma comprising for simultaneous, separate or sequential administration (a) at least one IFN-λ polypeptide or a polynucleotide capable of expressing at least one IFN-λ polypeptide in the bronchial epithelial cells to be targeted and (b) an inhaled corticosteroid, such as, for example, fluticasone, beclomethasone and budesonide. Such a product may be in the form of a single pharmaceutical composition suitable for aerosol delivery to the airways.

It will be appreciated that the overall daily dose with an aerosol will vary from patient to patient, and may be administered in a single dose or in divided doses throughout the day.

An IFNλ polypeptide to be administered for a method of the invention may be derivatised to improve the pharmacokinetic or immunogenic properties of the polypeptide. For example, an IFN-λ polypeptide may be PEGylated and/or conjugated to albumin or a further substance so as to increase stability of the IFN-λ polypeptide.

PEGylation is a method well known to those skilled in the art wherein a polypeptide or peptidomimetic compound is modified such that one or more polyethylene glycol (PEG) molecules are covalently attached to the side chain of one or more amino acids or derivatives thereof. It is one of the most important molecule altering structural chemistry techniques (MASC). Other MASC techniques may be used; such techniques may improve the pharmacodynamic properties of the molecule, for example extending its half life in vivo. A PEG-protein conjugate is formed by first activating the PEG moiety so that it will react with, and couple to, the protein or peptidomimetic compound of the invention. PEG moieties vary considerably in molecular weight and conformation, with the early moieties (monofunctional PEGs; mPEGs) being linear with molecular weights of 12 kDa or less, and later moieties being of increased molecular weights. PEG2, a recent innovation in PEG technology, involves the coupling of a 30 kDa (or less) mPEG to a lysine amino acid (although PEGylation can be extended to the addition of PEG to other amino acids) that is further reacted to form a branched structure that behaves like a linear mPEG of much greater molecular weight (Kozlowski et al., (2001), Biodrugs 15, 419-429). Methods that may be used to covalently attach the PEG molecules to the polypeptide or peptidomimetic compound of the invention are further described in Roberts et al., (2002) Adv. Drug Deliv Rev 54, 459-476, Bhadra et al., (2002) Pharmazie 57, 5-29, Kozlowski et al., (2001) J Control Release 72, 217-224, and Veronese (2001) Biomaterials, 22, 405-417 and references referred to therein.

To improve pharmokinetic properties and/or stability, it may additionally or alternatively be chosen to replace naturally-occurring amino acid residues of a natural IFN-λ polypeptide by non-naturally-occurring amino acid residues.

Therapeutic proteins such as interferons and growth hormones, in their native state or when recombinantly produced, can be labile molecules exhibiting short shelf-lives, particularly when formulated in aqueous solutions. The instability in these molecules when formulated for administration dictates that the molecules may have to be lyophilized and refrigerated at all times during storage, thereby rendering the molecules difficult to transport and/or store. Storage problems are particularly acute when pharmaceutical formulations must be stored and dispensed outside of the hospital environment. Many protein and peptide drugs also require the addition of high concentrations of other protein such as albumin to reduce or prevent loss of protein due to binding to the container. This is a major concern with respect to proteins, such as interferons.

The role of albumin as a carrier molecule and its inert nature are desirable properties for use as a carrier and transporter of polypeptides in vivo. Fusion of albumin to the therapeutic protein may be achieved by genetic manipulation, such that the DNA coding for albumin, or a fragment thereof, is joined to the DNA coding for the therapeutic protein. A suitable host is then transformed or transfected with the fused nucleotide sequences, so arranged on a suitable plasmid as to express a fusion polypeptide. The expression may be effected in vitro from, for example, prokaryotic or eukaryotic cells, or in vivo e.g. from a transgenic organism.

The invention may be employed for prophylactic or therapeutic purpose. A person could be considered to be at seasonal risk of developing a respiratory viral infection. Thus in the winter there is excess of rhinovirus infections and clear winter epidemics of influenza and RSV. A person with asthma or COPD could be expected to develop symptoms of viral exacerbation upon exposure to a person who has a clear clinical cold. In this case, one or more IFN-λ polypeptides may be administered in accordance with the invention after such exposure to prevent or at least reduce development of viral-exacerbation of the respiratory disorder.

The invention will be understood to be applicable to any viral infection causing viral induced exacerbation of a respiratory disorder associated with deficient IFN-λ production in the bronchial epithelium or for preventing such exacerbation. The viral infection may be infection by, for example, any of rhinovirus, RSV or influenza virus. The viral infection may be caused by further respiratory viruses. The invention is particularly preferred for use, however, in treating or preventing rhinovirus-induced exacerbation of a respiratory disorder, especially rhinovirus-induced exacerbation of asthma.

As discussed above, it is now additionally suggested that interferon-λs may be beneficial in the prevention of an allergic disorder such as asthma, independent of their role against virus infections. The data we have generated suggests that administering interferon-λs early in life would mimic the protective effect of infectious disease, promote TH1 immune responses, and prevent the development of TH2 driven allergic sensitization and allergic disorder. This preventive therapy could be administered early in life, but interferon-λs could also be administered later in life to treat/cure allergic disorder, in other words to reverse the TH2 driven sensitization and immune responses to allergens.

"Allergic disorder" is a condition associated with a T helper lymphocyte-2 (Th-2) type immune response. In an allergic reaction, high IgE levels occur and Th-2 immune responses predominate over Th-1 responses, resulting in an inflammatory response.

By "allergic disorder" we include allergic sensitization, allergic rhinitis, eczema, food allergies, anaphylaxis, dermatitis, allergic rhinitis, allergic conjunctivitis, allergic airways disease, hyper-eosinophilic syndrome, contact dermatitis and respiratory diseases characterised by eosinophilic airways inflammation and airway hyperresponsiveness such as allergic asthma, intrinsic asthma, allergic bronchopulmonary aspergillosis, eosinophilic pneumonia, allergic bronchitis bronchiectasis, occupational asthma, reactive airway disease syndrome, interstitial lung disease, hyperosinophilic syndrome or parasitic lung disease. In one embodiment of this aspect of the invention the allergic disease is allergic sensitization, allergic rhinitis, eczema, food allergies, anaphylaxis, dermatitis, allergic rhinitis, allergic conjunctivitis, hyper-eosinophilic syndrome or contact dermatitis.

A further embodiment of this aspect of this invention is wherein the respiratory disorder is asthma (allergic or intrinsic), chronic obstructive pulmonary disease (COPD), allergic bronchopulmonary aspergillosis, eosinophilic pneumonia, allergic bronchitis bronchiectasis, occupational asthma, reactive airway disease syndrome, interstitial lung disease, hyperosinophilic syndrome or parasitic lung disease. Preferably the respiratory disorder is asthma and/or COPD.

A further aspect of the invention is the use of IFNλ polypeptide in the manufacture of a medicament for the prevention or treatment of an allergic disorder.

Preferably, the allergic disorder is an allergic sensitization, asthma, allergic rhinitis, eczema, food allergies, anaphylaxis, allergic rhinitis, eczema, food allergies, anaphylaxis, dermatitis, allergic rhinitis, allergic conjunctivitis, allergic airways disease, hyper-eosinophilic syndrome, contact dermatitis and respiratory diseases characterised by eosinophilic airways inflammation and airway hyperresponsiveness such as allergic asthma, intrinsic asthma, allergic bronchopulmonary aspergillosis, eosinophilic pneumonia, allergic bronchitis bronchiectasis, occupational asthma, reactive airway disease syndrome, interstitial lung disease, hyperosinophilic syndrome or parasitic lung disease.

The following examples are provided to illustrate the invention.

EXAMPLE 1

Study of Bronchial Epithelial Cells from Asthma Patients

Subjects

All subjects were non-smokers, with no exacerbation of their lung disease or history of respiratory tract infection in the preceding 4 weeks. Allergy skin tests using a panel of common aero-allergens including house dust mite extract, grass pollen, tree pollen, cat dander, dog dander, Candidia, Aspergillus as well as negative (saline) and positive controls (histamine) controls. Tests were considered positive if there was a wheal response of 3 mm or greater than the negative control. Lung function was assessed by spirometry, measuring forced expiratory volume in 1 second ($FEV_1$) and forced vital capacity (FVC). Bronchial hyper responsiveness was then assessed by histamine challenge, defined by a $PC_{20}$ histamine less than 8 mg/ml. Subjects with asthma were subdivided on a basis of clinical severity in accordance with the GINA guidelines (National, H., Lung and Blood Institute. Global strategy for asthma management and prevention 96-3659a, Bethseda, 1995).

Asthma was diagnosed on a consistent history with evidence of bronchial hyper responsiveness, defined by a $PC_{20}$ histamine less than 8 mg/ml. Asthmatic subjects were classed as mild, with stable symptoms requiring treatment with salbutamol only as needed, less than 3 times per week and with moderate disease, with stable symptoms on inhaled beclomethasone of less than 1500 µg per day. Healthy controls had no previous history of lung disease, normal lung function, no evidence of bronchial hyper responsiveness on histamine challenge and were non-atopic. The study was approved by the relevant ethics committees. All subjects gave written informed consent.

Table 2 outlines the characteristics of the subjects used in the studies. $FEV_1$% predicted refers to the forced expiratory volume in 1 second expressed as a percentage of the predicted value. ICS refers to inhaled corticosteroids. Dose is expressed in dose of beclomethasone (BDP) in µg per day where 1 µg BDP=1 µg Budesonide or 0.5 µg Fluticasone.

TABLE 2

Subjects used in the studies

| | Asthma | Healthy controls | P values |
|---|---|---|---|
| Number | 14 | 10 | NA |
| Sex (% male) | 69% | 60% | P = 0.6 |
| Mean age (range) | 32 (21-58) | 29 (24-38) | P = 0.4 |
| Mean $FEV_1$ % predicted (sd) | 77.3 (15.5) | 110.3 (13.6) | P < 0.001 |
| Mean dose of ICS, BDP µg/day (sd) | 490 (260) | 0 | NA |

Tissue Culture

Epithelial cells were obtained by fibreoptic bronchoscopy in accordance with standard published guidelines, all subjects were premedicated with salbutamol (Hurd, J Allergy Clin Immunol, 1991; 88: 808-814) and cell culture was performed as previously described (Bucchieri, et al., Am. J. Respir. Cell Mol. Biol., 2001; 27: 179-185). In brief cells were obtained using a sheathed nylon cytology brush by taking 5-10 brushings from second to third generation bronchi under direct vision. Primary cultures were established by seeding freshly brushed bronchial epithelial cells into culture dishes. Cells were cultured at 37° C. and 5% carbon dioxide in hormonally supplemented bronchial epithelial growth medium (BEGM; Clonetics, San Diego, USA) containing 50 U/ml penicillin and 50 µg/ml streptomycin. Cells were cultured and passaged into tissue culture flasks using trypsin. At passage 2 cells were seeded onto 12 well trays and cultured until 80% confluent (Bucchieri, et al., Am J Respir Cell Mol Biol, 2001; 27: 179-185). Epithelial cell purity was checked by differential cell counts on cytospins of the harvested cells.

Cells were also treated alone or following infection with the major group RV-16. After infection cells were also treated with the caspase 3 inhibitor ZVD-fmk at 120 µM (Calbiochem, La Jolla, Calif., USA) and human IFNβ at 100IU (Sigma Chemical St Louis Mo., USA).

Preparation and Infection With RV

We generated RV-16 stocks by infecting cultures of Ohio HeLa cells as previously described (Papi and Johnston, J Biol Chem, 1999; 274: 9707-9720); cells and supernatants were harvested, cells were disrupted by freezing and thawing, cell debris was pelleted by low speed centrifugation and the clarified supernatant frozen at −70° C.

RV titration was performed by exposing confluent monolayers of HeLa cells in 96-well plates to serial 10-fold dilutions of viral stock and cultured for 5 days at 37° C. in 5% $CO_2$. Cytopathic effect was assessed and the tissue culture infective dose of 50% ($TCID_{50}$/ml) was then determined and the multiplicity of infection (MOI) derived (Papi and Johnston, J Biol Chem, 1999; 274: 9707-9720). As a negative control for all experiments RV-16 was inactivated by exposure to UV irradiation at 1200 µJ/cm$^2$ UV light for 30 minutes. Inactivation was confirmed by repeating viral titrations in HeLa cells.

The desired concentration of RV-16 was applied to cells that were gently shaken at 150 rpm at room temperature for 1 hour. The medium was then removed and the wells washed twice with 1 ml Hanks Balanced Salt Solution. Fresh medium was then applied and the cells cultured at 37.5° C. and 5% $CO_2$ for the desired time. As negative controls cells were treated with medium alone and UV inactivated RV-16.

Confirmation of infection of epithelial cells and quantification of viral production was assessed by HeLa titration assay (Papi and Johnston, J Biol Chem, 1999; 274: 9707-9720) and quantitative reverse transcription polymerase chain reaction (qPCR), as described below.

Analysis of Cell Viability

Viability and apoptosis were assessed by flow cytometry as previously described (Puddicombe et al., Am J Respir Cell Mol Biol, 2003; 28: 61-68). Briefly 8 h after RV infection, adherent cells were removed with trypsin and added to non-adherent cells. Cells were stained with Annexin-V conjugated to the fluorochrome Phycoerythrin (PE) and the vital dye 7-Amino-actinomycin (7-AAD). Flow cytometric data were analysed using WinMDI 2.8. The active forms of caspase 3/7 were detected using the Apo-One Homogenous Caspase 3/7 assay (Promega, Maddison, USA). Cells were plated in quadruplicate for each condition. Two wells were stained with methylene blue and cell biomass estimated. The other two wells were lysed with lysis buffer and read on a fluorescent plate reader with an excitation wavelength of 485 nm and emission of 530. Caspase activity was then corrected for cell biomass. Cell lysis was measured by determining the activity of lactate dehydrogenase (LDH) in the cell supernatant that had been removed and stored at room temperature for no longer than 48 hours. The LDH activity was measured at 37° C. by an enzymatic rate method, using pyruvate as a substrate (Sigma, St Louis USA).

Reverse Transcription Quantitative PCR

Analysis of gene expression for IL-8, TNFα, ICAM-1, IFNβ and RV was carried out using RNA extracted from BECs using TRIzol reagent (Life Technologies, Paisley, UK); contaminating DNA was removed by deoxyribonuclease digestion on RNeasy Mini Kits (Qiagen, Crawley, West Sussex, UK) in accordance with manufacturer's instructions. Total RNA (1 µg) was reverse transcribed using random hexamers or oligo $(dT)_{15}$ primers and avian myeloblastosis virus transcriptase from the Reverse Transcription System (Promega, Southampton, UK), following the manufacturer's protocol. Fluorogenic probes were labelled with the 5'-reporter dye 6-carboxy-fluorescein (FAM) and the 3'-quencher dye 6-carboxy-N,N,N',N'-tetramethyl-rhodamine (TAMRA).

Housekeeping gene primers and probe for 18S ribosomal RNA was obtained from Eurogentech (Eurogentech, Southampton, UK). No-template controls and reverse transcription-negative samples were also included as controls. The icycler PCR protocol was as follows: 95° C. for 8 min; followed by 42 cycles of denaturation at 95° C. for 15 seconds followed by annealing at 60° C. for 1 min and extension at 72° C. for 15 seconds. Quantitation and real-time detection of the PCR were followed on the on icycler sequence detection system, and after completion of the PCR, the thresholds for fluorescence emission baseline were set just above background levels on the FAM and VIC layers (~15 to 20 cycles). Standard curves were calculated from the delta CT and were constructed for target genes and the 18S rRNA endogenous control, and the amount of target and endogenous control were calculated. The data were normalized by using the ratio of the amount of target gene relative to endogenous control. Comparisons were made after 8 hours of infection, as this was the time of maximum mRNA induction for IL-8.

Quantification of RV-16 differed from above. The primers used to detect RV were 0.05 µM Picornavirus Forward Oligo (5'-GTG AAG AGC CCGC AGTG TGC T-3') (SEQ ID NO:9) and 0.30 µM Picornavirus Reverse Oligo (5'-GCT CGCA GGG TTA AGG TTA GCC-3') (SEQ ID NO:10). A standard curve was constructed to quantify RV using the OL-26-OL-27 amplicon (product of OL-26 and OL-27 primers cloned into PCR 2.1 TOPO (Invitrogen). The plasmid was grown in E. coli strain XL-1blue (Stratagene), purified by a maxiprep method using commercially available reagents (Qiagen), resuspended in Tris EDTA buffer pH 8.0 at 1 ug/uL and stored at −8° C.

Expression of ICAM-1

ICAM-1 expression on cells were measured at baseline, immediately after infection and up to 24 h after RV infection by flow cytometry as described above using a monoclonal antibody to ICAM-1 (eBioscience anti-human CD54) and a FITC labelled secondary (Dako, Denmark).

Measurement of Inflammatory Mediators by ELISA

Release of Interleukin (IL)-8 and Tumour Necrosis Factor-alpha (TNF-α) (R&D systems, Abingdon, UK) and Interferon-beta (IFN-β) (Biosource Nivelles Belgium) into culture supernatants was measured using enzyme-linked immunosorbent assays (ELISA) according to the manufacturer's instructions Statistical Analysis Data was analysed using SPSS version 10.1 (SPSS Inc). As sample size was small and variables were not normally distributed the differences between the groups have been analysed using non-parametric tests; differences between two dependent variables was analysed using the signed rank test, independent variables the Wilcoxon rank sum test and multiple comparisons the Kruskal Wallis test. A p value of <0.05 was considered significant.

Results

To compare responses of normal and asthmatic bronchial epithelial cells (BECs), primary cultures were grown from bronchial brushings obtained by fibreoptic bronchoscopy from clinically characterised volunteers. Dose and time courses for infection of BECs with RV-16 were optimised initially by measuring release of IL-8 in culture supernatants obtained from infected cells. From these experiments, a dose of RV-16 with an estimated MOI of 2 was selected for detailed study (data not shown).

Inflammatory Response of Normal and Asthmatic BECs to RV-16 Infection

Figure 1A:
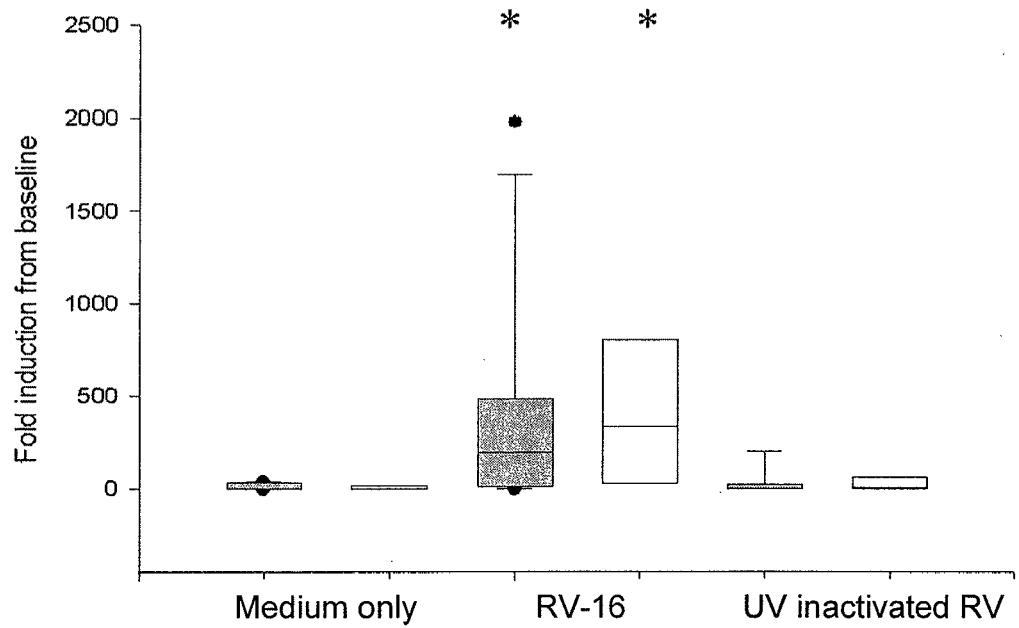
FIGS. 1a-1f show the proinflammatory responses of normal and asthmatic bronchial epithelial cells (BECs) following rhinovirus (RV) infection. Panels (a) and (c): Induction of IL-8 (a) and TNFα (c) mRNA 8 h after RV-16 infection was measured by qPCR. Asthmatic cells had a median (IQR) fold induction of IL-8 of 33.2 (7.3, 208.6) compared to 101.4 (6.4, 802.9) in healthy controls with no significant difference between groups (p=0.8). Both groups demonstrated a significant increase in IL-8 mRNA compared to cells treated with medium alone (p=0.001) and UV inactivated RV (p=0.01). For TNFα mRNA, asthmatic cells had a median fold induction from baseline of 94.4 (5.8, 1001.4) compared to 272.9 (30, 676) in healthy control cells, with no significant difference between the groups (p=0.8). Both groups demonstrated a significant increase in TNF-α mRNA compared to cells treated with medium alone (p<0.01) and UV inactivated RV (p<0.01). Panels (b) and (d): IL-8 (b) and TNFα (d) protein production in the supernatant 48 h after RV-16 infection was measured by ELISA. Median (IQR) levels of IL-8 were 922 pg/ml (868, 1065) in asthmatic cells compared to 705 pg/ml (414, 979) (p=0.6) in healthy controls. Both groups demonstrated a significant increase above cells treated with medium alone (61.4 pg/ml, p<0.001) and UV inactivated RV-16 (43.8, P<0.01). Secretion of TNF-α was 10.4 pg/ml (6.9, 29.6) in RV-16 infected asthmatic cells and 24.6 pg/ml (9.2, 30.4) in RV-16 infected healthy control cells (p=0.7). Both groups demonstrated a significant increase above cells treated with medium alone (1.85 pg/ml, p<0.01) and UV inactivated RV-16 (4.69, P<0.01). Panels (e) and (f): ICAM-1 expression was measured by flow cytometry immediately prior to RV-16 infection (e) or 24 h after infection (f). Data are expressed as mean fluorescence intensity (MFI). Prior to infection, asthmatic cells had a tendency to a lower median MFI 31(12, 80) compared to healthy control cells 67 (34, 83) but this was not significant (p=0.3). After 24 h, asthmatic cells had a significantly lower median MFI 54.6 (27.6, 145.2) compared to healthy control cells 110.4 (65, 195.3) (p=0.02). Graphs are box whisker plots, heavy line represents the median, upper box border represents $75^{th}$ quartile, lower $25^{th}$ quartile, whiskers are $5^{th}$ and $95^{th}$ centiles. *=significantly different from cells treated with medium alone and UV inactivated RV-16
Figure 1B:
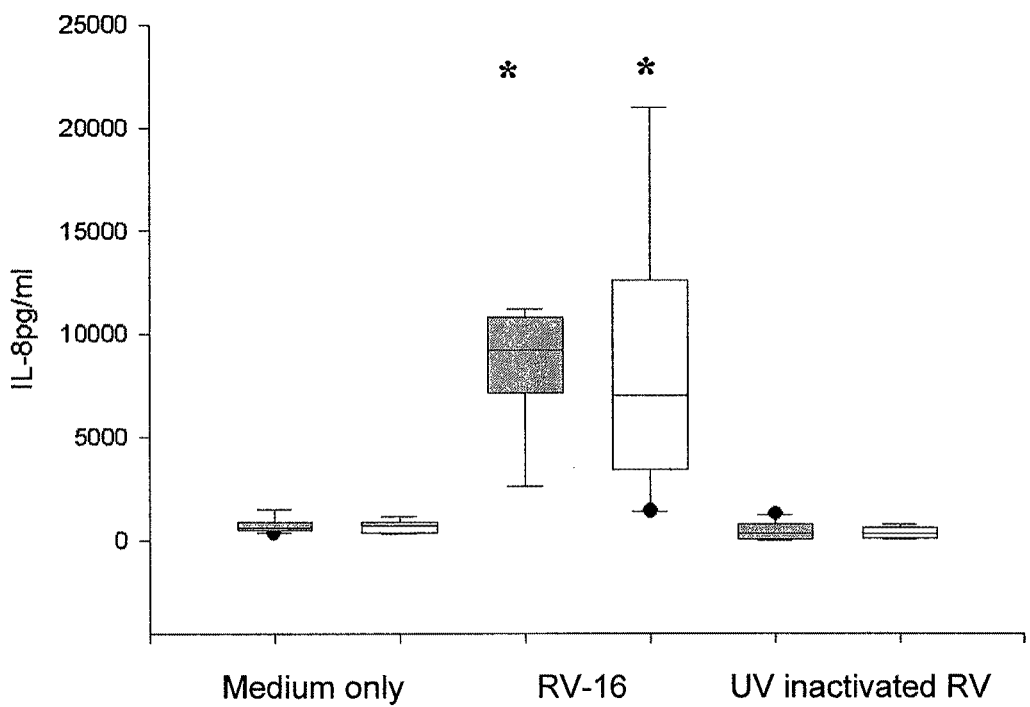
Figure 1C:
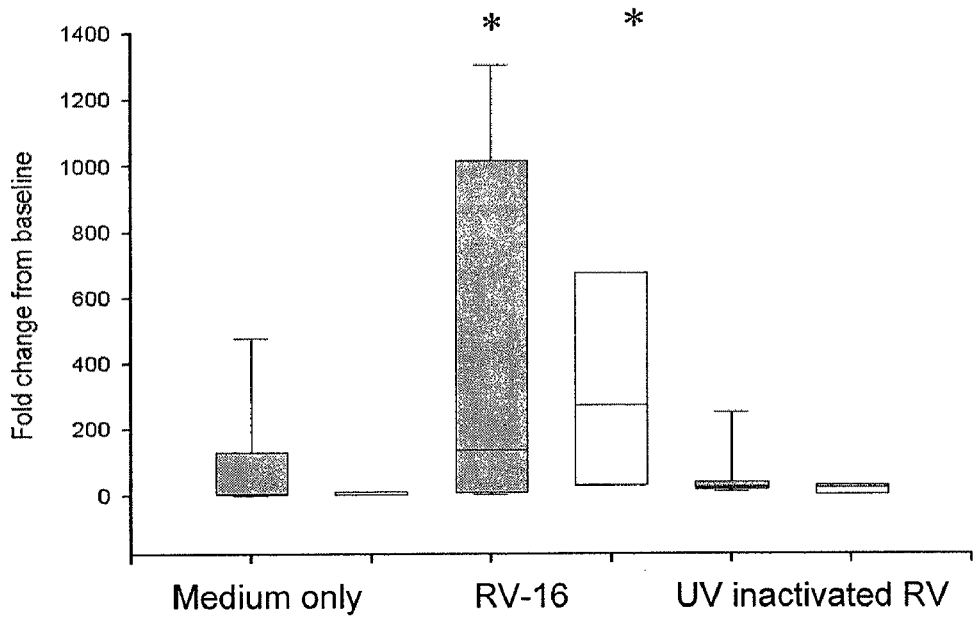
Figure 1D:
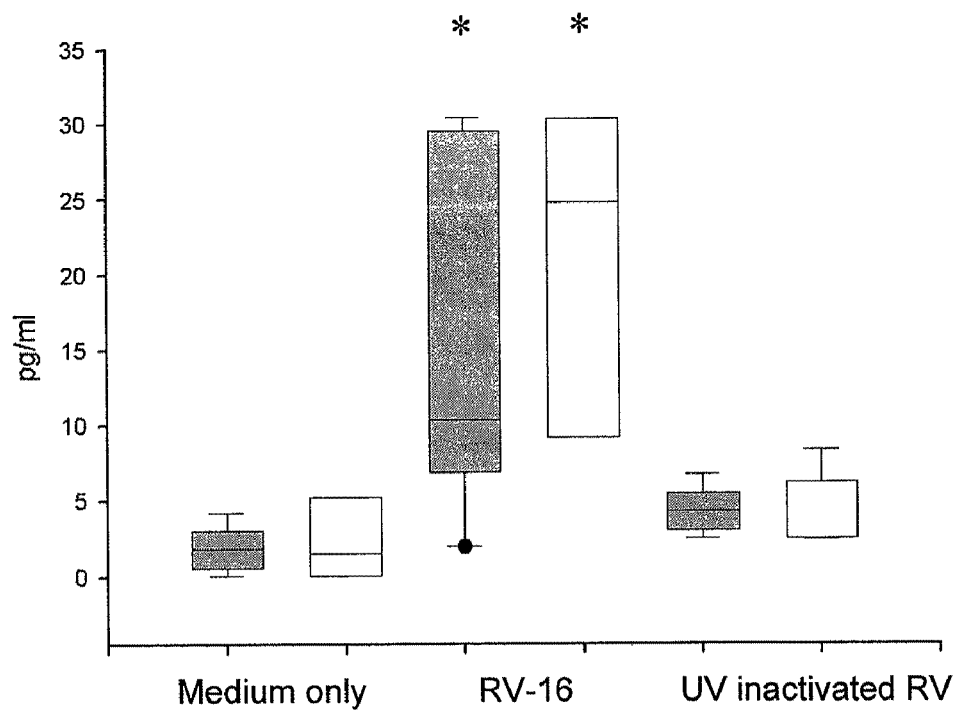

To investigate differences between normal and asthmatic bronchial epithelial cells, we recruited 14 subjects with asthma and 10 normal healthy controls (see Table 2) to undertake fibreoptic bronchoscopy. The two subject groups were similar in terms of age and sex. All asthmatics had mild-moderate persistent symptoms and used inhaled corticosteroids regularly. The responses of the primary BEC cultures to RV-16 infection were compared first by measuring induction of IL-8 and TNFα mRNA expression and protein release (FIG. 1a,c). BECs from either asthmatic or healthy controls showed a significant induction of IL-8 and TNFα mRNA 8 h post RV infection and there was a significant increase in IL-8 and TNFα protein release 48 h post infection (FIG. 1b,d); there were no significant differences between the two groups. UV-inactivated RV did not trigger a proinflammatory response.

Figure 1E:
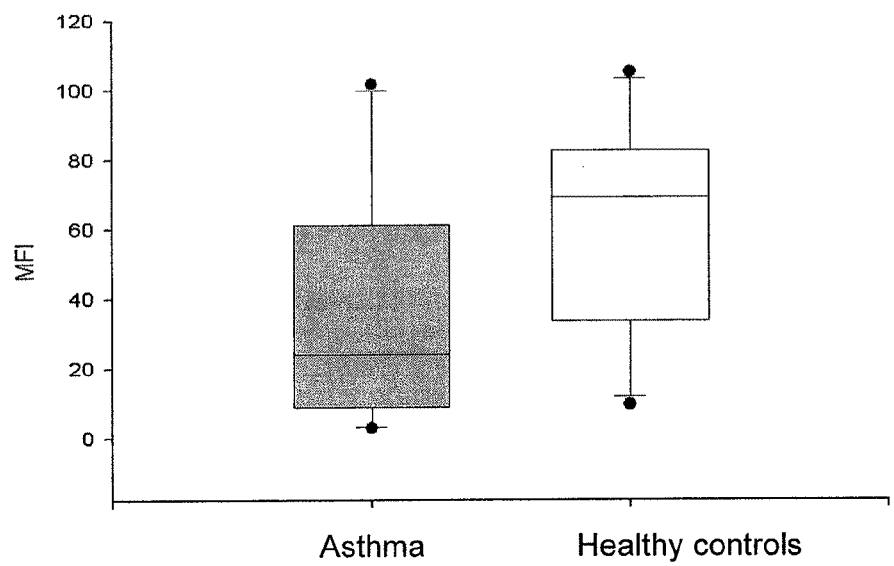
Figure 1F:
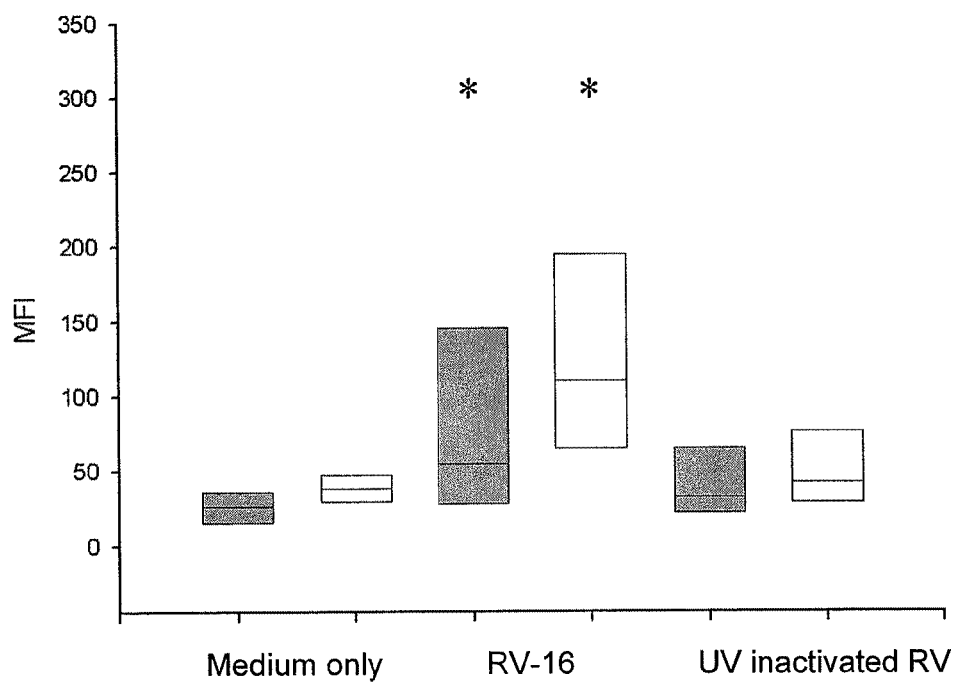

As cells were treated with a major group RV, susceptibility to infection would be expected to be dependent on expression of ICAM-1, the receptor for major group RV. To determine whether this differed between asthmatic and normal cells, ICAM levels were evaluated by flow cytometry. Prior to infection ICAM-1 expression was not significantly different in either group (FIG. 1e). By 24 h following infection, expression was similar in both groups (FIG. 1f).

Infection, Viral Yields and Cell Lysis from Primary Bronchial Epithelial Cells

Figure 2A:
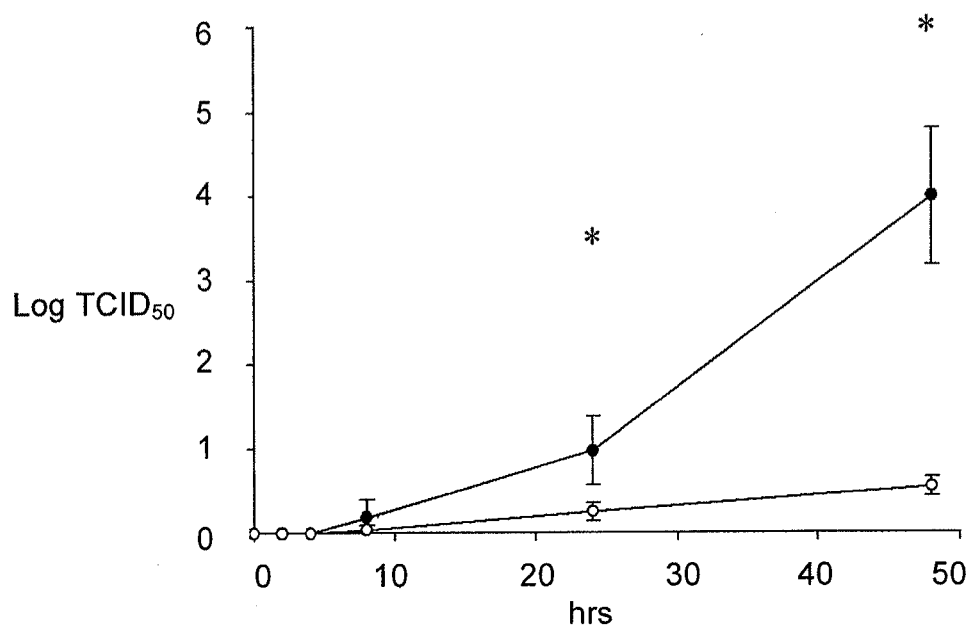
FIGS. 2a-2d show RV-16 replication and release from normal and asthmatic BECs. Panel (a): RV-16 release into the supernatant of infected cells was estimated by calculating the $TCID_{50}$ from the CPE in confluent monolayers of Ohio HeLa cells. Values have been log transformed; data points represent the geometric mean and the standard error of the mean. By 48 h significantly more RV was detected from asthmatic cells with a mean $TCID_{50}$ of 3.99, compared to 0.54 in healthy control cells (p<0.01). Panel (b): RV-16 mRNA production was measured by qPCR after 8 h of infection. Median (IQR) production from asthmatic cells was $21 \times 10^5$ ($1.6 \times 10^5$, $97 \times 10^5$) compared to $0.4 \times 10^5$ ($0.09 \times 10^5$, $0.6 \times 10^5$) from healthy controls (p<0.01). Graphs are box whisker plots, heavy line represents the median, upper box border represents $75^{th}$ quartile, lower $25^{th}$ quartile, whiskers are $5^{th}$ and $95^{th}$ centile. Dots represent outliers. Panels (c) and (d): Cell lysis as a consequence of RV-16 infection was analysed based on LDH activity in culture supernatants. Values have been log transformed; data points represent the geometric mean and the standard error of the mean. Both groups demonstrated a progressive increase in LDH activity over time that was significantly increased from baseline by 24 h (p<0.01) in asthmatic cells but not in healthy control cells even at 48 h (p=0.2) (c). By 48 h, the LDH activity from asthmatic cells showed a 3.4 mean fold increase from baseline compared to a 1.34 fold increase in the healthy control cells (p<0.001) (d). No significant change in LDH activity was seen in cells treated with medium alone or UV inactivated RV. *=results from asthmatic cells and healthy controls significantly different (p<0.01). Asthma=●, Healthy controls=○.
Figure 2B:
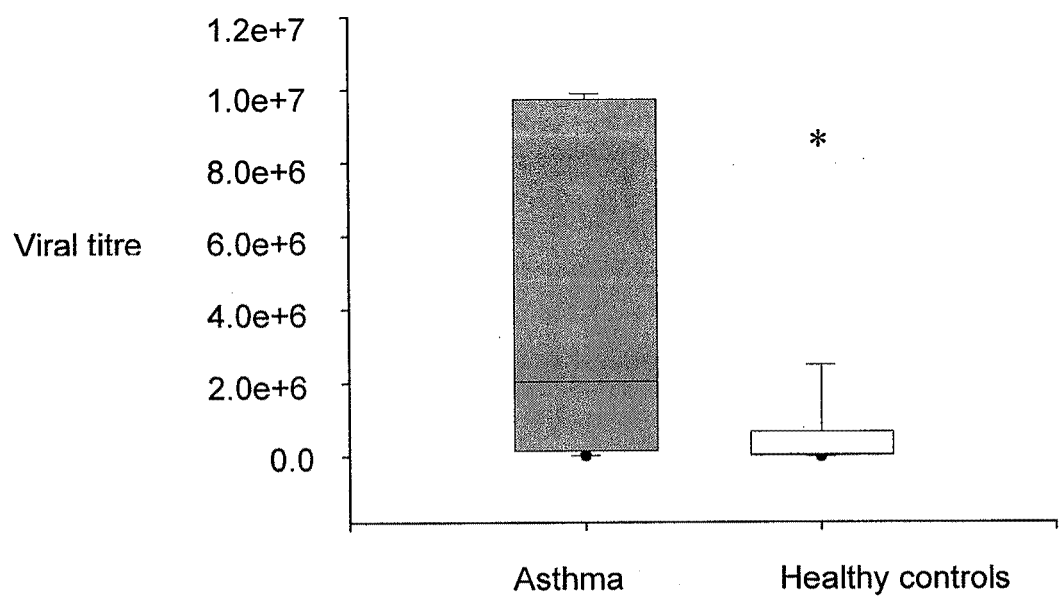

Following RV-16 infection of BEC cultures, recovery of viable RV was determined by transmission of infection and cytopathic effect (CPE) on Ohio HeLa cells from the infected supernatant of BECs. CPE was not seen using supernatants obtained up to 8 h after infection but after that virion yield following infection of the primary cultures, but thereafter rose steadily up to 48 h. In contrast with the proinflammatory responses, asthmatic BECs had a significantly greater increase in RV-16 detected by 24 h and 48 h as measured by $TCID_{50}$ (FIG. 2a). There was also a greater yield of RV-16 mRNA 8 h post infection in asthma compared to healthy controls (FIG. 2b). Given the equivalent levels of ICAM-1 expression this suggests that factors other than immediate susceptibility to infection were influencing viral yield from infected cells.

Figure 2C:
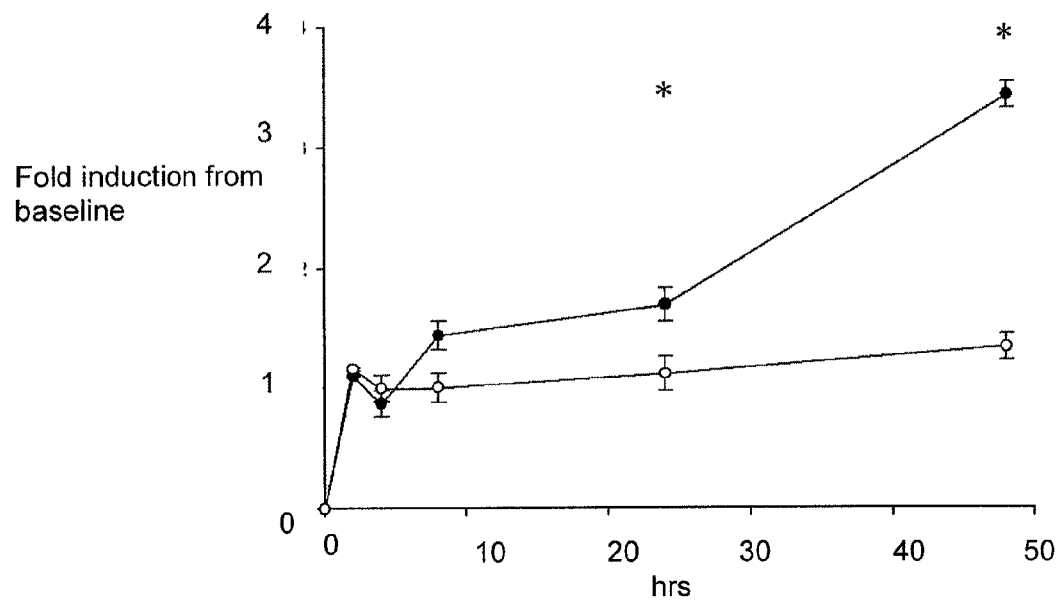
Figure 2D:
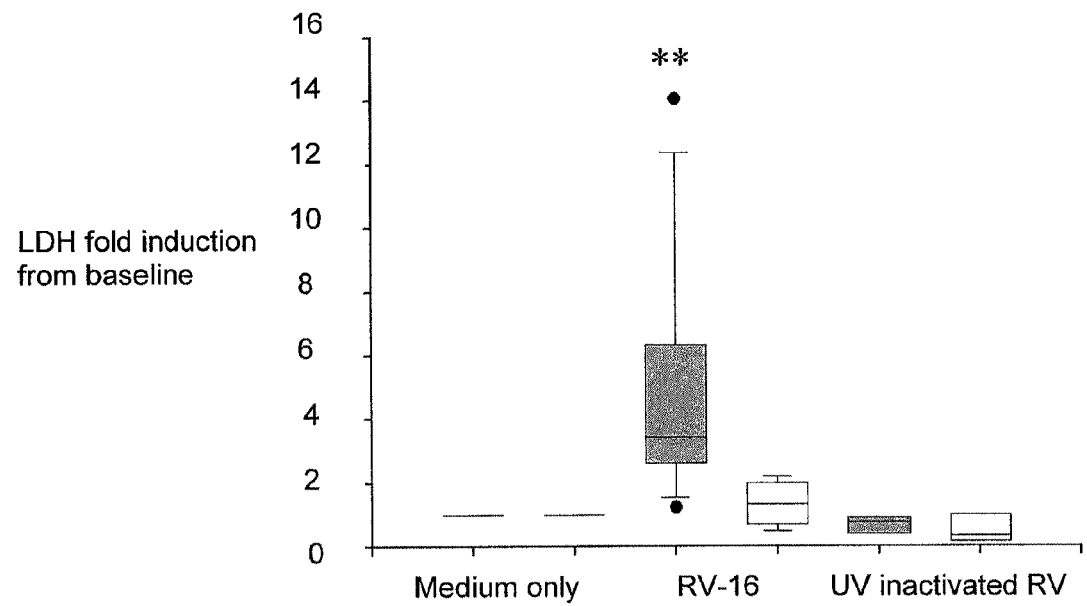

In parallel with the release of virus, there was a progressive increase in cell lysis, as measured by LDH activity, mirroring the increase in RV yield; by 48 h, this was significantly greater in asthmatic cells (FIG. 2c). Although there was no significant increase in LDH activity in cells treated with SFM alone at 48 h, there was a small but significant increase in cells treated with UV inactivated RV-16 (data not shown), however this was small by comparison with that seen in active virus cultures. These results pointed to a link between viral yield and cell lysis and led to investigation of whether early changes in cell viability would predict viral yield.

BEC Viability Following RV-16 Infection

Figure 3A:
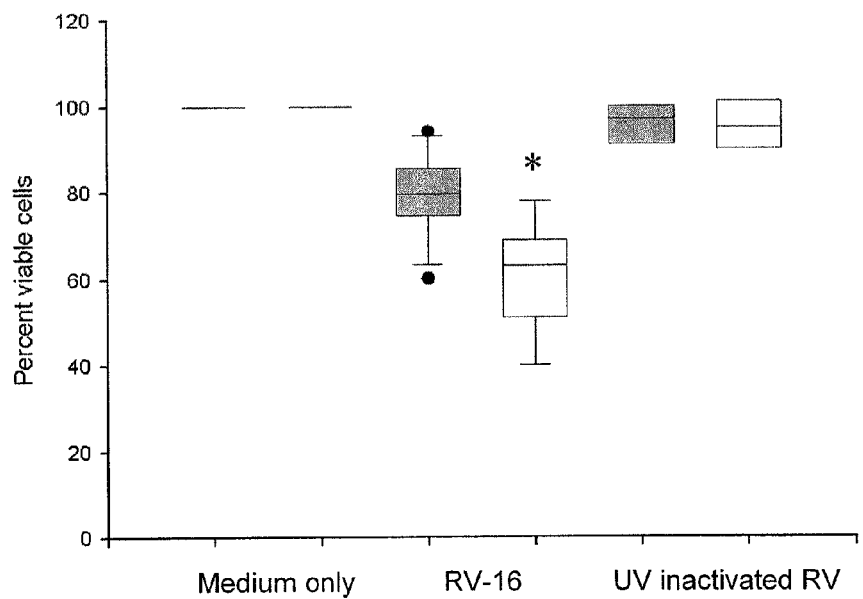
FIGS. 3a-3b show the changes in cell viability following RV-16 infection. Following RV-16 infection for 8 h, cells were stained with Annexin-V conjugated to the fluorochrome Phycoerythrin (PE) and the vital dye 7-Amino-actinomycin (7-AAD) and analysed by flow cytometry. Panel (a): Viable (AxV⁻/7AAD⁻) cell number was determined and expressed as % viability compared with cells treated with medium alone. Infection with RV-16 led to a significant reduction in median (IQR) cell viability in both asthmatic and control cells compared to medium alone (p=0.03). There was no significant reduction in viability in cells treated with inactivated RV-16 96 (91, 98) %. Asthmatic cells showed significantly better viability, median 80 (74, 86) %, compared to healthy controls 63 (51, 69) % (p=0.002). Panel (b): Apoptotic (AxV⁺/7AAD⁻) cells were also analyzed 8 h following RV-16 infection. While both groups demonstrated an increase in apoptosis with infection, asthmatic cells appeared more resistant with a fold increase of only 1.41 (1.35, 1.69), compared to 2.19 (1.98, 2.22) in healthy controls (p=0.02). Cells treated with medium alone did not show an increase in apoptosis. Cells treated with UV inactivated RV-16 did show a small increase above baseline, 1.2 (1.1, 1.4) (p=0.02). *=significantly different from cells treated with medium only (p<0.01). **=significantly different from asthmatic cells (p<0.05).
Figure 3B:
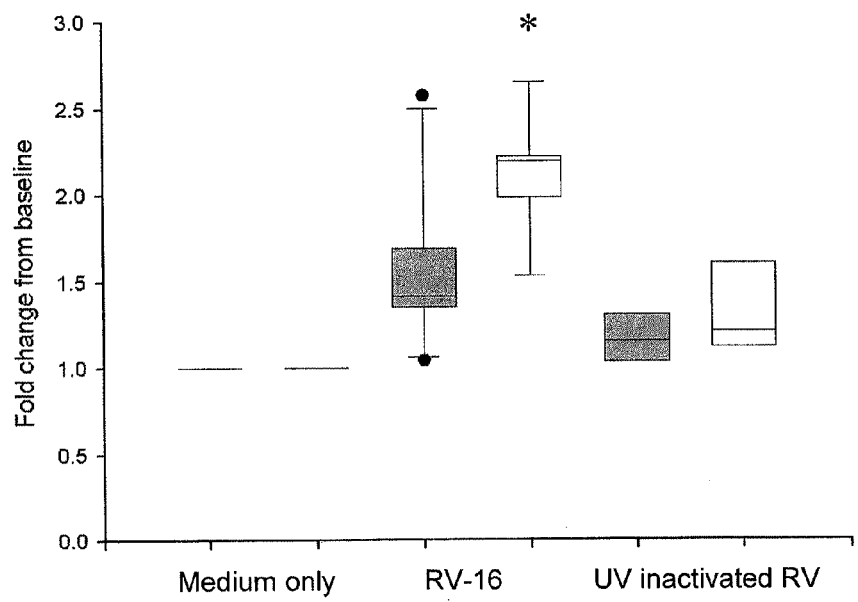
Figure 4A:
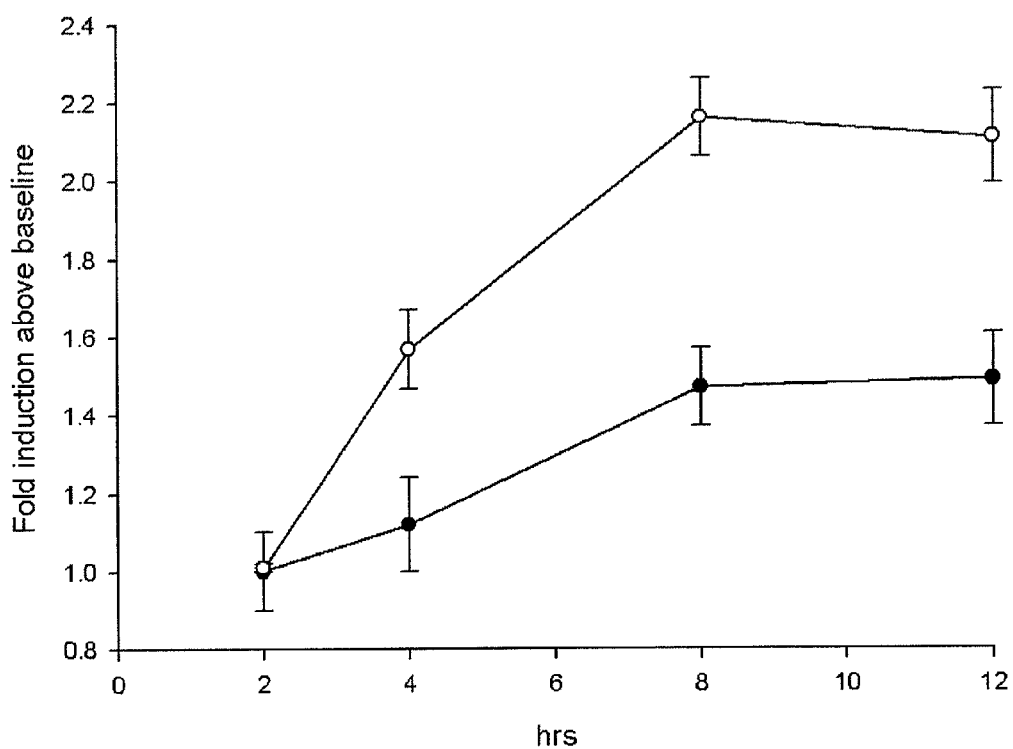
FIGS. 4a-4c show caspase activity and its role following RV-16 infection. Panel (a): The time course for activation of Caspase 3/7 by RV-16 was determined using the Apo-One Homogenous Caspase 3/7 assay (Promega, Maddison, USA) with the readout adjusted for cell number. Values have been log transformed to enable them to be plotted over time; data points represent the geometric mean and the standard error of the mean. There was significant induction of active caspase 3/7 in response to infection reaching a plateau at 8 h (p<0.01). Asthmatic cells showed a lower induction of active caspase 3/7 (mean (SEM)=1.47 (0.1)) compared to healthy controls (mean (SEM)=2.16 (0.3); p=0.004). Panel (b): The effect of inhibition of caspase-3 using the inhibitor, ZVD-fmk, was measured by flow cytometry, as described in the legend to FIG. 3. Cells were treated with RV-16 alone or with ZVD-fmk, before and after infection with RV-16. Results are expressed as the fold induction in apoptosis seen above control cells treated with medium alone. In asthmatic cells were there was a median (IQR) induction of apoptosis above baseline of 1.4 (1.35, 1.68) with RV-16 alone; pre-treatment of cells with the ZVD-fmk, had little effect on apoptosis (median (IQR)=1.17 (0.96, 1.95); p>0.05). However, in healthy controls cells, RV-16 infection resulted in a median (IQR) induction of apoptosis above baseline of 2.19 ((1.98, 2.22) and this was abolished by pretreatment with ZVD-fmk (median (IQR)=0.82 (0.78, 0.86); p=0.03). Panel (c): The effect of caspase-3 inhibition on RV-16 production was measured by HeLa titration assay on the BEC supernatant removed after 48 h of infection. There was no difference seen in the TCID$_{50}$ in the supernatant removed from asthmatic cells infected with RV-16 (median (IQR)=3.56 (3.50-3.62) compared to infected cells treated with ZVD-fmk (median (IQR)=3.56 (3.5-3.62); p=0.94). However for healthy control BECs, the TCID$_{50}$ increased from a median (IQR) value of 0.6(0.4, 0.63) with infection alone to 2.78 (0.63, 6.32) (p=0.01) in the presence of RV-16 and ZVD-fmk. *=significantly different from asthmatic cells ((p<0.01). **=significantly different from cells treated with RV-16 alone. Asthma =●, Healthy controls =○.

As apoptosis is a natural defence that protects cells against virus replication, we characterised the nature of cell death in response to RV-16 using Annexin-V (AxV) and the nuclear stain, 7-aminoactinomycin D (7AAD), to discriminate phosphatidyl serine which has been externalised on the outer leaflet of apoptotic cells. Flow cytometric analysis revealed that there was a significant reduction in viable (ie. $AxV^-$/$7AAD^-$ cell number 8 h following RV-16 infection of normal BECs. This was not seen in cells treated with medium alone or UV inactivated RV-16 suggesting a direct link between infection and cell death (FIG. 3a). In contrast, infection of asthmatic BECs with RV-16 had a smaller effect on viability at 8 h (FIG. 3a). By comparing AxV+/7AAD− cells (ie. apoptotic cells) and AxV+/7AAD+ cells (ie. necrotic cells), the difference in overall viability between normal and asthmatic BECs was found to be due to a significant increase in apoptosis in the normal cultures (FIG. 3b). The induction of apoptosis in infected cells was confirmed by demonstrating altered mitochondrial membrane permeability using the ApoAlert Mitochondrial Membrane sensor (Clontech, Palo Alto Calif., USA) (data not shown) and by measuring activation of active caspase 3/7. In the latter case, there was significantly less active caspase in asthmatic BECs infected with RV-16 than normal BECs (FIG. 4a).

Effects of Inhibition of Apoptosis and RV-16 Production

Figure 4B:
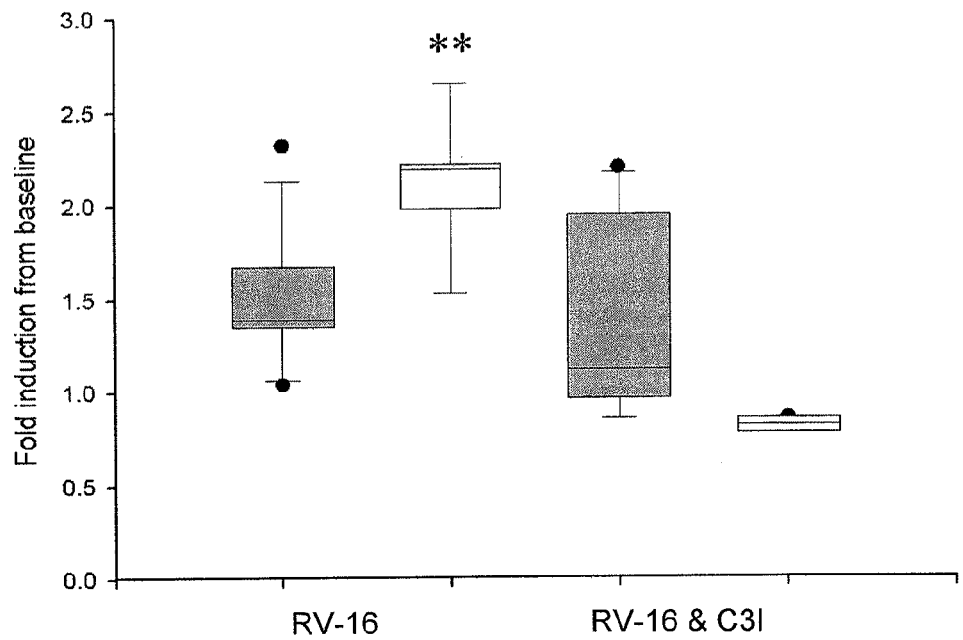
Figure 4C:
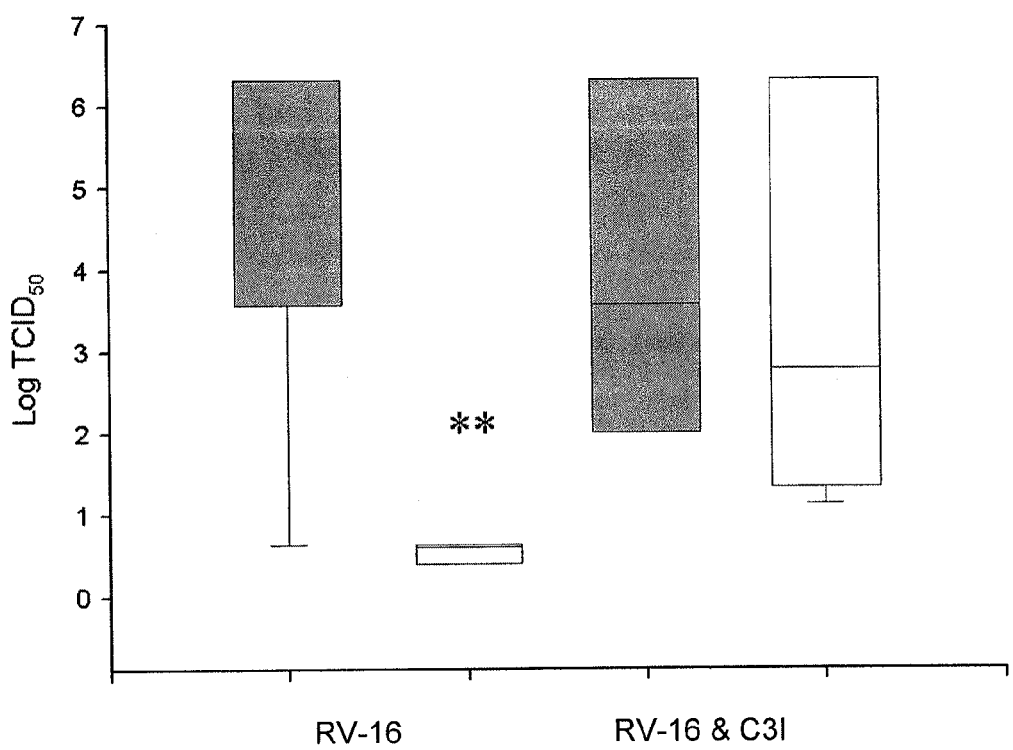

As increased virion production by asthmatic BECs was associated with their ability to by-pass apoptosis, we investigated whether suppression of apoptosis in RV-16 infected normal BECs was sufficient to facilitate virion production. Thus, BECs were treated with the caspase 3 inhibitor (C3I), ZVD-fmk, before and following infection with RV-16. The inhibitor led to a marked reduction in apoptosis in the healthy control cells but had minimal effect on asthmatic cells compared to infection alone (FIG. 4b). Treatment of cells from healthy controls with C3I also had a direct impact on RV-16 production, with a significant increase in transmissible infection at 48 h, a similar increase was not seen in asthmatic cells treated with C3I (FIG. 4c). These data provided a direct link between inhibition of early apoptosis and increased viral yield.

Evaluation of the Innate Anti-viral Response of Asthmatic Epithelial Cells

Figure 5A:
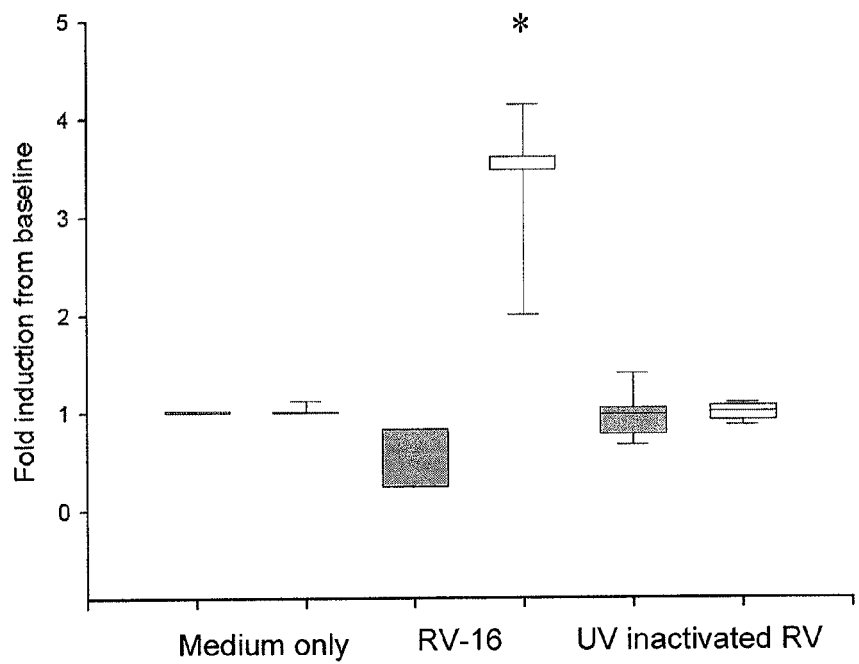
FIGS. 5a-5d show IFNβ production and its role in RV-16 infection. Panel (a): Induction of IFNβ mRNA was measured by qPCR after 8 h of RV-16 infection. Asthmatic cells demonstrated a median (IQR) fold induction from baseline control of 0.3 (0.3, 0.8) which was not significantly different from cells treated with medium alone or UV inactivated RV-16 but was significantly less when compared to healthy controls 3.6 (3.4, 3.6) (p=0.004). Panel (b): Release of IFNβ into culture supernatants 48 h post infection was measured by ELISA. For asthmatic BECs, median (IQR) IFNβ levels were 721 (464, 1290) pg/ml, compared to 1854 pg/ml (758, 3766) (p=0.03) in healthy controls. Both groups demonstrated a significant increase above cells treated with medium alone (56.4 pg/ml, p<0.001) and UV inactivated RV-16 (113.8 pg/ml, P<0.01). Panel (c): The effect of IFNβ on induction of apoptosis in RV-16 infected asthmatic cells was measured by FACS analysis as described in the legend to FIG. 3. Asthmatic cells were either pre-treated with IFNβ (100IU) for 12 h or exposed to RV-16 and then treated with IFN-β. To mimic the presence of viral RNA, cells were also exposed to poly(I):poly(C) a synthetic double stranded RNA oligonucleotide, instead of RV-16. Results are expressed as the fold induction in apoptosis seen above control cells treated with medium alone. There was significant increase in apoptosis in cells exposed to either IFN-β or RV-16 alone (median (IQR) induction of apoptosis =1.11 (0.99, 1.94) or 1.57 (0.98, 1.98), respectively. Cells treated with RV-16 and IFNβ together showed a tendency to increased apoptosis (median (IQR)=3.75 (1.12, 5.25); p=0.11) while those pre-treated with IFN-β and then infected had a significant increase in induction of apoptosis (median (IQR)=5.69 (2.19, 5.69)). Cells exposed to poly(I):poly(C) alone showed a small increase in apoptosis (median (IQR)=1.92 (1.34, 4)) which was enhanced by treatment with IFN-β (median (IQR)=5.56 (3.15, 5.56)) or pre-treatment with IFN-β (median (IQR)=9.25 (3.46, 9.25); p<0.05). Panel (d): The effect of IFNβ on viral yield from asthmatic cells was measured by HeLa titration assay using asthmatic BEC culture supernatants removed after 48 h of infection. Cells were either pre-treated with IFNβ (100IU) for 12 h and then exposed to RV-15 or were treated with IFNβ immediately following infection. There was a significant reduction in viral yield seen in cells treated with IFNβ following infection median log TCID$_{50}$ 2.78 (2, 3.56) and a further reduction in cells pre-treated with IFNβ1.12 (0.28, 1.34) compared to cells infected with RV-16 alone 3.56 (3.5-3.62) (p<0.05). *=significantly different from medium alone and asthmatic cells treated with RV-16. **=significantly different from medium alone. #=significantly different from RV-16 infection alone. ##=significantly different from poly(I):poly(c) alone.
Figure 5B:
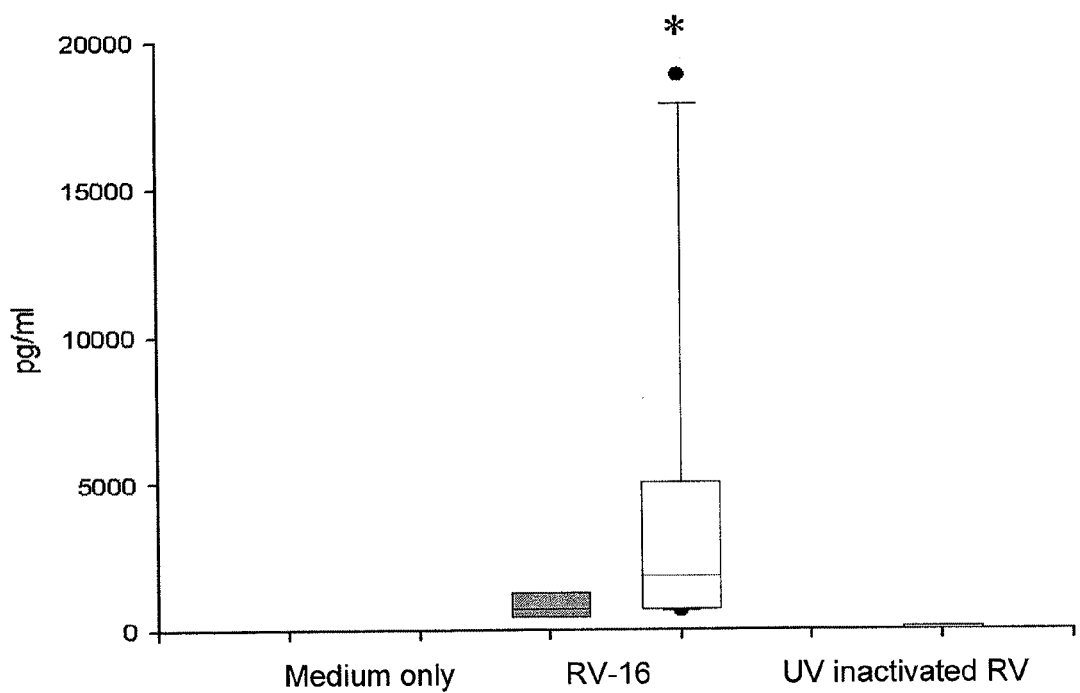
Figure 5C:
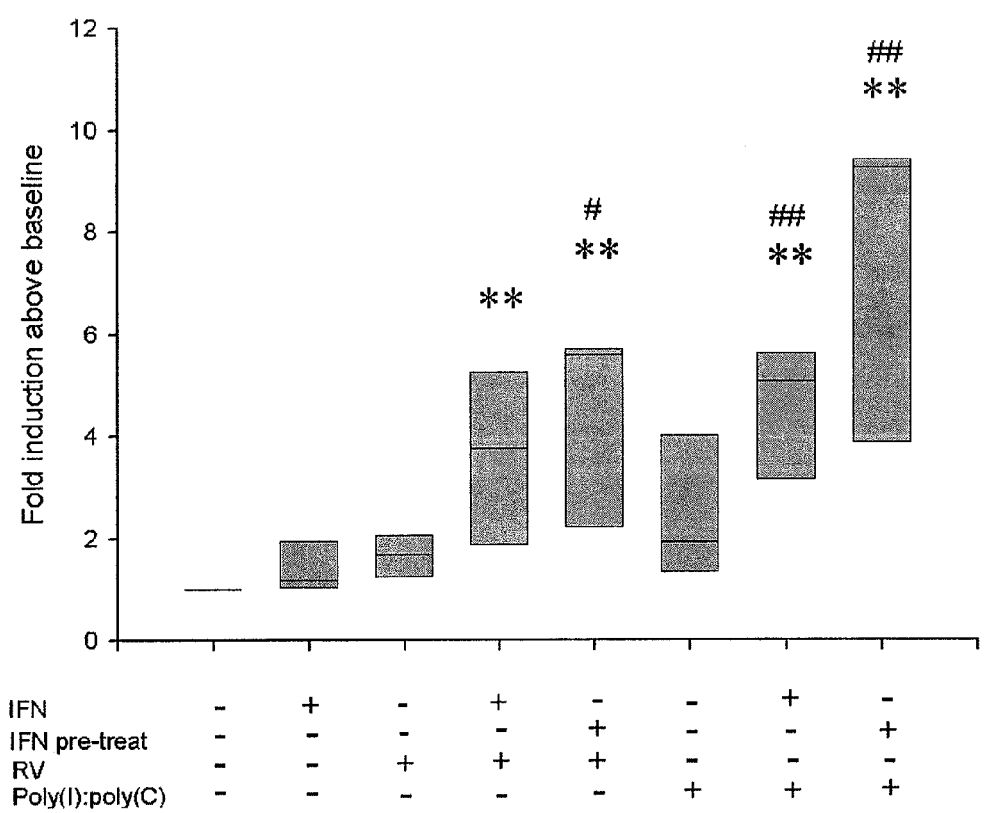
Figure 5D:
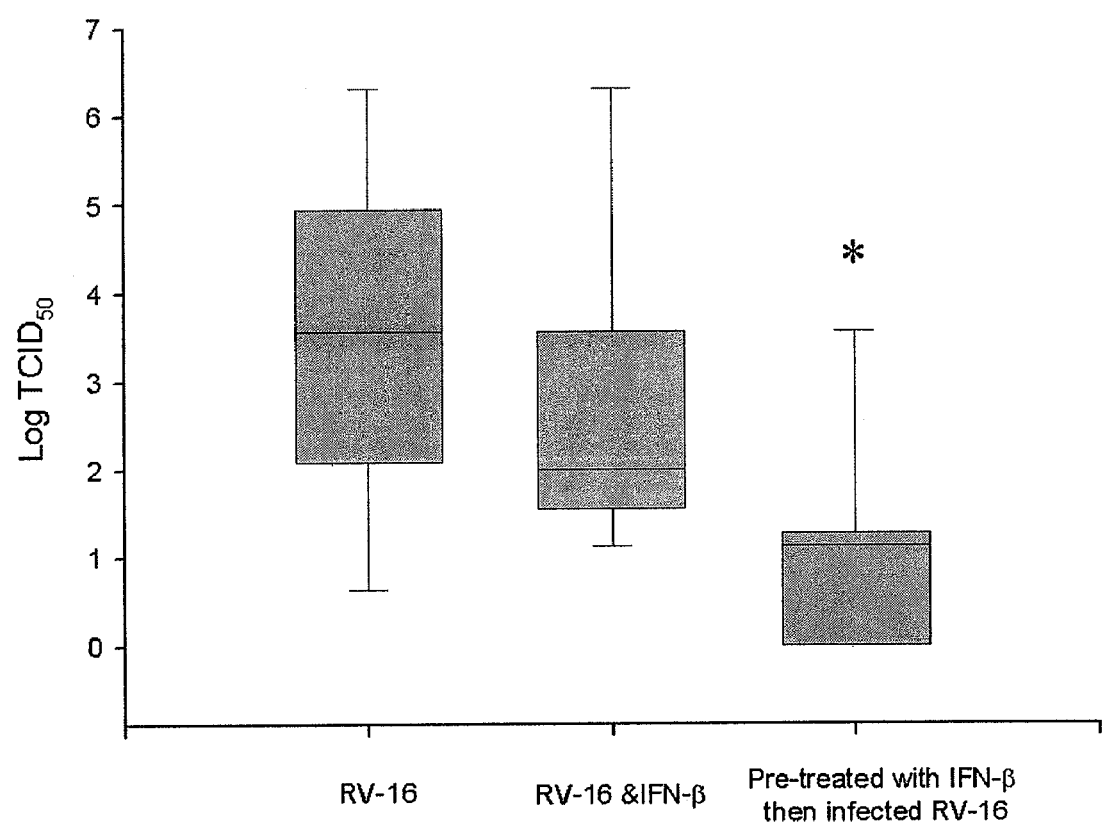

To investigate the underlying mechanism linked to the abnormal anti-viral response by asthmatic BECs, we analysed expression of the type I interferon (IFN), IFN-β, which has been implicated as key regulator of apoptosis in response to virus infection (Samuel, Clin Microbiol Rev, 2001; 14: 778-809; Takaoka et al., Nature, 2003; 424: 516-523). As observed with the proinflammatory cytokines, there was a significant increase in IFN-β mRNA expression by normal BECs 8 h post RV-16 infection, however a similar increase was not seen in asthmatic cells (FIG. 5a); there was also less IFN-β production by asthmatic cells 48 h post RV-16 infection (FIG. 5b). To confirm that this difference in IFN-β production was functionally relevant, we tested the ability of exogenous IFN-β to induce apoptosis in RV-16 infected asthmatic BECs. FIG. 5c shows that pre-treatment of cells with IFN-β (100IU) with RV-16 caused a doubling in the number of apoptotic cells. IFN-β alone had no significant effect on the apoptotic index, but caused a marked induction of apoptosis in response to exposure to synthetic poly(I):poly(C), indicating a requirement for other signals involving recognition of double stranded RNA for commitment to apoptosis in response to IFN-β. In line with its ability to induce apoptosis of virally infected asthmatic BEC, IFN-β caused a significant reduction in RV-16 infectious virion production (FIG. 5d).

These results provide for the first time explanation for the tendency of asthmatic subjects to have lingering lower respiratory tract problems as a consequence of RV infection. Thus, regardless of asthmatic state, spread of RV from the upper to the lower respiratory tract can result in infection of bronchial epithelial cells and induction of an acute inflammatory response. While further infection is limited in non-asthmatic subjects by an innate antiviral response and induction of apoptosis in infected cells, a deficiency of IFN-β in asthma facilitates virion replication and cytolysis with adverse outcomes. These include increased risk of infection of neighbouring cells and an exaggerated inflammatory response in response to the cytolytic effects of the virus. Crucially, this defect can be restored in vitro by provision of exogenous IFN-β, which can provide a brake on viral replication and minimise the self-perpetuating cycle of infection and inflammation. It follows that IFN-β, or agents that induce IFN-β, can be expected to have therapeutic utility during a virally-induced exacerbation of asthma.

EXAMPLE 2

Study of Bronchial Epithelial Cells from COPD Patients

Chronic obstructive pulmonary disease is another example of an inflammatory airways disease in which the common cold virus causes exacerbations (Seemungal T A, Harper-Owen R, Bhowmik A, Jeffries D J, Wedzicha J A. Detection of rhinovirus in induced sputum at exacerbation of chronic obstructive pulmonary disease. Eur Respir J. (2000) 16, 677-83)_with those affected frequently requiring_hospitalization (MacNee W. Acute exacerbations of COPD. Swiss Med. Wkly. (2003) May 3; 133 (17-18):247-57). Based on the finding that bronchial epithelial cells from asthmatic subjects have a defective Type I interferon response, it was postulated that a similar deficiency in COPD could also explain the severity of lower respiratory tract symptoms in this group of patients. To investigate this possibility, archival samples of cultured bronchial epithelial cells were tested for their response to RV-16 infection. These cells were grown from bronchial brushings harvested from two subjects with COPD (one male and one female, ages 61 and 57) and an age matched control without COPD (male, aged 64). The brushings were cultured as described for the asthma studies, except that at passage 0 the cells were cryopreserved at −170 to −180° C. in BEGM medium containing 10% DMSO as a cryoprotective agent. Cryopreservation is routinely used for long-term storage of cell cultures.

When required for experimentation, the frozen cell cultures were rapidly thawed into 1 ml of prewarmed BEGM and then reseeded into culture flasks containing fresh medium to allow expansion to passage 2, as for the cultures of bronchial epithelial cells from normal and asthmatic subjects described in example 1. At passage 2, the cells were seeded onto 12 well trays and cultured until 80% confluent. They were then exposed to RV-16 using the same protocols described above.

Figure 6:
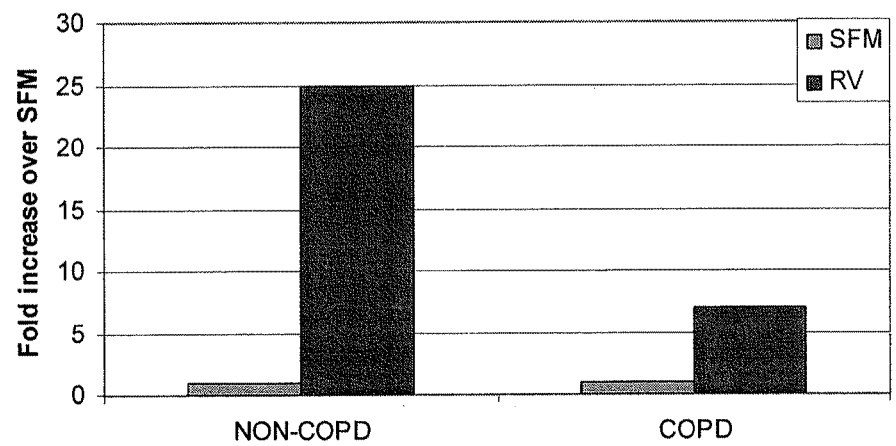
FIG. 6 shows induction of IFN-β mRNA 8 hours after infection of primary BEC cultures from a non-COPD volunteer and a COPD patient with RV-16 (2 moi). IFN-β mRNA was measured by reverse transcription quantitative PCR and normalised to IFN-β levels in untreated (SFM) controls.
Figure 7:
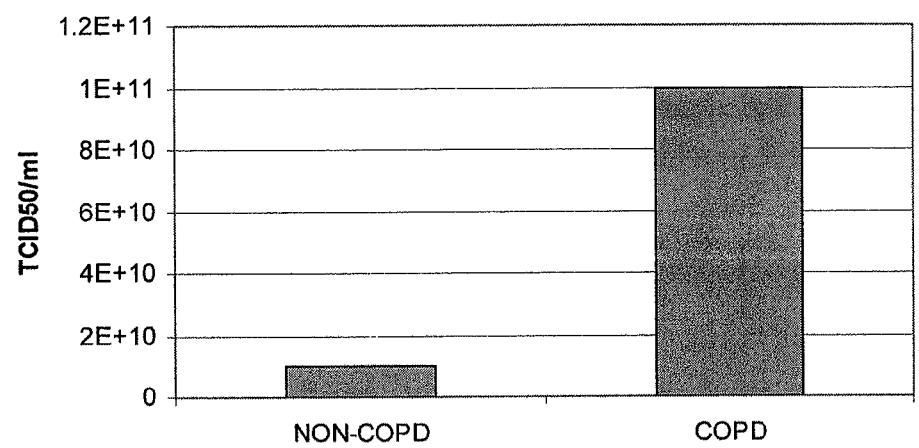
FIG. 7 shows a comparison of viral replication 24 hours after RV-16 infection (2 moi) of BEC cultures from a non-COPD and a COPD patient. Virion production was measured as TCID$_{50}$/ml as determined by HeLa cell titration assay.

To compare the innate immune response of primary BEC cultures from a COPD and a non—COPD patient, induction of IFN-β mRNA was measured in response to infection with RV-16 (2 moi). As shown in FIG. 6, the BECs from the non-COPD patient showed a 25-fold induction of IFNβ mRNA 8 hours after RV-16 infection whereas the response from the COPD BECs was less than one-third of this. Consistent with this poor innate immune response, virion production at 24 hours was an order of magnitude greater in the cells from the COPD subject (FIG. 7).

Figure 8:
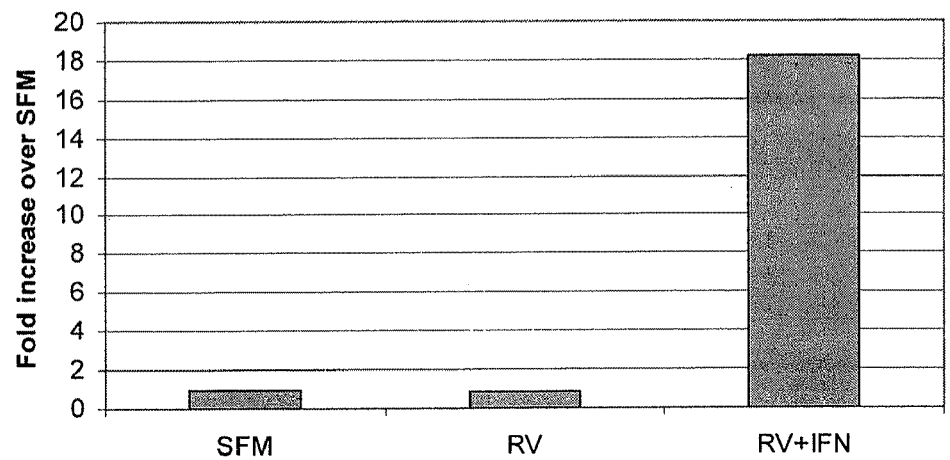
FIG. 8 shows induction of IFN-β mRNA 8 hours after infection of primary BECs from a COPD patient with RV-16

It was next tested whether exogenous IFN-β could protect BECs from a COPD patient against virus replication. As shown in FIGS. 8 and 9, cells from a second COPD patient also showed poor induction of IFN-β in response to RV-16 infection. However, they were able to respond to exogenous IFN-β with a vigorous induction of IFN-β mRNA. This was accompanied by a marked suppression of RV-16 replication, with a one hundred fold reduction in $TCID_{50}$ which was less than that seen in the cells from the non-COPD volunteer.

These results suggest that, as found in the above-described studies of BECs from asthmatic subjects, BECs from COPD patients also have a poor innate immune response. This would help to explain why these patients have lingering lower respiratory tract problems as a consequence of RV infection. Based on the fact that IFN-β can induce its own expression and suppress RV-16 replication, it follows that IFN-β, or agents that induce IFN-β, can be expected to have therapeutic utility during a virally-induced exacerbation of COPD, as well as asthma.

EXAMPLE 3

Rhinovirus Induces IFN-λs in Bronchial Epithelial Cells

Aim:

Investigate whether RV induces IFN-λs in vitro and whether IFN-λs induce antiviral activity against RV infection in bronchial epithelial cells.

Outline of Methods:

The human bronchial epithelial cell-line BEAS2B was infected with RV. TaqMan® PCR was used to identify IFN-λs mRNA expression and a bioassay was employed for corresponding protein production. BEAS2B cells were treated for 24 h with different doses of IFN-λ1 before infection with RV. Both TaqMan® PCR for viral RNA in cell lysates and viral titration of the BEAS2B supernatant were performed to investigate the antiviral effect.

Results:

IFN-λ1, IFN-λ2 and IFN-λ3 mRNA was increased after 4 h ($p<0.05$) and peaked at 8 h post-infection ($p<0.001$). The increase was demonstrated to be dose-responsive to RV-16 at 24 h post-infection ($p<0.001$). Infection with RV-9 and RV-1B demonstrated that the response was serotype and receptor independent. UV-inactivation of RV-16 completely inhibited the up-regulation, indicating that active viral replication is required. EMSA assay detected the presence of IFN-λs proteins in the supernatant of BEAS2B 24 h after the infection. Finally both TaqMan® PCR for viral RNA in cell lysates ($p<0.001$) and viral titration ($p<0.001$) showed a dose-dependent anti-viral effect of IFN-λ1 to RV16 infection.

Conclusions:

This study demonstrated that RV infection of bronchial epithelial cell-line leads to the production of IFN-λs and that these proteins may play an important role in the antiviral response to RV.

EXAMPLE 4

Viral Infection in Asthma Exacerbations: Role of Interferon Lambda

Aim:

Investigate whether RV16 induces IFN-λs and if this production is associated with increased susceptibility to rhinovirus infections in asthmatics.

Methods:

The human bronchial epithelial cell-line BEAS2B and bronchial primary cells from asthmatics (6) and normal patients (5) were infected with RV16. TaqMan® PCR for IFN-λ mRNA expression was used. BEAS2B cells were treated with IFN-λ1 before infection with RV16. Both TaqMan® PCR for viral RNA in cell lysates and viral titration of the BEAS2B supernatant were performed to investigate the antiviral effect. TaqMan® PCR for viral RNA in cell lysates of primary cells was used also to test weather RV16 infectivity was different between primary cells from asthmatics and normals.

IFN-λs in increasing susceptibility to rhinovirus infections in asthmatics. Results: IFN-λs mRNA was increased both in BEAS2B and in primary cells with the peak at 8 h infection. In BEAS2B both TaqMan® PCR for viral RNA and viral titration showed a dose-dependent anti-viral effect of IFN-λ1 to RV16 infection. Primary bronchial epithelial cells produced significantly lower amount of IFN-λ after RV16 infection ($p<0.05$) as compared to normal controls. Conversely RV16 replication was higher ($p<0.05$) in bronchial epithelial cells from asthmatic subjects.

Conclusions:

RV16 infection of bronchial epithelial cells leads to the production of IFN-λs. This production is deficient in asthmatic subjects and may thus be a factor in increasing susceptibility to rhinovirus infections in asthmatics.

Further Materials and Methods

Obtaining of Primary Bronchial Epithelial Cells

All subjects were nonsmokers, with no exacerbations or respiratory tract infections in the preceding 4 wk. Allergy skin tests used a panel of common aeroallergens and were considered positive if the wheal response was >3 mm than the negative control. Lung function was assessed by spirometry and bronchial hyperresponsiveness by histamine challenge. Asthma was diagnosed in atopic individuals with a consistent history and evidence of bronchial hyperresponsiveness (defined by a PC20 histamine <8 mg/ml) and was categorized in accordance with the GINA guidelines (National Heart, Lung and Blood Institute. 1995. Global Strategy for Asthma Management and Prevention. 96-369). Healthy controls had no previous history of lung disease, normal lung function, no evidence of bronchial hyperresponsiveness, and were non-atopic. The study was approved by the Southampton University Hospital Ethics Committee. All subjects gave written informed consent.

Bronchial Epithelial Cell Tissue Culture

Primary BECs were grown from bronchial brushings (>95% epithelial cells), which were obtained by fiber-optic bronchoscopy in accordance with standard guidelines (Hurd, S.Z. 1991. J. Allergy Clin. Immunol. 88:808-814); there was no significant difference in the proportion of columnar and basal cells isolated from normal or asthmatic donors. Cell culture and characterization was performed as described previously (Bucchieri, F., J. Lordon, A. Richter, D. Buchanan, R. Djukanovic, S. T. Holgate, and D. E. Davies. 2001. Am. J. Respir. Cell Mol. Biol. 27:179-185; Lordan, J. L., F. Bucchieri, A. Richter, A. Konstantinidis, J. W. Holloway, M. Thornber, S. M. Puddicombe, D. Buchanan, S. J. Wilson, R. Djukanovic, et al. 2002. J. Immunol. 169:407-414). The cultured cells were all cytokeratin positive and exhibited a basal cell phenotype, as evidenced by the expression of cytokeratin 13, irrespective of the type of donor of the original brushings. Primary cultures were established by seeding freshly brushed BECs into hormonally supplemented bronchial epithelial growth medium (Clonetics) containing 50 U/ml penicillin and 50 μg/ml streptomycin. At passage two, cells were seeded onto 12-well trays and cultured until 80% confluent (Bucchieri et al supra) before exposure to RV-16.

Generation and Titration of RV

RV-16 stocks were generated and titrated from infected cultures of Ohio HeLa cells as described previously (Papi, A., and S. L. Johnston. 1999 J. Biol. Chem. 274:9707-9720). Cells were infected at a multiplicity of infection of 2. Confirmation of infection and quantification of viral production was assessed by HeLa titration assay (Papi, A., and S. L. Johnston, supra) and reverse transcription quantitative polymerase chain reaction (RT-qPCR), as described below. As negative controls, cells were treated with medium alone and UV inactivated RV-16 (Papi, A., and S. L. Johnston, supra).

RT-qPCR and ELISA

RT-qPCR analysis of IFNλ mRNA and RV-16 viral RNA (vRNA) gene expression was performed on DNase treated RNA extracted from BECs using TRIzol (Life Technologies). Total RNA (1 μg) was reverse transcribed using avian myeloblastosis virus transcriptase (Promega) and random hexamers for IFNλ mRNA and 18S rRNA analysis or oligo (dT)15 for RV-16 vRNA. Real-time detection used an iCyclerIQ detection system using a PCR protocol as follows: 42 cycles at 95° C. for 15 s, 60° C. for 1 min and 72° C. for 15 s. IFNλ signals were normalized to 18S rRNA and relative quantification performed using the ΔΔCT method. Comparisons were made 8 h after infection. Quantification of RV-16 was achieved using a TAQman assay located in the 5' UTR in conjunction with the standard curve method. The standard curve was constructed using 10-fold serial dilutions of RV-16 5' NTR cDNA cloned into PCR 2.1 TOPO (Invitrogen). Relative values for RV detection were calculated by normalizing to the starting cell number. Probe: FAM/TAMRA 6-FAMT-GAGTCCTCCGGCCCCTGAATG (SEQ ID NO:28), forward primer (RVTM-1) 5'-GTGAAGAGCCSCRTGTGCT-3' (SEQ ID NO:26), reverse primer (RVTM-2) 5'-GCTSCAGGG-TTAAGGTTAGCC-3' (SEQ ID NO:27).

Statistical Analysis

When data were normally distributed the mean and SD have been used, differences between groups have been analyzed using Student's t test, when not normally distributed data were analyzed using nonparametric equivalents and summarized using the median and IQR, multiple comparisons were first analyzed by the Kruskal Wallis test and then by individual testing if significant. Correlations were analyzed by Spearman's test. A p-value of <0.05 was considered significant.

Diagnosis of Asthma and COPD (i) Diagnosing COPD

The following information was taken from a publication titled: "Pocket guide to COPD diagnosis, management and prevention: a guide for heath care professionals", which is available from www.goldcopd.com.

A diagnosis of COPD should be considered in any individual who presents characteristic symptoms and a history of exposure to risk factors for the disease, especially cigarette smoking.

Key Indicators for Considering a COPD Diagnosis

Chronic cough: Present intermittently or every day. Often present throughout the day; seldom only nocturnal.

Chronic sputum production: Any pattern of chronic sputum production may indicate COPD.

Acute bronchitis: Repeated episodes.

Dyspnea that is: Progressive (worsens over time). Persistent (present every day). Worse on exercise. Worse during respiratory infections.

History of exposure to risk factors: Tobacco smoke (including popular local preparations). Occupational dusts and chemicals. Smoke from home cooking and heating fuel.

The diagnosis should be confirmed by spirometry. Where spirometry is unavailable, the diagnosis of COPD should be made using all available tools. Clinical symptoms and signs (abnormal shortness of breath and increased forced expiratory time) can be used to help with the diagnosis. A low peak flow is consistent with COPD but has poor specificity since it can be caused by other lung diseases and by poor performance. In the interest of improving the accuracy of a diagnosis of COPD, every effort should be made to provide access to standardized spirometry.

When performing spirometry, measure:
Forced Vital Capacity (FVC) and
Forced Expiratory Volume in one second (FEV1).

Calculate the FEV1/FVC ratio. Spirometric results are expressed as % Predicted using appropriate normal values for the person's sex, age, and height.

Patients with COPD typically show a decrease in both FEV1 and FEV1/FVC. The degree of spirometric abnormality generally reflects the severity of COPD. However, both symptoms and spirometry should be considered when developing an individualized management strategy for each patient.

Classification of COPD by Severity

Stage 0: At Risk—Chronic cough and sputum production; lung function is still normal.

Stage I: Mild COPD—Mild airflow limitation (FEV1/FVC<70% but FEV1 >80% predicted) and usually, but not always, chronic cough and sputum production.

At this stage, the individual may not be aware that his or her lung function is abnormal.

Stage II: Moderate COPD—Worsening airflow limitation (50%<FEV1 <80% predicted), and usually the progression of symptoms, with shortness of breath typically developing on exertion.

Stage III: Severe COPD—Further worsening of airflow limitation (30%<FEV1 <50% predicted), increased shortness of breath, and repeated exacerbations which have an impact on patients' quality of life.

Exacerbations of symptoms, which have an impact on a patient's quality of life and prognosis, are especially seen in patients with FEV1<50% predicted.

Stage IV: Very Severe COPD—Severe airflow limitation (FEV1 <30% predicted) or FEV1 <50% predicted plus chronic respiratory failure. Patients may have very severe (Stage IV) COPD even if the FEV1 is >30% predicted, whenever these complications are present.

At this stage, quality of life is very appreciably impaired and exacerbations may be life-threatening.

Differential Diagnosis

A major differential diagnosis is asthma. In some patients with chronic asthma, a clear distinction from COPD is not possible using current imaging and physiological testing techniques. In these patients, current management is similar to that of asthma. Other potential diagnoses are usually easier to distinguish from COPD:

Below are listed suggestive features that may be used to distinguish a number of different disorders. These features tend to be characteristic of the respective diseases, but do not occur in every case. For example, a person who has never smoked may develop COPD (especially in the developing world, where other risk factors may be more important than cigarette smoking); asthma may develop in adult and even elderly patients.

Differential Diagnosis of COPD

COPD: Onset in mid-life. Symptoms slowly progressive.
Long smoking history.
Dyspnea during exercise.
Largely irreversible airflow limitation.

Asthma: Onset early in life (often childhood).
Symptoms vary from day to day.
Symptoms at night/early morning.
Allergy, rhinitis, and/or eczema also present.
Family history of asthma.
Largely reversible airflow limitation.

Congestive Heart

Failure: Fine basilar crackles on auscultation.
Chest X-ray shows dilated heart, pulmonary edema.
Pulmonary function tests indicate volume restriction, not airflow limitation.

Bronchiectasis: Large volumes of purulent sputum.
Commonly associated with bacterial infection.
Coarse crackles/clubbing on auscultation.
Chest X-ray/CT shows bronchial dilation, bronchial wall thickening.

Tuberculosis: Onset all ages.
Chest X-ray shows lung infiltrate or nodular lesions.
Microbiological confirmation.
High local prevalence of tuberculosis.

(ii) Diagnosing Asthma

The following information was taken from a publication titled: "Pocket guide for asthma prevention and management", which is available from www.ginasthma.com.

Asthma can often be diagnosed on the basis of symptoms. However, measurements of lung function, and particularly the reversibility of lung function abnormalities, greatly enhance diagnostic confidence.

Is it Asthma?

Consider asthma if any of the following signs or symptoms are present.

Wheezing-high-pitched whistling sounds when breathing out-especially in children. (A normal chest examination does not exclude asthma.)

History of any of the following:
Cough, worse particularly at night
Recurrent wheeze
Recurrent difficult breathing
Recurrent chest tightness.

(Note: Eczema, hay fever or a family history of asthma or atopic diseases are often associated with asthma.)

Symptoms occur or worsen at night, awakening the patient.

Symptoms occur or worsen in the presence of: Animals with fur, Exercise, Aerosol chemicals, Pollen, Changes in temperature, Respiratory (viral) infections, Domestic dust mites, Smoke, and/or Drugs (aspirin, beta blockers).

Strong Emotional Expression

Reversible and variable airflow limitation—as measured by using a spirometer (FEV1 and FVC) or a peak expiratory flow (PEF) meter. When using a peak flow meter, consider asthma if:
  PEF increases more than 15 percent 15 to 20 minutes after inhalation of a rapid-acting_2-agonist, or
  PEF varies more than 20 percent from morning measurement upon arising to measurement 12 hours later in patients taking a bronchodilator (more than 10 percent in patients who are not taking a bronchodilator), or
  PEF decreases more than 15 percent after 6 minutes of sustained running or exercise.
Peak Flow Meters: Uses and Technique
Lung function measurements assess airflow limitation and help diagnose and monitor the course of asthma.
To assess the level of airflow limitation, two methods are used. Peak flow meters measure peak expiratory flow (PEF), and spirometers measure forced expiratory volume in 1 second (FEV1) and its accompanying forced vital capacity (FVC). The accuracy of all lung function measurements depend on patient effort and correct technique.
Several kinds of peak flow meters and spirometers are available, and the technique for use is similar for all. To use a peak flow meter:
  Stand up and hold the peak flow meter without restricting movement of the marker. Make sure the marker is at the bottom of the scale.
  Take a deep breath, put the peak flow meter in your mouth, seal your lips around the mouthpiece, and breathe out as hard and fast as possible. Do not put your tongue inside the mouthpiece.
  Record the result. Return the marker to zero.
  Repeat twice more. Choose the highest of the three readings.
Daily PEF monitoring for 2 to 3 weeks is useful, when it is available, for establishing a diagnosis and treatment. If during 2 to 3 weeks a patient cannot achieve 80 percent of predicted PEF (predicted values are provided with all peak flow meters), it may be necessary to determine a patient's personal best value, e.g. by a course of oral glucocorticosteroid.
Long-term PEF monitoring is useful, along with review of symptoms, for evaluating a patient's response to therapy. PEF monitoring can also help detect early signs of worsening before symptoms occur.
Note: Examples of available peak flow meters and instructions for use of inhalers and spacers can be found on www.ginasthma.org.
Diagnostic Challenges Include the Following:
Young children whose primary symptom is recurrent or persistent cough or who wheeze with respiratory infections are often misdiagnosed as having bronchitis or pneumonia (including acute respiratory infection—ARI) and thus ineffectively treated with antibiotics or cough suppressants. Treatment with asthma medication can be beneficial and diagnostic.
Many infants and young children who wheeze with viral respiratory infections may not develop asthma that persists through childhood. But they may benefit from asthma medications for their wheezing episodes. There is no certain way to predict which children will have persistent asthma, but allergy, a family history of allergy or asthma, and perinatal exposure to passive smoke and allergens are more strongly associated with continuing asthma.
Asthma should be considered if the patient's colds repeatedly "go to the chest" or take more than 10 days to clear up, or if the patient improves when asthma medication is given.
Tobacco smokers and elderly patients frequently suffer from chronic obstructive pulmonary disease (COPD) with symptoms similar to asthma. Yet they may also have asthma and benefit from treatment. Improvement in PEF after asthma treatment is diagnostic.
Workers who are exposed to inhalant chemicals or allergens in the workplace can develop asthma and may be misdiagnosed as having chronic bronchitis or chronic obstructive pulmonary disease. Early recognition (PEF measurements at work and home), strict avoidance of further exposure, and early treatment are essential.
Asthma attacks may be difficult to diagnose. For example, acute shortness of breath, chest tightness and wheezing can also be caused by croup, bronchitis, heart attacks, and vocal cord dysfunction. Using spirometry, establishing reversibility of symptoms with bronchodilators, and assessing the history of the attack (e.g. whether it was related to exposures that commonly make asthma worse) aid the diagnosis. A chest x-ray can help rule out infection, large airway lesions, congestive heart failure, or aspiration of a foreign object.

EXAMPLE 5

Expression of Alpha-interferons, Beta-interferons and Lambda-interferons in Epithelial Cells and PBMCS after Respiratory Virus Infections In this study, the potential of different cell types such as BEAS-2B, human bronchial epithelial cells (HBEC) and PBMC (as a model for macrophages) to express and produce various type 1 and type III interferons upon respiratory virus infection was investigated. Sets of primers and probes were designed for quantitive PCR of various type 1 and type III interferons. In BEAS-2B cells induction of IFN-α mRNA expression was detected by 8 hours from 0-time point, induction of IL-29 mRNA from 0-time point was detected by 8-hours with peak at 24 hours and induction of IFN-β from 0-time point was detected by 24 hours. By ELISA we also observed production of IL-29 and IFN-β protein by 24 hours. In HBEC induction of IFNα mRNA expression was detected by 8 hours from 0-time point and induction of IL-29 mRNA from 0-time point by 24 hours. In PBMC induction of IFNA, IL-29 and IFNB mRNA expression by 8 hours from 0-time point were demonstrated. Induction of IFN-α, IFN-β and IL-29 protein by ELISA was additionally shown.

Additional Information on Rhinoviruses

Rhinoviruses are small RNA viruses. They belong to picornaviridae family. More than 100 serotypes of rhinoviruses have been identified. According to the type of the receptor for binding rhinoviruses are divided into two groups. Major group approximately 90% of all RV serotypes use ICAM-1 molecule and minor group approximately 10% of all RV serotypes use low density lipoprotein receptor (N. G. Papadopoulos, S. L. Johnston: Rhinoviruses. Principles and practice of clinical virology. 5th edition 2004, 361-377).

Recent work indicates that asthmatic individuals are more susceptible to naturally occurring rhinovirus (RV) infection than normal individuals in that lower respiratory tract symptoms and changes in PEF were more severe and of longer (Corne et al., Lancet (2002) 359, 831-834). So the important question is what differences occur in lower airway of asthmatics in comparison to normal subjects during RV infection and lead to asthma exacerbation.

It was demonstrated that in asthmatics RV induces greater severity of lower respiratory symptoms which is accompanied by higher concentrations of inflammatory cells: lymphocytes, NK cells, eosinophils and neutrophils in BAL RV infection induces inflammatory response (IL-6, IL-8, RANTES, IL-16 and upregulation of ICAM-1) in bronchial epithelium (N. G. Papadopoulos, P. J. Bates, P. G. Bardin et al. J Infect Dis 181 (2000), pp. 1875-1884; S. L. Johnston, A. Papi, P. J. Bates, J. G. Mastronarde, M. M. Monick and G. W. Hunninghake, J Immunol 160 (1998), pp. 6172-6181). PBMCs from asthmatics exposed to RV ex vivo demonstrated decreased levels of type I cytokines and increased levels of type 2 cytokines when compared to normals (Papadopoulos et al. Thorax 57 (2002)). Moreover, as already noted above, more recently primary epithelial bronchial cells from asthmatics exposed to RV ex vivo were observed to demonstrate decreased levels of IFN-β when compared to normals (Wark et al. J. Exp. Med. (21 Mar. 2005) 201, 937-947)

As also previously discussed above, Type 1 interferons such as IFN-α, IFN-β and the more recently discovered type III interferons (IFN-λs) play a vital role in innate immune response against viruses. They induce lots of IFN-inducible genes with antiviral properties and as it has been shown recently induce apoptosis in virally infected cells (Takaoka A, Hayakawa S, Yanai H, et al. Nature 2003; 424(6948):516-523).

As there is no small animal model for rhinovirus infection, it is very important to use proper cell cultures which are being infected by rhinoviruses. It is known that rhinovirus infects and replicates in respiratory epithelial cells of lower respiratory tract (N. G. Papadopoulos et al J Med Virol 58 (1999), pp. 100-104). As it is not much known about the induction of type 1 and type III interferons in epithelial cells, in this study we tried to show how different cell types such as primary bronchial epithelial cells, BEAS-2B and PBMC (as a model for macrophages) express and produce various type 1 and type III interferons upon different respiratory virus infection.

Human Bronchial Epithelial Cell Tissue Culture

Human bronchial epithelial cells (HBECs) were purchased from Cambrex, USA. Primary cultures were established by seeding bronchial epithelial cells into hormonally supplemented bronchial epithelial growth medium (BEBM; Cambrex, USA) containing 2 ml BPE, 0.5 ml insulin, HC 0.5 ml, GA-1000 0,5 ml, retinoic acid 0.5 ml, transferrin 0.5 ml, triiodothyronine 0.5 ml, epinephrine 0.5 ml, hEGF 0.5 ml (Cambrex, USA). At passage 1 cells were seeded onto 12 well trays and cultured until 80% confluent (Bucchieri et al., Asthamatic bronchil epithelium is more susceptible to oxidant-induced apoptoisis. Am. J. Respir. Cell Mol. Biol. 27, 179) before exposure to RV-16, RV-1B and influenza virus.

Cell and Viral Culture

The human bronchial epithelial cell line BEAS-2B were cultured in RPMI-1640 supplemented with 10% FCS (Invitrogen). RV serotypes 16 and 1B were grown in HeLa cells and prepared as previously described (Papi and Johnston (1999) Rhinovirus infection induces expression of its own receptor intercellular adhesion molecule 1 (ICAM-1) via increased NF-kB-mediated transcription J. Biol. Chem. 274, 9707-9720) Viruses were titrated on HeLa cells to ascertain their $TCID_{50}$/ml (Johnston and Tyrell (1995) Rhinoviruses, p. 253-263 In Diagnostic procedures for viral, rickettsial and Chlamydial infections, ed Lennette and Schmidt, American Public health Association, Washington, D.C.). The identities of all RVs were confirmed by titration on HeLa cells and neutralisation using serotype-specific antibodies. UV inactivation was performed as previously described (Johnston et al. (1998) Low grade rhinovirus infection induces a prolonged release of IL-8 in pulmonary epithelium. J. Immunol. 160, 6172-6181) and filtered virus was produced by passing RV stocks through a 30 KDa membrane (Millipore) at 10 000 g for 5 min.

Infection of Cells with RV

BEAS-2B cells were cultured in 12-well tissue culture plates (Nalge Nunc) for 24-hours before being placed into 2% FCS RPMI medium for a further 24-hours. Cells were infected with RV for 1-hour with shaking at room temperature, before the virus was removed and replaced with 1 ml of 2% FCS RPMI medium. Cells supernatants and RNA lysates were harvested at the times indicated. Supernatants and lysates were stored at −80° C. until required.

PBMC Separation and Rhinovirus 16 Infection

PBMCs were separated from whole blood using gradient density centrifugations (Sigma). 4×10(6) cells/2 ml were exposed to rhinovirus 16 for 1 hour. At the end of exposure time cells were washed and medium was changed.

RNA Extraction, Reverse Transcription and Taqman® Real-time PCR

RNA was extracted from cells using the RNeasy method following the manufacturers instructions, including the optional DNaseI digestion of contaminating DNA (Qiagen). cDNA was synthesised using Omniscript RT and components as directed by the manufacturer (Qiagen).

Primers were purchased from Invitrogen and probes from Qiagen. TaqMan® analysis of alpha-interpherons, IL-29 and IFNB mRNA was normalised with respect to 18s rRNA. For detecting of alpha-interferons types 1,6 and 13 IFNα.1 set of primers and probe was used (IFNA.1 forward—5'-CAG AGT CAC CCA TCT CAG CA-3 (SEQ ID NO:11), IFNA.1 reverse—5'-CAC CAC CAG GAC CAT CAG TA-3' (SEQ ID NO:12) and 5'-FAM-TAMRA labelled probe—5'-ATC TGC AAT ATC TAC GAT GGC CTC gCC-3') (SEQ ID NO:13). For detecting of alpha-interferons types 2,4,5,8,10,14,17,21 IFNα.2 set of primers and probe was used (IFNα.2 forward—5'-CTG GCA CAA ATG GGA AGA AT-3' (SEQ ID NO:14), IFNA.2 reverse—5'-CTT GAG CCT TCT GGA ACT GG-3' (SEQ ID NO:15) and 5'-FAM-TAMRA labelled probe—5'-TTT CTC CTG CCT GAA GGA CAG ACA Tga-3' (SEQ ID NO:16). For IL-29 detection we used forward primer—5'GGA CGC CTT GGA AGA GTC ACT'3 (SEQ ID NO: 17), reverse—5'-AGA AGC CTC AGG TCC CAA TTC'-3 (SEQ ID NO: 18) and 5'-FAM-TAMRA labelled probe—5'-AGT TGC AGC TCT CCT GTC TTC CCC G-3' (SEQ ID NO:19). For interferon-beta detection we used forward primer—5'-CGC CGC ATT GAC CAT CTA-3' (SEQ ID NO:20), reverse—5'-GAC ATT AGC CAG GAG GTT CTC A-3' (SEQ ID NO:21) and 5'-FAM-TAMRA labelled probe—5'-TCA GAC AAG ATT CAT CTA GCA CTG GCT GGA-3' (SEQ ID NO:22). For 18s, each reaction contained 18STM.1 (CGC CGC TAG AGG TGA AAT TCT) (SEQ ID NO:23), 18STM.2 (CAT TCT TGG CAA ATG CTT TCG) (SEQ ID NO:24), 5'-FAM-TAMRA labelled probe (5'-ACC GGC GCA AGA CGG ACC AGA) (SEQ ID NO:25) and 2 µl cDNA diluted 1/100 in 1× Quantitect Probe PCR Master Mix (Qiagen). The reactions were analysed using an ABI7000 Automated TaqMan (Applied Biosystems). The amplification cycle consisted of 50° C. for 2 minutes, 94° C. for 10 minutes and 40 cycles of 94° C. for 15 seconds, 60° C. for 15 seconds.

Enzyme-Linked Immunosorbent Assay to Evaluate IFN-A, IL-29 and IFNB Release

Interferon-alpha, interferon-beta and IL-29 proteins were quantified by ELISA in supernatants from untreated and infected cell cultures collected and stored at −80° C. using commercially available paired antibodies and standards, following the manufacturers instructions. High Sensitivity Interferon-alpha Human Biotrak ELISA System by Amersham Biosciences for interferon-alpha. Human Interferon-beta ELISA kit was purchased from Fujirebio Inc. All the measurements were done according to manufactures' instructions. The detection limits for described assays are 0.63 pg/ml for interferon-alpha, 2.5 UI/ml for interferon-beta and 0.01 for IL-29.

Quantitative ELISA for IFNλs

ELISA 96 well plates (Nunc Maxisorp) were coated with detecting antibody (100 μl per well of Monoclonal Anti-human IL-29/IFN-λ1 Antibody diluted in PBS from R&D system catalogue number MAB15981 at concentration of 1 μg/ml) and left at room temperature overnight. The next morning plates were washed twice in PBS with 0.1% of Tween 20 and than blocked at room temperature with 220 μl per well of a solution of 2% BSA. After 2 hours plates were washed twice and 100 μl of undiluted samples and 100 μl of standard samples were added in the wells. Samples and standard were both tested in duplicate. Standard was set up in diluent buffer (PBS with 1% BSA and 0.1% Tween 20) using Recombinant Human IL-29/IFN-λ1 from R&D system starting from 3 ng/ml down to approximately 10 pg/ml. 100 mcl of diluent buffer were added in same wells as negative controls. After 2 h plates were washed twice and 100 μl of secondary antibody were added (Anti-human IL-29/IFN-λ1 Antibody from R&D system catalogue number AF1598 reconstituted in PBS and diluted in diluent buffer at a concentration of 1 μg/ml). According to manufacture instruction these antibodies have respectively 5% for the monoclonal and 25% for the polyclonal cross-reactivity with IFN-λ2 and IFN-λ3. After 2 hours plates were washed and 100 μl of biotinylated antibody from Autogen Bioclear catalogue number ABN022B diluted 1 in 5000 in diluent buffer were added to each well for 2 hours. Plates were washed twice and 100 μl of streptaviden-HRP conjugated diluted 1 in 5000 in diluent buffer were added in each well for 15 minutes. Plates were washed three times and 100 μl of TMB substrate solution were added and the reaction was stopped with 50 μl of 1.8 M oh $H_2SO_4$ solution.

Statistical Analysis

Data are presented as mean±SEM. All data were analysed using one-way ANOVA and Bonferroni's multiple comparison post hoc test. Data were accepted as significantly different when $p<0.05$.

Results

Time Course of Type 1 and Type III Interferons mRNA Expression in BEAS-2B Cells

The expression of type 1 and type III interferons was studied during time course infection of BEAS-2B cells with RV16 by Taqman PCR. For detection of various alpha-interferon subtypes, two pairs of Taqman PCR primers and probes were selected. First primer and probe set detects subtypes 1,6 and 13, second primer and probe set detects subtypes 4,5,8,10,14,17,21. Primer and probe sets for detection of IL-29 (IFN-λ) and interferon-beta were also designed. FIG. 32a demonstrates the expression of type 1 interferons detected by IFNα.1, but no significant induction of these type 1 interferons mRNA by rhinovirus 16. With IFNα.2 statistically significant increase of type 1 interferon expression occurred in comparison to medium by 8 hours compared to 0-hour time point. At 0, 4 and 24 time points no induction was found. IL-29 mRNA expression was also statistically significant increased at 8 hour time point and we detected even higher induction by 24 hours ($p<0.05$) FIG. 32b. Interferon-beta mRNA expression was induced by rhinovirus 16 just once by 24 hours ($p<0.05$). 1000 fold induction was detected over medium. All the results were statistically significant ($p<0.05$) from 0-hour time point.

Detection of Interferon-alpha, Interferon-beta and IL-29 Proteins in RV Infected BEAS-2B Cells No significant induction of interferon-alpha protein during rhinovirus 16 infection was detected in BEAS-2B cells. Only traces of IFNA protein from approximately 0.3 to 0.5 pg/lm were detected by ELISA with range of detection from 0.63 to 20 pg/ml. The induction of IFNβ protein production was observed by 24 hours (FIG. 32c). The level of IFNβ protein production was statistically significantly ($p<0.05$) increased in rhinovirus 16 infected BEAS-2B cells in comparison to non infected cells. BEAS-2B cells infected with rhinovirus 16 produced high level of IL-29 protein by 24 hours ($p<0.05$) (FIG. 32d).

Time Course of Type 1 and Type III Interferon mRNA Expression in Primary Bronchial Epithelial Cell During Rhinovirus 16 Infection IFNα, IFNβ and IL-29 mRNA expression was assessed during a rhinovirus 16 time course at 0, 4, 8 and 24-hour time points. Alpha-interferons detected by IFNA.1 primer pair were expressed at all time points but never upregulated by rhinovirus 16. Using IFNA.2 we observed no induction by 4 hours and 10000-fold statistically significant induction over medium by 8 hours ($p<0.05$) which was still elevated by 24 hours (FIG. 33a). With IL-29 mRNA we observed slight induction by 4 and 8 hours and peak—1000000 fold induction over medium by 24 hours ($p<0.05$). Interferon-beta demonstrated no induction by 0, 4 and 8 hour time points, but was induced by rhinovirus 16 at 8 and 24 hours—100000 fold induction over medium (FIG. 33b).

Time Course of Type 1 and Type III Interferon mRNA Expression in Human Bronchial Epithelial Cell During Rhinovirus 1B Infection Alpha-interferons, interferon-beta and IL-29 mRNA expression was also observed during a rhinovirus 1B time course at 0, 4, 8 and 24-hour time points. Alpha-interferons detected by IFNα.1 primer pair were also expressed at all time points but not induced by rhinovirus 16. But mRNA of alpha-interferons detected by second primer pair IFNα.2 were not induced by rhinovirus 1B by 0 an 4 hours and peaked by 8 and 24 hours-10000 fold induction over medium. These results reached the statistical significance ($p<0.05$) (FIG. 34a). IL-29 mRNA was not induced by rhinovirus 1B by 0 and 4 hours. But some induction was observed by 8 hours (1000 fold induction over medium) and very high level of induction was detected by 24 hours—1000000 fold induction over medium ($p<0.05$). No induction of interferon-beta was observed by 4 hours, 100 fold induction over medium by 8 hours (not statistically significant) and peak at 24 hours-100000 fold induction over medium ($p<0.05$) (FIG. 34b).

Time Course of Type 1 and Type III Interferon mRNA Expression in Human Bronchial Epithelial Cell During Influenza Infection IFNα, IFNβ and IL-29 mRNA expression was also observed during influenza virus time course at 0, 4, 8 and 24-hour time points. Alpha-interferons detected by IFNA.1 primer pair were again expressed at all time points but not induced by influenza virus. Alpha-interferons detected by IFNα2 were not upregulated by 0 and 4 hours. Slight 10 fold induction was observed by 8 hours and 100 fold induction by 24 hours (FIG. 35a). IL-29 was induced by influenza virus at 4 and 8 hour time point (1000 fold induction over medium) and peaked at 24 hours (1000000 fold induction over medium). IFNβ m RNA induction was not seen at 4 and 8 hours. But 100-fold induction was detected at 8 hours and peaked at 24 hours-105 fold induction over medium (FIG. 35b).

Detection of Interferon-alpha, Interferon-beta and IL-29 Protein in HBEC Cells.

No production of Interferon-alpha, interferon-beta and IL-29 has been detected in HBEC cells infected with rhinovirus 16, 1B and influenza virus.

Discussion

As already described the expression of alpha-interferon types detected by first primer pair (types 1,6 and 13) was detected in both epithelial cell cultures (BEAS-2B and HBEC) with every respiratory virus used. But interestingly no up regulation of these interferon types was seen. So probably these alpha-interferon types are constitutively expressed in epithelial cell cultures but not induced by respiratory viruses which were used. And according to the ELISA data none of these alpha-interferon types are produced by epithelial cell lines.

The level of detection of alpha-interferons with second primer (types 2, 4, 5, 8, 10, 14, 17, 21) pair is quite different. It is induced in epithelial cell lines most often at 8 hours after the infection. This primer pair detects interferon-alpha 4 which can be the reason for this induction. But the story with protein is the same—it is not produced in epithelial cells.

It is also interesting that in HBEC the level of induction of alpha-interferons detected by second primer pair is lower when the cells are infected with influenza virus than they are infected by rhinoviruses 16 and 1B. Which indicates that influenza virus downregulates the induction of alpha interferons in epithelial cells.

So alpha-interferons are expressed, induced but not produced in epithelial cells after respiratory virus infection.

In the study interferon-beta was induced later than IFNα.2 alpha-interferons by respiratory viruses used.

Interestingly interferon-beta is differently produced in various epithelial cell lines. In BEAS-2B cells it is produced by 24 hours over rhinovirus infection thus in HBEC it is not produced after infection with neither rhinovirus16 nor with rhinovirus 1B and influenza virus.

IL-29 mRNA is induced in both epithelial cell lines by 8 and 24 hours.

In epithelial cells mRNA of IFNα.1 types of alpha-interferons is expressed and not induced and neither produced. mRNA of IFNα2 (which contain interferon alpha-4) types of interferon-alpha is induced by various rhinoviruses in studied epithelial cell line but no interferon-alpha is produced by epithelial cell lines.

So in epithelial cells differences in kinetics of type 1 and type III interferons can be seen. In BEAS-2B cells over the rhinovirus 16 infection alpha-interferons are expressed by 8 hours and then go down. Whilst interferon-beta peaks only at 24 hours. IL-29 mRNA in BEAS-2B cells starts rising at 8-hour time point and goes even higher at 24 hour time-point.

In HBEC infected with rhinovirus 16 alpha-interferons are up regulated by 8 hours and stay the same by 24 hour time point. Interferon-beta is up regulated by 24 hours as well as IL-29.

HBEC infected with rhinovirus 1B has the same kinetics of type 1 and type III interferon expression. They are up regulated at the same time points, which demonstrates that the kinetics of rhinovirus up regulation doesn't depend on rhinovirus type and probably indicates that they have the same induction pathway.

Although the level of induction of type 1 and type III interferons by influenza virus is lower in comparison to rhinovirus infection it has nearly the same kinetics: alpha-interferons also go up by 8 and 24 hours, beta-interferon and IL-29 peak at 24 hours. This also not variable from data obtained with rhinovirus infection.

UV-Data

It has been demonstrated that alpha-interferons are expressed in epithelial cells, Moreover some of them are induced by various respiratory viruses. But in both studied respiratory epithelial cell cultures they are not produced. Alpha-interferons are vital antiviral factors, as they induce hundreds of interferon inducible genes with antiviral properties. Some epithelial cell lines are able to produce alpha-interferons under certain conditions and stimuli, but it seems that either respiratory epithelium is not able to produce alpha-interferons, or respiratory viruses are not potent inducers of alpha-interferon production in respiratory epithelium. And it seems that the most important producers of alpha-interferons during respiratory virus infections are plasmacytoid dendritic cells (Cella, M., D. Jarrossay, F. Facchetti, O. Alebardi, H. Nakajima, A. Lanzavecchia, and M. Colonna. 1999. Plasmacytoid monocytes migrate to inflamed lymph nodes and produce large amounts of type I interferon. Nat. Med. 5:919-923.) and macrophages.

Interestingly beta-interferons are induced and produced in some epithelial cell lines, such as BEAS-2B.

The same is observed with IL-29, but induction of this type III interferon is earlier, to a greater level and more sustained than induction of the type I interferons.

EXAMPLE 6

Further Experimental Procedures

We provide below further experimental procedures used to derive the data presented herein.

Outline of Experimental Design and Techniques

RV16 experimental infections were induced in RV16 seronegative asthmatic and normal subjects. Baseline, acute infection and convalescent (6 week) blood, nasal, sputum and bronchoalveolar sampling were carried out to investigate baseline status, the acute phase of illness, and the degree of persistence. 17 normal, non-atopic and 11 atopic, mild asthmatic adults were recruited. Clinical and atopic status were defined by questionnaire, skin prick testing, serum IgE and lung function testing including histamine PC20. The asthmatic group were required to have a histamine $PC_{20} < 8$ mg/ml, the normal group >8 mg/ml. Individuals taking inhaled/oral steroids were excluded. Subjects were free of common cold symptoms for 6 weeks before commencing the study. Samples were taken according to established protocols developed in previous studies. These included blood, nasal lavage (NL), and bronchoalveolar lavage (BAL). Baseline samples were taken 2 wks prior to infection. Following inoculation on day 0, volunteers attended on days 3, 4 and 7 (at the height of cold symptoms) for further samples and lung function tests. Volunteers also attended daily from day 0 (prior to inoculation) to day 8 and on day 11 for NL to determine viral load. A third set of samples and lung function tests were performed at 6 weeks.

Experimental Infection with RV16

Protocols for experimental virus infection have been described in previous studies (Bardin et al., (1996) European Respiratory Journal 9, 2250-2255; Fraenkel et al., (1995) Am. J. Respir. & Crit. Care Med. 15, 879-886; Bardin et al., (1994) Clin Exp. Allergy 24, 457-464). Details regarding preparation and safety testing of the RV16 inoculum have been published (Bardin et al (1996) supra). Experimental infection was induced using 10000 $TCID_{50}$ RV16 on day 0 by nasal spray, with a DeVillbiss 286 atomizer. 2 aliquots of 500 µl (2500 $TCID_{50}$) were applied to each nostril. Inoculation was carried out in a specified clinical room at the end of the clinic day. Subjects avoided individuals with respiratory infection to minimise risk of a non-RV16 infection during the study. Infection was confirmed by culture of NL in HeLa cells for RV, or by positive serology. RNA was extracted from NL and BAL cell pellets and analysed by PCR for RV. Taqman PCR was used to quantify viral RNA. Co-infection with additional respiratory viruses including alternative RV serotypes was excluded by PCR for other viruses and by neutralisation of cultured rhinoviruses with RV16 specific antisera.

Criteria for Virological Confirmation of RV16 Infection

Successful experimental RV16 infection was confirmed by at least one of the following virological tests: Positive standard or Taqman RT-PCR for RV from upper (nasal lavage) and/or lower (induced sputum, bronchoalveolar lavage) airway samples; a rise in serum neutralising antibodies to RV16 6 weeks after inoculation of at least 4-fold (in the case of subjects in this study who were seronegative at baseline a titre of at least 1:4 was considered satisfactory); positive culture of RV from nasal lavage in HeLa cells with, after repeat passaging of virus to obtain a satisfactory concentration as determined by titration assay, clear RV cytopathic effect on HeLa cell monolayers with neutralisation by guinea pig specific RV16 antiserum. Standard picornavirus RT-PCR was performed on nasal lavage collected on the day with the peak Taqman RT-PCR viral load. Restriction enzyme analysis was then carried out to confirm the identity of positive picornavirus as RV and not enterovirus. Similarly, viral culture was performed using nasal lavage from the peak day on the basis of the Taqman results.

Collection of Clinical Data

Subjects recorded cold and chest symptom scores daily during an initial screening phase and from baseline, starting 2 weeks prior to the baseline bronchoscopy through to convalescence, finishing 2 weeks after the convalescent bronchoscopy performed 6 weeks after the experimental RV16 infection. In addition to symptom scores the subjects noted the timing and amount of medication such as inhaled bronchodilators required. Lung function was assessed by 2 methods. Firstly, subjects performed home spirometry using a portable handheld spirometer twice daily, in the morning immediately after waking and last thing at night. Secondly, Histamine PC20 tests were used to assess bronchial hyperreactivity on screening, at baseline, at day 6 post inoculation and in convalescence.

Diary Cards for Symptom Scores/Medication Usage/Spirometry Recording

Symptom assessment was by questionnaire for 2 weeks prior to, during and for 6 weeks after infection. The cold score was based on that of earlier common cold studies (Jackson et al (1958) Arch. Int. Med. 101:267-278). Symptoms (sneezing, headache, malaise, chilliness, nasal discharge, nasal obstruction, sore throat, cough, fever) were graded 0-3. A clinical cold was defined by a minimum cumulative score of 14 over 6 days (>20=severe cold) plus a subjective impression of cold or rhinorrhoea. Chest score symptoms included: cough on waking; wheeze on waking; daytime cough; daytime wheeze; daytime shortness of breath; nocturnal cough, wheeze or shortness of breath.

Analysis of Clinical Symptom Scores

To facilitate analysis of the clinical data the experimental infection protocol was divided up into separate stages. In addition to calculation of daily scores for individual symptom and total cold or chest scores, 2 week scores were calculated to allow for statistical analysis of the effects of RV infection on symptoms. It was decided to examine 2 week stages because following RV inoculation excess symptoms lasted for up to 2 weeks. The pre-baseline or screening stage was the 2 weeks up to the beginning of the baseline stage, the pre-convalescent stage was the 2 weeks immediately before the convalescent bronchoscopy. Neither of these 2 stages contained bronchoscopy. The baseline, acute infection and the convalescent stages all contain bronchoscopy on the $4^{th}$ day of that 2 week block. To examine the effects of the RV16 infection on symptoms daily and 2 week excess symptom scores were calculated by subtracting the scores obtained during the baseline stage from the corresponding days of the acute infection stage to correct for the effects of undergoing bronchoscopy, which itself may result in cold and chest symptoms and in short lived changes in lung function.

Lung Function Testing

Lung function testing was performed according to BTS/ARTP guidelines (Anonymous. (1994). Guidelines for the measurement of respiratory function. Recommendations of the British Thoracic Society and the Association of Respiratory Technicians and Physiologists. Respiratory Medicine 88:165-194). Subjects used a portable spirometer at home, the microDL (MicroMedical) morning and evening. Data was analysed using Spida software. In the lung function laboratory, and for bronchodilator reversibility, sputum induction and histamine challenge subjects used a Vitalograph Dry Wedge Bellows Spirometer. To facilitate comparison of changes in the 2 groups during the experimental infections firstly the % change in FEV1 from the mean obtained during the screening stage was calculated for each subject on the days following RV16 inoculation and secondly this was corrected for changes seen following bronchoscopy in the corresponding baseline days.

Histamine Challenge

Histamine challenge was performed according to ERS guidelines (Sterk et al (1993) Airway responsiveness. Standardized challenge testing with pharmacological, physical and sensitizing stimuli in adults. Report Working Party Standardization of Lung Function Tests, European Community for Steel and Coal. Official Statement of the European Respiratory Society. [Review] European Respiratory Journal—Supplement 16:53-83) using the 2 minute tidal breathing method. Bronchial hyperreactivity was assessed at baseline, day 6 post-infection and at 6 weeks.

Skin Prick Testing

Atopy was determined by skin prick testing to common aeroallergens: grass pollen; house dust mite; cat dander; dog hair; aspergillus fumigatus; cladosporium herbarum; alternaria alternata; silver birch; 3 trees; nettle pollen. Positive histamine/negative diluent controls were included. 1 positive reaction (wheal 3 mm greater than negative control) was considered diagnostic of atopy.

Nasal Lavage

NL was performed for: standard and Taqman RT-PCR for RV viral load; to confirm infection by effects on HeLa cell culture. 2.5 ml sterile normal saline was instilled into each nostril using a soft plastic pippete. Lavage was collected into a sterile petri dish, homogenised then aliquotted for storage at −80° C.

Peripheral Blood Analyses 50 ml blood was collected in heparinised tubes, diluted 1:1 with PBS then layered over lymphoprep. After centrifugation 2500 rpm 30 mins mononuclear cells were transferred to a single polypropylene tube and washed in RPMI-1640 10% FCS. The cell suspension was diluted 1:10 in 0.1% trypan blue for counting and assessment of viability by haemocytometer. Cells were resuspended in appropriate culture medium at the required cell density for subsequent experiments.

Serum Separation 10 ml blood was collected in a plain vacutainer tube, placed at 37 C 4 h to clot before centrifuging 2000 rpm 15 mins. Serum was aliquotted for storage at −80C for subsequent analysis for the presence of RV16 neutralising antibody.

Bronchoscopy

Bronchoscopies were performed according to BTS guidelines (British Thoracic Society Bronchoscopy Guidelines Committee. 2001. British Thoracic Society guidelines on diagnostic flexible bronchoscopy. Thorax 56:i1-i21) in the endoscopy unit at St Marys Hospital. Subjects were monitored by a separate physician or nurse. FEV1 was recorded prior to and after the bronchoscopy. A Keymed P100 bronchoscope was used with fenestrated forceps (Keymed FB-19C-1) and 3 mm sheathed brushes (Keymed BC-16C). BAL was performed by instillation of sterile normal saline (room temperature) into the right middle lobe bronchus in 8×30 ml aliquots with a 10s dwell time, aiming for 80% recovery. At baseline and 6 weeks BAL was obtained from the medial segment right middle lobe, at day 4 from the lateral segment to minimise effects of the previous BAL. BAL was collected in a single plastic chamber and transferred immediately to polypropylene tubes on ice for transport to the laboratory.

RV16 Serology

RV16 serology was performed at screening, baseline, d0 and 6 wks post infection by microneutralisation test for neutralising antibody to RV16 utilising HeLa cell monolayers in 96 well plates. Doubling dilutions of sera (50 µl) were made from 1:2 to 1:128. 50 µl diluted stock virus containing 100TCID$_{50}$ was added and the plate shaken at room temperature for 1 h. 100 µl freshly stripped HeLa cells 2×10$^5$ cells/ml were added and plates incubated at 37 C. Serum (cells+serum at 1:2 dilution), cell (cells, no serum, no virus) and virus (cells, no serum, stock virus) controls were included. Cytopathic effect (CPE) was read after 2-3 days. Antibody titre was defined by the greatest serum dilution completely neutralising viral CPE. Seroconversion was defined in seronegative subjects as a convalescent titre of RV16 neutralising antibodies of 1:4 or greater.

Virus Culture from Clinical Samples

The presence of RV in nasal lavage was determined by culture. This was initially performed at 37° C. and if negative repeated at 33° C. Virus was cultured by adding sample to a small volume of medium containing antibiotics and covering semi-confluent HeLa cells in a T25 flask, shaking at room temperature for 1 h, then adding additional medium and observing for CPE. If absent cells were lysed by 2 freeze/thaw cycles at 5 days and the clarified supernatant was added to fresh HeLa cells. If after 5 passages no CPE was observed virus was considered absent. Confirmation of cultured virus as RV16 involved a microneutralisation assay with RV16-specific sera (ATCC-titre 1:600). RV titre in culture supernatant was estimated by titration assay. Then in a 96-well plate 50 µl of diluted supernatant containing 100TCID$_{50}$ of virus was added to an equal volume of medium containing 2-fold serial dilutions of the specific RV16 antisera from 1:20 to 1:1280. The assay included positive (stock RV16) and cell (no virus) controls.

RNA Extraction from Stored Clinical Samples and Reverse Transcription Using Random Hexamer Primers RNA was extracted from samples using the QIAamp viral RNA mini kit (Qiagen) and reverse transcription performed using the omniscript RT kit (Qiagen) and random hexamer primers as per the manufacturer's instructions.

Standard PCR for Picornaviruses

RV RT-PCR was performed from cDNA produced by RT using random hexamer primers. PCR was performed using the Perkin Elmer 9600 GeneAmp PCR system using the published method (Johnston et al (1993) Journal of Clinical Microbiology 31:111-117) utilising the OL26/OL27 primer pair. The 380 bp picornavirus specific amplicon generated was visualised by ethidium bromide staining after electrophoresis on a 2% agarose gel and photographed by polaroid camera. RV amplicons were distinguished from those of enteroviruses by restriction digestion using Bgl I (Papadopoulos et al (1999) Journal of Virological Methods 80:179-185).

PCR for Additional Respiratory Viruses

The presence of respiratory viruses other than RV was excluded by PCR for *Mycoplasma* and *Chlamydia pneumoniae*, adenoviruses, respiratory syncytial virus, influenza AH1/AH3/B, parainfluenza 1-3, coronaviruses 229E and OC43. cDNA for these PCRs was produced by random hexamer RT. The protocols for these additional PCRs are previously published (Seemungal et al. (2001) American Journal of Respiratory & Critical Care Medicine 164:1618-1623)

Taqman RT-PCR for Picornavirus

Taqman RT-PCR was used to detect picornavirus in NL and BAL stored unprocessed after sampling at −80° C. RNA was extracted from samples using the QIAamp viral RNA mini kit (Qiagen) and reverse transcription performed using the omniscript RT kit (Qiagen) and random hexamer primers as per the manufacturer's instructions. PCR was performed using the PE Biosystems ABI Prism 7700 sequence detection system with AmplitaqGold DNA polymerase, a picornavirus specific primer pair (forward oligo 5'-GTG AAG AGC CSC RTG TGC T-3' (SEQ ID NO:26), reverse oligo 5'-GCT SCA GGG TTA AGG TTA GCC-3') (SEQ ID NO:27) and a FAM/TAMRA labelled picornavirus probe (FAM-TGA GTC CTC CGG CCC CTG AAT G-TAMRA) (SEQ ID NO:28).

A master mix was made up consisting of Qiagen quantitect probe mix, forward primer (50 nM) reverse primer (300 nM), probe (100 nM) and Rnase inhibitor. 23 µl of PCR master mix was added to 2 µl cDNA in each tube of the 96 well Taqman plate. Thermal cycling and detection of fluorescent PCR product was carried out using the PE Biosystems ABI Prism 7700 sequence detection system. The thermal cycle conditions used were: 50° C. 2 min; 95° C. 10 min; then 45 cycles× 95° C. 15 s/55° C. 20 s/72° C. 40 s. The Taqman RT-PCR methodology had been optimised by collaborators at Viropharma (Pevear et al (1999) Antimicrobial Agents & Chemotherapy 43:2109-2115). Fluorescence data was collected for each cycle and the cycle number (Ct) at which fluorescence rose above threshold was determined. Negative extraction (water), negative PCR (template only) and positive extraction (RV16 stock) were included. A standard curve was produced by including in the Taqman plate tubes containing 2 µl of RV plasmid serially diluted 10 fold from $10^8$ to $10^0$ copies/2 µl. After PCR each plasmid generates 1 copy dsDNA. Results were expressed for each sample in terms of copies/ml for NL and BAL by reference to the standard curve and taking into account both dilution factors inherent in processing to RNA and cDNA and the "double fluorescence" produced by each copy of dsDNA plasmid.

Statistical Analysis

Symptom scores, lung function, PC$_{20}$ values, virus load, cytokine and chemokine concentration and leukocyte numbers were compared within subjects to determine differences induced between baseline and the acute cold, and persistence of changes into convalescence. Intra-subject differences were analyzed using Wilcoxon's test. Differences between normal and asthmatic groups were analyzed using Mann Whitney's test at each phase of the study. Correlations between clinical illness severity, virus load, leukocyte counts and cytokine/chemokine concentrations were examined using Spearman's rank correlation to investigate possible causal relationships for these factors regulating the altered response in asthma.

BAL ex vivo Cultures

BAL cells from the bronchoscopy performed at baseline prior to experimental infection have been cultured for 48 h ex vivo in polypropylene tubes prior to harvesting of supernatant for cytokine production and cells for RNA, culture conditions including the following: medium only, medium +RV16 5MOI, medium +RV16 filter control, medium +LPS 0.1 μg/ml, medium +PHA 1 μg/ml, medium +allergen 5000 ISQ. On harvesting cells were vortexed briefly before centrifugation 1500 rpm 10 mins. Supernatent was aliquotted and stored at −80° C. for subsequent analysis by ELISA. 1 ml of trizol was added to lyse the cells before storage at −80° C. for subsequent analysis by RT-PCR.

EXAMPLE 7

Correlation of IFNλ Protein Levels with Clinical Indicators of Infection

The correlation between IFNλ protein levels and clinical indicators of respiratory infection was further investigated. The data is presented in FIG. 31. The methods used are outlined above in Example 6.

FIG. 31 shows IFNλ levels in bronchoalveolar cell supernatants, stimulated ex vivo with rhinovirus.

FIG. 31(a) shows the quantity of IFNλ protein in the supernatant of ex vivo RV-stimulated bronchoalveolar cells from normal and asthmatic subjects. It is clear from this data that cells isolated from asthmatic subjects produce much lower amounts of IFNλ protein than cells isolated from non-asthmatics subjects. Hence, bronchoalveolar cells from asthmatic subjects do not produce as much IFNλ protein when infected with RV than bronchoalveolar cells from normal subjects.

FIG. 31(b) illustrates the relationship between IFN☐ protein levels in patients infected with RV and the "cold score" of the patients when infected in vivo with rhinovirus 2 weeks later. "Cold score" is a clinical measure of the severity of the respiratory viral infection, as discussed above in Example 7. It is clear that patients that have lower IFNλ protein levels have a higher "cold score" than patients with more IFNλ protein. Accordingly, the data demonstrates the correlation between IFNλ protein levels and the severity of clinical indicators of respiratory viral infection. Hence IFNλ protein may be of use in the treatment of respiratory disorders.

FIG. 31(c) shows the relationship between lung capacity (as measured using FEV1 values) in patients infected with RV and IFN protein levels. It is clear that there is a correlation between the reduction in FEV1 and the level of IFNλ protein in the patients. Thus patients with lower IFNλ production at baseline suffer more severe airway obstruction when infected with rhinovirus 2 weeks later, hence IFNλ may be used in reducing severity of asthma excerbations.

FIG. 31(d) shows the amount of RV16 RNA in BAL cells (therefore lower airway virus load) taken during an in vivo infection with rhinovirus correlated with IFNλ protein production in BAL cells taken at baseline 2 weeks prior to the in vivo infection at baseline. Again, there is a correlation between the amount of RV16 RNA levels and IFNλ protein levels: the more IFNλ protein, the less RV16 RNA is present. Thus IFNλ may be used to diminish virus load in the lower airway thereby preventing/ameliorating virus induced asthma exacerbations.

The data presented in FIG. 31 provides correlations between lambda production and virus load, lung function and other clinical indicators of outcome. This data clearly shows the important biological role for IFNλs in protecting against viral induced exacerbations.

---

We claim:

1. A method of treating in an individual a rhinovirus-induced exacerbation of a respiratory disease selected from asthma and COPD, comprising administering to the lower respiratory tract an agent selected from the group consisting of:
   (a) an agent that increases interferon-β (IFN-β) expression; or
   (b) a polynucleotide which is capable of expressing such an agent or IFN-β,
   wherein the administration results in suppression of rhinovirus replication in the individual.

2. The method of claim 1 wherein said respiratory disease is asthma.

3. The method of claim 1 wherein said respiratory disease is COPD.

4. The method of claim 1, wherein the IFN-β comprises the sequence of human IFNβ-1a (SEQ ID NO: 2) or human IFNβ-1b (SEQ ID NO: 4).

5. The method of claim 2 wherein said respiratory disease is asthma and wherein said agent is administered simultaneously, separately or sequentially with an inhaled corticosteroid.

6. The method of claim 1 said agent is administered to the lung airways by means of an aerosol nebuliser.

7. The method of claim 1, wherein the agent is an agent that increases IFN-β expression.

8. The method of claim 1, wherein the agent is a polynucleotide capable of expressing IFN-β.

* * * * *

SEQUENCE LISTING

```
<160> NUMBER OF SEQ ID NOS: 28

<210> SEQ ID NO 1
<211> LENGTH: 757
<212> TYPE: DNA
<213> ORGANISM: Homo sapiens
<220> FEATURE:
<221> NAME/KEY: CDS
<222> LOCATION: (64)..(564)

<400> SEQUENCE: 1
atgaccaaca agtgtctcct ccaaattgct ctcctgttgt gcttctccac tacagctctt         60 tcc atg agc tac aac ttg ctt gga ttc cta caa aga agc agc aat ttt        108
    Met Ser Tyr Asn Leu Leu Gly Phe Leu Gln Arg Ser Ser Asn Phe
    1               5                  10                  15 cag tgt cag aag ctc ctg tgg caa ttg aat ggg agg ctt gaa tat tgc        156
Gln Cys Gln Lys Leu Leu Trp Gln Leu Asn Gly Arg Leu Glu Tyr Cys
                20                  25                  30 ctc aag gac agg atg aac ttt gac atc cct gag gag att aag cag ctg        204
Leu Lys Asp Arg Met Asn Phe Asp Ile Pro Glu Glu Ile Lys Gln Leu
            35                  40                  45 cag cag ttc cag aag gag gac gcc gca ttg acc atc tat gag atg ctc        252
Gln Gln Phe Gln Lys Glu Asp Ala Ala Leu Thr Ile Tyr Glu Met Leu
        50                  55                  60
```

```
cag aac atc ttt gct att ttc aga caa gat tca tct agc act ggc tgg     300
Gln Asn Ile Phe Ala Ile Phe Arg Gln Asp Ser Ser Ser Thr Gly Trp
         65                  70                  75 aat gag act att gtt gag aac ctc ctg gct aat gtc tat cat cag ata     348
Asn Glu Thr Ile Val Glu Asn Leu Leu Ala Asn Val Tyr His Gln Ile
 80                  85                  90                  95 aac cat ctg aag aca gtc ctg gaa gaa aaa ctg gag aaa gaa gat ttt     396
Asn His Leu Lys Thr Val Leu Glu Glu Lys Leu Glu Lys Glu Asp Phe
                100                 105                 110 acc agg gga aaa ctc atg agc agt ctg cac ctg aaa aga tat tat ggg     444
Thr Arg Gly Lys Leu Met Ser Ser Leu His Leu Lys Arg Tyr Tyr Gly
            115                 120                 125 agg att ctg cat tac ctg aag gcc aag gag tac agt cac tgt gcc tgg     492
Arg Ile Leu His Tyr Leu Lys Ala Lys Glu Tyr Ser His Cys Ala Trp
        130                 135                 140 acc ata gtc aga gtg gaa atc cta agg aac ttt tac ttc att aac aga     540
Thr Ile Val Arg Val Glu Ile Leu Arg Asn Phe Tyr Phe Ile Asn Arg
145                 150                 155 ctt aca ggt tac ctc cga aac tga agatctccta gcctgtccct ctgggactgg   594
Leu Thr Gly Tyr Leu Arg Asn
160                 165 acaattgctt caagcattct tcaaccagca gatgctgttt aagtgactga tggctaatgt   654
actgcaaatg aaaggacact agaagatttt gaaatttta ttaaattatg agttatttt    714 atttatttaa attttatttt ggaaaataaa ttattttttgg tgc                    757

<210> SEQ ID NO 2
<211> LENGTH: 166
<212> TYPE: PRT
<213> ORGANISM: Homo sapiens

<400> SEQUENCE: 2

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 3
<211> LENGTH: 720
<212> TYPE: DNA
```

-continued

```
<213> ORGANISM: Homo sapiens
<220> FEATURE:
<221> NAME/KEY: CDS
<222> LOCATION: (64)..(564)

<400> SEQUENCE: 3
atgaccaaca agtgtctcct ccaaattgct ctcctgttgt gcttctccac tacagctctt      60 tcc atg agc tac aac ttg ctt gga ttc cta caa aga agc agc aat ttt     108
    Met Ser Tyr Asn Leu Leu Gly Phe Leu Gln Arg Ser Ser Asn Phe
    1               5                  10                  15 cag agt cag aag ctc ctg tgg caa ttg aat ggg agg ctt gaa tat tgc     156
Gln Ser Gln Lys Leu Leu Trp Gln Leu Asn Gly Arg Leu Glu Tyr Cys
                20                  25                  30 ctc aag gac agg atg aac ttt gac atc cct gag gag att aag cag ctg     204
Leu Lys Asp Arg Met Asn Phe Asp Ile Pro Glu Glu Ile Lys Gln Leu
            35                  40                  45 cag cag ttc cag aag gag gac gcc gca ttg acc atc tat gag atg ctc     252
Gln Gln Phe Gln Lys Glu Asp Ala Ala Leu Thr Ile Tyr Glu Met Leu
        50                  55                  60 cag aac atc ttt gct att ttc aga caa gat tca tct agc act ggc tgg     300
Gln Asn Ile Phe Ala Ile Phe Arg Gln Asp Ser Ser Ser Thr Gly Trp
65                  70                  75 aat gag act att gtt gag aac ctc ctg gct aat gtc tat cat cag ata     348
Asn Glu Thr Ile Val Glu Asn Leu Leu Ala Asn Val Tyr His Gln Ile
80                  85                  90                  95 aac cat ctg aag aca gtc ctg gaa gaa aaa ctg gag aaa gaa gat ttt     396
Asn His Leu Lys Thr Val Leu Glu Glu Lys Leu Glu Lys Glu Asp Phe
                100                 105                 110 acc agg gga aaa ctc atg agc agt ctg cac ctg aaa aga tat tat ggg     444
Thr Arg Gly Lys Leu Met Ser Ser Leu His Leu Lys Arg Tyr Tyr Gly
            115                 120                 125 agg att ctg cat tac ctg aag gcc aag gag tac agt cac tgt gcc tgg     492
Arg Ile Leu His Tyr Leu Lys Ala Lys Glu Tyr Ser His Cys Ala Trp
        130                 135                 140 acc ata gtc aga gtg gaa atc cta agg aac ttt tac ttc att aac aga     540
Thr Ile Val Arg Val Glu Ile Leu Arg Asn Phe Tyr Phe Ile Asn Arg
145                 150                 155 ctt aca ggt tac ctc cga aac tga agatctccta gcctgtccct ctgggactgg     594
Leu Thr Gly Tyr Leu Arg Asn
160                 165 acaattgctt caagcattct tcaaccagca gatgctgttt aagtgactga tggctaatgt     654
actgcaaatg aaaggacact agaagatttt gaaattttta ttaaattatg agttattttt     714
atttat                                                               720

<210> SEQ ID NO 4
<211> LENGTH: 166
<212> TYPE: PRT
<213> ORGANISM: Homo sapiens

<400> SEQUENCE: 4

Met Ser Tyr Asn Leu Leu Gly Phe Leu Gln Arg Ser Ser Asn Phe Gln
1               5                  10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
```

```
                65                  70                  75                  80
Glu Thr Ile Val Glu Asn Leu Leu Ala Asn Val Tyr His Gln Ile Asn
                    85                  90                  95

His Leu Lys Thr Val Leu Glu Glu Lys Leu Glu Lys Glu Asp Phe Thr
                100                 105                 110

Arg Gly Lys Leu Met Ser Ser Leu His Leu Lys Arg Tyr Tyr Gly Arg
                115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 5
<211> LENGTH: 200
<212> TYPE: PRT
<213> ORGANISM: Homo sapiens

<400> SEQUENCE: 5

Met Ala Ala Ala Trp Thr Val Val Leu Thr Leu Val Leu Gly Leu
1               5                   10                  15

Ala Val Ala Gly Pro Val Pro Thr Ser Lys Pro Thr Thr Thr Gly Lys
                20                  25                  30

Gly Cys His Ile Gly Arg Phe Lys Ser Leu Ser Pro Gln Glu Leu Ala
                35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Gly Pro Ala Leu Glu Asp
                100                 105                 110

Val Leu Asp Gln Pro Leu His Thr Leu His His Ile Leu Ser Gln Leu
            115                 120                 125

Gln Ala Cys Ile Gln Pro Gln Pro Thr Ala Gly Pro Arg Pro Arg Gly
        130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr
        195                 200

<210> SEQ ID NO 6
<211> LENGTH: 200
<212> TYPE: PRT
<213> ORGANISM: Homo sapiens

<400> SEQUENCE: 6

Met Lys Leu Asp Met Thr Gly Asp Cys Thr Pro Val Leu Val Leu Met
1               5                   10                  15

Ala Ala Val Leu Thr Val Thr Gly Ala Val Pro Val Ala Arg Leu His
                20                  25                  30
```

```
Gly Ala Leu Pro Asp Ala Arg Gly Cys His Ile Ala Gln Phe Lys Ser
         35                  40                  45

Leu Ser Pro Gln Glu Leu Gln Ala Phe Lys Arg Ala Lys Asp Ala Leu
 50                  55                  60

Glu Glu Ser Leu Leu Leu Lys Asp Cys Arg Cys His Ser Arg Leu Phe
 65                  70                  75                  80

Pro Arg Thr Trp Asp Leu Arg Gln Leu Gln Val Arg Glu Arg Pro Met
                 85                  90                  95

Ala Leu Glu Ala Glu Leu Ala Leu Thr Leu Lys Val Leu Glu Ala Thr
                100                 105                 110

Ala Asp Thr Asp Pro Ala Leu Val Asp Val Leu Asp Gln Pro Leu His
                115                 120                 125

Thr Leu His His Ile Leu Ser Gln Phe Arg Ala Cys Ile Gln Pro Gln
130                 135                 140

Pro Thr Ala Gly Pro Arg Thr Arg Gly Arg Leu His His Trp Leu Tyr
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
                180                 185                 190

Val Ala Ser Gly Asp Leu Cys Val
            195                 200

<210> SEQ ID NO 7
<211> LENGTH: 200
<212> TYPE: PRT
<213> ORGANISM: Homo sapiens

<400> SEQUENCE: 7

Met Lys Leu Asp Met Thr Gly Asp Cys Met Pro Val Leu Val Leu Met
  1               5                  10                  15

Ala Ala Val Leu Thr Val Thr Gly Ala Val Pro Val Ala Arg Leu Arg
                 20                  25                  30

Gly Ala Leu Pro Asp Ala Arg Gly Cys His Ile Ala Gln Phe Lys Ser
         35                  40                  45

Leu Ser Pro Gln Glu Leu Gln Ala Phe Lys Arg Ala Lys Asp Ala Leu
 50                  55                  60

Glu Glu Ser Leu Leu Leu Lys Asp Cys Lys Cys Arg Ser Arg Leu Phe
 65                  70                  75                  80

Pro Arg Thr Trp Asp Leu Arg Gln Leu Gln Val Arg Glu Arg Pro Val
                 85                  90                  95

Ala Leu Glu Ala Glu Leu Ala Leu Thr Leu Lys Val Leu Glu Ala Thr
                100                 105                 110

Ala Asp Thr Asp Pro Ala Leu Gly Asp Val Leu Asp Gln Pro Leu His
                115                 120                 125

Thr Leu His His Ile Leu Ser Gln Leu Arg Ala Cys Ile Gln Pro Gln
130                 135                 140

Pro Thr Ala Gly Pro Arg Thr Arg Gly Arg Leu His His Trp Leu His
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
                180                 185                 190

Val Ala Ser Gly Asp Leu Cys Val
            195                 200
```

```
<210> SEQ ID NO 8
<211> LENGTH: 22
<212> TYPE: DNA
<213> ORGANISM: Artificial
<220> FEATURE:
<223> OTHER INFORMATION: FAM/TAMRA 6 labelled probe

<400> SEQUENCE: 8
tgagtcctcc ggcccctgaa tg                                              22

<210> SEQ ID NO 9
<211> LENGTH: 21
<212> TYPE: DNA
<213> ORGANISM: Artificial
<220> FEATURE:
<223> OTHER INFORMATION: Forward primer RVTM-1

<400> SEQUENCE: 9
gtgaagagcc cgcagtgtgc t                                               21

<210> SEQ ID NO 10
<211> LENGTH: 22
<212> TYPE: DNA
<213> ORGANISM: Artificial
<220> FEATURE:
<223> OTHER INFORMATION: Reverse primer RVTM-2

<400> SEQUENCE: 10
gctcgcaggg ttaaggttag cc                                              22

<210> SEQ ID NO 11
<211> LENGTH: 20
<212> TYPE: DNA
<213> ORGANISM: Artificial
<220> FEATURE:
<223> OTHER INFORMATION: Forward primer IFNA.1

<400> SEQUENCE: 11
cagagtcacc catctcagca                                                 20

<210> SEQ ID NO 12
<211> LENGTH: 20
<212> TYPE: DNA
<213> ORGANISM: Artificial
<220> FEATURE:
<223> OTHER INFORMATION: Reverse primer IFNA.1

<400> SEQUENCE: 12
caccaccagg accatcagta                                                 20

<210> SEQ ID NO 13
<211> LENGTH: 27
<212> TYPE: DNA
<213> ORGANISM: Artificial
<220> FEATURE:
<223> OTHER INFORMATION: FAM-TAMRA labelled probe

<400> SEQUENCE: 13
atctgcaata tctacgatgg cctcgcc                                         27

<210> SEQ ID NO 14
<211> LENGTH: 20
<212> TYPE: DNA
<213> ORGANISM: Artificial
<220> FEATURE:
<223> OTHER INFORMATION: IFNalpha 2 forward primer
```

```
<400> SEQUENCE: 14
ctggcacaaa tgggaagaat                                              20

<210> SEQ ID NO 15
<211> LENGTH: 20
<212> TYPE: DNA
<213> ORGANISM: Artificial
<220> FEATURE:
<223> OTHER INFORMATION: IFNalpha reverse primer

<400> SEQUENCE: 15
cttgagcctt ctggaactgg                                              20

<210> SEQ ID NO 16
<211> LENGTH: 27
<212> TYPE: DNA
<213> ORGANISM: Artificial
<220> FEATURE:
<223> OTHER INFORMATION: FAM-TAMRA labelled probe

<400> SEQUENCE: 16
tttctcctgc ctgaaggaca gacatga                                      27

<210> SEQ ID NO 17
<211> LENGTH: 21
<212> TYPE: DNA
<213> ORGANISM: Artificial
<220> FEATURE:
<223> OTHER INFORMATION: IL-29 forward primer

<400> SEQUENCE: 17
ggacgccttg gaagagtcac t                                            21

<210> SEQ ID NO 18
<211> LENGTH: 21
<212> TYPE: DNA
<213> ORGANISM: Artificial
<220> FEATURE:
<223> OTHER INFORMATION: IL-29 reverse primer

<400> SEQUENCE: 18
agaagcctca ggtcccaatt c                                            21

<210> SEQ ID NO 19
<211> LENGTH: 25
<212> TYPE: DNA
<213> ORGANISM: Artificial
<220> FEATURE:
<223> OTHER INFORMATION: FAM-TAMRA labelled probe

<400> SEQUENCE: 19
agttgcagct ctcctgtctt ccccg                                        25

<210> SEQ ID NO 20
<211> LENGTH: 18
<212> TYPE: DNA
<213> ORGANISM: Artificial
<220> FEATURE:
<223> OTHER INFORMATION: Interferon beta forward primer

<400> SEQUENCE: 20
cgccgcattg accatcta                                                18

<210> SEQ ID NO 21
<211> LENGTH: 22
```

```
<212> TYPE: DNA
<213> ORGANISM: Artificial
<220> FEATURE:
<223> OTHER INFORMATION: Interferon beta reverse primer

<400> SEQUENCE: 21
gacattagcc aggaggttct ca                                              22

<210> SEQ ID NO 22
<211> LENGTH: 30
<212> TYPE: DNA
<213> ORGANISM: Artificial
<220> FEATURE:
<223> OTHER INFORMATION: FAM-TAMRA labelled probe

<400> SEQUENCE: 22
tcagacaaga ttcatctagc actggctgga                                      30

<210> SEQ ID NO 23
<211> LENGTH: 21
<212> TYPE: DNA
<213> ORGANISM: Artificial
<220> FEATURE:
<223> OTHER INFORMATION: Primer 18STM.1

<400> SEQUENCE: 23
cgccgctaga ggtgaaattc t                                               21

<210> SEQ ID NO 24
<211> LENGTH: 21
<212> TYPE: DNA
<213> ORGANISM: Artificial
<220> FEATURE:
<223> OTHER INFORMATION: Primer 18STM.2

<400> SEQUENCE: 24
cattcttggc aaatgctttc g                                               21

<210> SEQ ID NO 25
<211> LENGTH: 21
<212> TYPE: DNA
<213> ORGANISM: Artificial
<220> FEATURE:
<223> OTHER INFORMATION: FAM-TAMRA labelled probe

<400> SEQUENCE: 25
accggcgcaa gacggaccag a                                               21

<210> SEQ ID NO 26
<211> LENGTH: 19
<212> TYPE: DNA
<213> ORGANISM: Artificial
<220> FEATURE:
<223> OTHER INFORMATION: Picornavirus specific forward primer

<400> SEQUENCE: 26
gtgaagagcc scrtgtgct                                                  19

<210> SEQ ID NO 27
<211> LENGTH: 21
<212> TYPE: DNA
<213> ORGANISM: Artificial
<220> FEATURE:
<223> OTHER INFORMATION: Picornavirus specific reverse primer

<400> SEQUENCE: 27
gctscagggt taaggttagc c                                               21
```

```
<210> SEQ ID NO 28
<211> LENGTH: 22
<212> TYPE: DNA
<213> ORGANISM: Artificial
<220> FEATURE:
<223> OTHER INFORMATION: FAM-TAMRA labelled probe

<400> SEQUENCE: 28
tgagtcctcc ggcccctgaa tg                                              22
```